(12) United States Patent
Pack et al.

(10) Patent No.: US 11,360,096 B2
(45) Date of Patent: Jun. 14, 2022

(54) COMPLEX BRET TECHNIQUE FOR MEASURING BIOLOGICAL INTERACTIONS

(71) Applicant: DUKE UNIVERSITY, Durham, NC (US)

(72) Inventors: Thomas Pack, Durham, NC (US); Jeffrey Smith, Durham, NC (US); Sudarshan Rajagopal, Durham, NC (US); Marc Caron, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/876,934

(22) Filed: May 18, 2020

(65) Prior Publication Data

US 2020/0363424 A1 Nov. 19, 2020

Related U.S. Application Data

(60) Provisional application No. 62/848,825, filed on May 16, 2019.

(51) Int. Cl.
 *C12Q 1/66* (2006.01)
 *G01N 33/68* (2006.01)

(52) U.S. Cl.
 CPC ........... *G01N 33/6809* (2013.01); *C12Q 1/66* (2013.01); *C12Y 113/12007* (2013.01); *G01N 2333/90241* (2013.01)

(58) Field of Classification Search
 CPC .................................. G01N 33/68; C12Q 1/66
 See application file for complete search history.

(56) References Cited

U.S. PATENT DOCUMENTS

| | | |
|---|---|---|
| 2010/0281552 A1 | 11/2010 | Encell et al. |
| 2012/0174242 A1 | 7/2012 | Binkowski et al. |
| 2014/0228239 A1 | 8/2014 | McCoy et al. |
| 2014/0348747 A1 | 11/2014 | Dixon et al. |
| 2016/0097042 A1 | 4/2016 | Dixon et al. |
| 2016/0252517 A1 | 9/2016 | Lo et al. |
| 2018/0284126 A1 | 10/2018 | Bar et al. |
| 2018/0313825 A1 | 11/2018 | Dixon et al. |
| 2020/0270586 A1* | 8/2020 | Hall ............... C12Y 113/12 |
| 2021/0018497 A1* | 1/2021 | Caron ............... C12N 9/16 |

FOREIGN PATENT DOCUMENTS

| | | |
|---|---|---|
| WO | WO 93/06868 | 4/1993 |
| WO | WO 94/08629 | 4/1994 |
| WO | WO 94/09056 | 4/1994 |
| WO | WO 96/26754 | 9/1996 |

OTHER PUBLICATIONS

Cranfill et al., "Quantitative Assessment of Fluorescent Proteins," Nat Methods, Jul. 2016, 13(7):557-562.
Götz et al., "Using Three-color Single-molecule FRET to Study the Correlation of Protein Interactions," J Vis Exp, 2018, 131:e56896, 12 pp.
Keskin et al., "Predicting Protein-Protein Interactions from the Molecular to the Proteome Level," Chem Rev, 2016, 116(8):4884-4909.
Liu et al., "An AP-MS- and BioID-compatible MAC-tag enables comprehensive mapping of protein interactions and subcellular localizations," Nature Communications, 2018, 9:1188, 16 pp.
Modell et al., "Systematic Targeting of Protein-Protein Interactions," Trends Pharmacol Sci, Aug. 2016, 37(8):702-713.
Smith et al., "Noncanonical scaffolding of Gαi and ß-arrestin by G protein-coupled receptors," Science, Jan. 21, 2021, eaay1833, doi: 10.1126/science.aay1833, Epub ahead of print, PMID: 33479120.
Tomalia et al., "Starburst Dendrimers: Molecular-Level Control of Size, Shape, Surface Chemistry, Topology, and Flexibility from Atoms to Macroscopic Matter," Angew Checm Int Ed Engl, 1990, 29:138-175.

\* cited by examiner

*Primary Examiner* — Maryam Monshipouri
(74) *Attorney, Agent, or Firm* — Womble Bond Dickinson (US) LLP

(57) ABSTRACT

Provided are methods for detecting protein interactions in a sample, the methods comprising: (a) detecting two or more polypeptides that when associated emit a first detectable signal in a first light emission spectrum; (b) contacting the two or more polypeptides with a third polypeptide conjugated to a dipole acceptor moiety that has a second light emission spectrum when excited within a light excitation spectrum, wherein the light excitation spectrum overlaps with the first light emission spectrum; and (c) detecting a second detectable signal emitted in the second light emission spectrum by the dipole acceptor moiety. Also provided are bioluminescent complexes comprising: (a) a first polypeptide conjugated to a dipole acceptor moiety, wherein the emits a first detectable signal in a first light emission spectrum.

6 Claims, 66 Drawing Sheets

Specification includes a Sequence Listing.

COMPLEX BRET TECHNIQUE FOR MEASURING BIOLOGICAL INTERACTIONS

CROSS REFERENCE TO RELATED APPLICATIONS

This application claims the benefit of U.S. Provisional Application No. 62/848,825 filed on May 16, 2019, which is incorporated herein by reference in its entirety.

STATEMENT REGARDING FEDERALLY SPONSORED RESEARCH

This invention was made with Government support under Federal Grant nos. 1R01GM122798-01A1, F31DA04116001 and R37MH073853 awarded by the NIH/NIGMS, NIH/NIDA, and NIH/NIMH respectively. The Federal Government has certain rights to this invention.

SEQUENCE LISTING

The instant application contains a Sequence Listing which has been submitted in ASCII format via EFS-Web and is hereby incorporated by reference in its entirety. Said ASCII copy, created on May 18, 2020, is named D118_1250US_1_Sequence_Listing and is 1,823 bytes in size.

BACKGROUND

Biological processes rely on covalent and non-covalent interactions between molecules, macromolecules and molecular complexes. In order to understand such processes, and to develop techniques and compounds to manipulate them for research, clinical and other practical applications, it is necessary to have tools available to detect and monitor these interactions. The study of these interactions, particularly under physiological conditions (e.g. at normal expression levels for monitoring protein interactions), requires high sensitivity.

SUMMARY

Provided are methods of detecting a bioluminescent signal in a sample via a complex bioluminescent resonance energy transfer (BRET) technique. Complex BRET offers a variety of advantages over traditional detection techniques, such as having less background noise, requiring less controls, simplicity of use, and scalability.

Some aspects comprise methods for detecting protein interactions in a sample, the methods comprising: (a) detecting two or more polypeptides that when associated emit a first detectable signal in a first light emission spectrum; (b) contacting the two or more polypeptides with a third polypeptide conjugated to a dipole acceptor moiety that has a second light emission spectrum when excited within a light excitation spectrum, wherein the light excitation spectrum overlaps with the first light emission spectrum; and (c) detecting a second detectable signal emitted in the second light emission spectrum by the dipole acceptor moiety.

In some aspects, the methods comprise (a) determining an increase in the ratio of the second detectable signal:the first detectable signal after the contact between the first polypeptide and the two or more additional polypeptides, as compared to the ratio of the second detectable signal:the first detectable signal before the contact between the first polypeptide and the two or more additional polypeptides, or (b) determining an increase in the second detectable signal following association between the two or more polypeptides and the third polypeptide, wherein the increase of (a) or (b) indicates that one or more of the two or more polypeptides interacts with the third polypeptide.

In some aspects, the dipole acceptor moiety comprises a fluorescent moiety, a dye, an arsenical protein label, a dye-protein conjugate pair, or a quantum dot. In some aspects, the dipole acceptor moiety comprises a fluorescent moiety. In some aspects, the second light emission spectrum is within a range of from about 445 nm to about 700 nm.

In some aspects, the two or more additional polypeptides comprise a first polypeptide conjugated to a first non-luminescent element and a second polypeptide conjugated to a second non-luminescent element, wherein the first and second non-luminescent elements form a complex that emits the first detectable signal. In some aspects, the first non-luminescent element and the second non-luminescent element each independently comprise a portion of a luciferase enzyme.

In some aspects, the sample comprises a cell, and the contacting is performed by cellular processes. In some aspects, the sample comprises a cell that expresses (i) the two or more polypeptides, and (ii) the third polypeptide conjugated to the dipole acceptor moiety, wherein the two or more polypeptides and the third polypeptide interact to form a complex, and wherein the method further comprises (iii) determining an increase in the ratio of the second detectable signal:the first detectable signal after the contact between the first polypeptide and the two or more additional polypeptides, as compared to the ratio of the second detectable signal:the first detectable signal before the contact between the first polypeptide and the two or more additional polypeptides, or (iv) determining an increase in the second detectable signal following association between the two or more polypeptides and the third polypeptide, wherein the increase of (iii) or (iv) indicates that one or more of the two or more polypeptides interacts with the third polypeptide.

In some aspects, the contacting places one or more of the two or more polypeptides in a proximity sufficient to allow resonance energy transfer from the two or more polypeptides to the dipole acceptor moiety.

Also provided are methods for detecting protein interactions and/or protein conformation changes in a sample, the method comprising: (a) placing in a proximity sufficient to allow resonance energy transfer (i) two or more polypeptides that when associated emit a first detectable signal in a first light emission spectrum and (ii) a third polypeptide conjugated to a dipole acceptor moiety that has a second light emission spectrum when excited within a light excitation spectrum, wherein the light excitation spectrum overlaps with the first light emission spectrum, and (b) detecting a second detectable signal emitted in the second light emission spectrum by the dipole acceptor moiety following association between the two or more additional polypeptides and the third polypeptide. In some aspects, the dipole acceptor moiety comprises a fluorescent moiety, a dye, an arsenical protein label, a dye-protein conjugate pair, or a quantum dot.

In some aspects (a) the two or more interaction elements are located on the same polypeptide; (b) one or more of the two or more interaction elements is located on the same polypeptide as the third interaction element; or (c) each of the two or more interaction elements and the third interaction element are located on the same polypeptide. In some aspects, the contacting results from a conformational change in a polypeptide comprising one or more of the interaction elements Also provided are bioluminescent complexes comprising: (a) a first polypeptide, and optionally, a second polypeptide, wherein the first polypeptide, or the first polypeptide associated with the optional second polypeptide, emits a first detectable signal in a first light emission spectrum; and (b) a third polypeptide conjugated to a dipole acceptor moiety that has a second light emission spectrum when excited within a light excitation spectrum, wherein the light excitation spectrum overlaps with the first light emission spectrum, wherein the dipole acceptor moiety emits a second detectable signal in the second light emission spectrum. In some aspects, the bioluminescent complexes comprise (a) the first polypeptide is conjugated to a first non-luminescent element, and (b) the second polypeptide conjugated to a second non-luminescent element, wherein the first polypeptide and second polypeptide interact and the first non-luminescent element and the second non-luminescent element form a complex that emits the first detectable signal.

In some aspects, the bioluminescent complexes have (a) the bioluminescent complex has a ratio of the second detectable signal:the first detectable signal that is increased as compared to a ratio of the second detectable signal:the first detectable signal determined in conditions in which the first, optionally second, and third polypeptides do not form a complex or (b) the bioluminescent complex has an increased second detectable signal as compared to a comparable second detectable signal determined in conditions in which the first, second, and third polypeptides do not form a complex.

In some bioluminescent complexes, the dipole acceptor moiety comprises a fluorescent moiety, a dye, an arsenical protein label, a dye-protein conjugate pair, or a quantum dot. In some bioluminescent complexes the dipole acceptor moiety comprises a fluorescent moiety. In some bioluminescent complexes, the first non-luminescent element and the second non-luminescent element each independently comprise a portion of a luciferase enzyme.

BRIEF DESCRIPTION OF THE DRAWINGS

FIG. 1A shows complementation of NANOBIT® components SmBiT and LgBiT that increases light output from LgBiT versus uncomplemented (basal state) and that can be used alone as a two-component, split luciferase assay or as a BRET donor in complex BRET; FIG. 1B shows how co-transfection of split luciferase components with the fluorescent protein monomeric kusabira orange (mKO) BRET acceptor enables complex BRET, and depicts a state where an mKO-tagged protein does not interact appreciably with NANOBIT®, and wherein spectral overlap exists between the NANOBIT® emission and the excitation spectrum of mKO (the detection system uses two light filters to detect light from either the NANOBIT® emission (480 nm BRET) or the mKO emission (542 nm long-pass), depicted here as shaded regions of the graphs); and FIG. 1C shows that same transfection conditions as in 1B, except mKO-tagged protein now comes into close enough proximity with the NANOBIT® to generate a BRET response, resulting in increased mKO emission in 1C versus 1B due to an increase in the underlying protein-protein interactions between the NANOBIT®-tagged components and the mKO-tagged component that is detected as an increase in the 542 nm long-pass:480 nm BRET signal ratio.

FIG. 2A shows arrangement of luciferase fragments and mKO acceptor fluorophore for complex BRET on G protein (LgBiT), β-arrestin-2 (mKO), and V2R (smBiT) when HEK 293T cells were transiently transfected with the indicated assay components and stimulated with the indicated agonist or vehicle; FIG. 2B shows a complex BRET ratio of Gαs-LgBiT:β-arrestin-mKO:V2R-smBiT following AVP (500 nM) treatment, where after AVP treatment an increase in the BRET ratio was observed in cells expressing β-arrestin-mKO, but not in cells expressing cytosolic (untagged) mKO; FIG. 2C shows quantification of Gαs-LgBiT:β-arrestin-mKO:V2R-smBiT complex formation in cells treated with either vehicle or AVP at a single five-minute timepoint; FIG. 2D shows a similar experiment to panel 2B, except testing the ability of Gαi to form a complex, wherein complex BRET ratio of Gαi-LgBiT:β-arrestin-mKO:V2R-smBiT following treatment with AVP lead to an increase in the observed BRET ratio in cells expressing β-arrestin-mKO, but not in cells expressing cytosolic mKO; FIG. 2E shows quantification of the Gαi-LgBiT: β-arrestin-mKO:V2R-smBiT formation in cells treated with either vehicle or AVP at a single five-minute timepoint; FIG. 2F shows rearrangement of complex BRET components Gαi protein (LgBiT), β-arrestin (SmBiT), and V2R (mKO); FIG. 2G shows a complex BRET ratio of Gαi-LgBiT:β-arrestin-smBiT:V2R-mKO following AVP treatment, where rearrangement of complex BRET tags increased the observed signal when compared to panel 2D; FIG. 2H shows five-minute quantification of $G_{\alpha i}$-LgBiT:β-arrestin-smBiT: V2R-mKO complexes relative to vehicle treatment; FIG. 2I shows a similar experiment to panel G, except testing the ability of Gαi-LgBiT:β-arrestin-smBiT to form a complex with the $\beta_2$AR-mKO as opposed to the V2R-mKO; after isoproterenol (10 μM) treatment, an increase in the BRET ratio was observed in cells expressing $\beta_2$AR-mKO, but not in cells expressing cytosolic mKO; FIG. 2J shows five-minute quantification of Gαi-LgBiT:β-arrestin-smBiT: $\beta_2$AR-mKO complexes induced by isoproterenol relative vehicle treatment. For kinetic experiments, *$P<0.05$ by two-way ANOVA, Fischer's post hoc analysis with a significant difference between treatments; for five-minute quantification, *$P<0.05$ by student's two-tailed t-test; Panels B-E, n=3 per condition; panels G-J, n=4 per condition. Graphs show mean±s.e.m. Cyto, cytoplasmic.

FIG. 3A shows single cells preceding treatment (basal), at 5 min, or at 30 min, with substantial co-localization of Gαi-mVenus:β-arrestin-mKO:V2R-Mars1 observed at 5 min, with less appreciated at 30 min (Scale bars, 5 μm); FIG. 3B shows an inset of images in (A) (scale bars, 1 μm); FIG. 3C shows line scan analysis of 5-minute time point, demonstrating colocalization of fluorophores following AVP (100 nM) treatment; and FIG. 3D shows line-scan analysis of a 30-minute time point. Data is representative of ten (basal), twenty (5 min) or fifteen (30 min) fields of view from three independent experiments.

FIG. 4A shows canonical G protein signaling following agonist treatment of the V2R; FIG. 4B shows cAMP generation following agonist treatment of the V2R; FIG. 4C shows canonical β-arrestin-2-smBiT recruitment following AVP (500 nM) treatment of the V2R-LgBiT; FIG. 4D shows arrangement of luciferase fragments on G protein (LgBiT) and β-arrestin (smBiT) in a two-component assay; FIG. 4E shows that only Gαi-LgBiT formed an observable complex with β-arrestin-2-smBiT after AVP (500 nM) treatment on cells overexpressing V2R in formation of Gα-LgBiT:β-arrestin-2-smBiT complexes; FIG. 4F shows that the concentration response on Gα-LgBiT:β-arrestin-2-smBiT association in cells overexpressing the V2R; FIG. 4G shows Gαi-LgBiT: β-arrestin-2-smBiT complex formation is sensitive to pertussis toxin pretreatment (data is normalized to maximal signal within each replicate); FIG. 4H shows loss of pertussis toxin sensitivity by mutation of the ADP-ribosylation site (C352) on Gαi-LgBiT C352I mutant: β-arrestin-2-smBiT complex formation; FIG. 4I shows the effect of pretreatment for 30 min with a membrane permeable V2R antagonist (SR121463, 10 uM) or a membrane impermeant V2R antagonist (H3192, 10 uM) on Gαi-LgBiT:β-arrestin-2-smBiT complex formation; FIG. 4J shows the effect of either membrane permeable SR121463 or impermeant H3192 V2R antagonists on V2R-LgBiT association with β-arrestin-2-smBiT; FIG. 4K shows the effect of either membrane permeable SR121463 or impermeable H3192 V2R antagonists on Gαi-LgBiT association with β-arrestin-2-smBiT; and FIG. 4L shows GST-β-arrestin-2 associates with purified Gαi in a pull-down assay. For panel A, experiments were conducted using the TGF alpha shedding assay in 'Δ3G' HEK 293 cells; all other experiments were conducted in WT HEK 293T cells overexpressing the indicated assay components. For panels A and E, $*P<0.05$ by two-way ANOVA, with a main effect of Gαs, or Gαs, respectively, vs other Gα subunits. For panels G and H, $*P<0.05$ by two-way ANOVA, main effect of pertussis toxin treatment. For panel I, $*P<0.05$ by two-way ANOVA, main effect of vehicle relative to either antagonist. For panels J and K, $*P<0.05$ by two-way ANOVA, Bonferroni post hoc of vehicle vs either antagonist. $\#P<0.05$, by two-way ANOVA, Bonferroni post hoc of SR121463 vs H3192. Panels A-C, E, F, H-J, n=3 per condition; K n=6-9 per condition, G n=8; L is representative of three pulldown experiments. Graphs show mean±s.e.m.

FIG. 5A shows a snake diagram of human CXCR3 WT showing relevant mutations, in which four alanine mutations were introduced into the C-terminus of CXCR3, (T360A/S361A/S364A/S366A) to create the phosphorylation deficient mutant CXCR3 4xA, and a C-terminal truncation was introduced at L344; FIG. 5B shows CXCR3 surface expression as assessed by flow cytometry in HEK 293 cells transiently transfected with either CXCR3 WT, CXCR3 4xA, CXCR3 L344X, or an untransfected control; FIG. 5C shows canonical β-arrestin-2-YFP recruitment to either CXCR3-WT-RLuc, CXCR3-4xA-RLuc, or CXCR3-L344X-RLuc following CXCL11 treatment at the indicated concentration; FIG. 5D shows assessment of canonical G protein signaling of CXCR3 WT, CXCR3 4xA, or CXCR3 L344X via TGF alpha assay following CXCL11 treatment at the indicated concentration; FIG. 5E shows Gαi-LgBiT:β-arrestin-2-smBiT complexes in HEK 293 cells overexpressing either CXCR3 WT, CXCR3 4xA, or CXCR3 L344X and treated with CXCL11 at the indicated concentration; and FIG. 5F shows Gαi-LgBiT:β-arrestin-2-smBiT complexes in HEK 293 cells overexpressing either CXCR3 WT, CXCR3 4xA, or CXCR3 L344X and treated with CXCL11 (1 μM). For panel A, one-way ANOVA with Bonferroni post hoc analysis relative to WT. For panels C-F, $*P<0.05$, two-way ANOVA with main effect of receptor. NS, not significant. Graphs show mean±s.e.m.

FIG. 7A shows the arrangement of split luciferase components and mKO complex BRET on G protein (LgBiT), β-arrestin (smBiT), or ERK (mKO); FIG. 7B shows complex BRET association of Gαi-LgBiT, β-arrestin-smBiT, and ERK2-mKO in cells overexpressing untagged V2R following treatment with AVP (500 nM) (data were normalized to both vehicle treatment and cytosolic mKO); FIG. 7C shows representative immunoblot of phospho and total ERK1/2 in 'triple G' HEK 293 cells pretreated with PTX (200 ng/mL) and/or βarr1/2 siRNA, stimulated with either vehicle or AVP (500 nM) (ERK1/2 phosphorylation was nearly eliminated in cells treated with both PTX and βarr1/2 siRNA); FIG. 7D shows quantification of FIG. 7C ERK immunoblots (100% represents the maximal signal of phospho ERK/total ERK in the control, vehicle-treated condition); FIG. 7E shows representative immunoblot of β-arrestin, Gαi, phospho-ERK, and total ERK1/2 in 'total G' HEK 293 cells transfected with the indicated amounts of Gαi and/or βarr1/2 (100% represents the signal of phospho ERK/total ERK in the control siRNA, absent PTX, AVP stimulated condition); and FIG. 7F shows quantification of panel E ERK immunoblots. $*P<0.05$, $***P<0.001$, two-way ANOVA with Bonferroni post hoc to no treatment, control siRNA group. The net BRET ratio of cytosolic mKO control was subtracted from the net BRET ratio of ERK-mKO to yield an adjusted BRET ratio that is the ordinate of panel B. Immunoblots are representative of four to five separate experiments. For panel B, n=5; panel D, n=4; G, n=5 per condition. NT, no transfection of either Gαi or β-arrestin. PTX, pertussis toxin. Graphs show mean±s.e.m.

FIG. 8D shows representative images of the four TRV120023 migration conditions in HEK 293 cells stably expressing $AT_1R$; FIG. 8E shows quantification of PTX pretreatment (200 ng/mL) and/or βarr1/2 siRNA on TRV120023-induced migration for the experiment shown in FIG. D; FIG. 8F shows a split luciferase assay for monitoring Gαi-LgBiT:β-arrestin-smBiT association after treatment of AT₁R with either angiotensin II or TRV120023; and FIG. 8G shows a schematic of three described GPCR transduction effectors. *P<0.05, two-way ANOVA with Bonferroni post hoc to no treatment, control siRNA group. #P<0.05, two-way ANOVA with Bonferroni post hoc compared to control siRNA, PTX pretreated group. For panel A, n=4 per condition, for panels B and C, n=4-5 per condition, for panels E and F, n=4 per condition. Graphs show mean±s.e.m.

FIG. 9A shows Gα protein-LgBiT-β-arrestin-2-smBiT complex association with mKO that was expressed either in the cytosol (untagged) or tagged to the C-terminus of V2R; for the cytosolic mKO groups, untagged V2R was transfected to allow for AVP-induced G protein:β-arrestin association; to kinetically assess ligand-induced increases in V2R-mKO:Gαprotein-LgBiT:β-arrestin-2-smBiT complex formation, three baseline reads were conducted, followed by treatment with either vehicle or AVP (500 nM); consistent with a selective interaction, only AVP treatment of the V2R-mKO condition resulted in formation of a V2R-mKO:Gα protein-LgBiT:β-arrestin-2-smBiT megaplex; baseline differences in the BRET ratio observed between cytosolic mKO and V2R-mKO reflected differences in mKO localization within cells; FIG. 9B shows a similar experiment to FIG. 9A, except assessing a β2AR-mKO:Gαi-LgBiT:β-arrestin-2-smBiT megaplex following treatment with either vehicle or isoproterenol (10 μM) after three baseline reads; mKO was either expressed in the cytosol or tagged on the C-terminus of β2AR; FIGS. 9C-H show experiments conducted to test the specificity of the complex BRET assay to test if an untagged receptor stimulated with its cognate ligand could form a 'bystander,' non-specific megaplex, wherein FIG. 9C shows that only when AVP was paired with V2R-mKO was a V2R-mKO:Gαi-LgBiT:β-arrestin-2-smBiT megaplex formed; no increase in the BRET ratio was observed under conditions with cells expressing β2AR-mKO and untagged V2R and treated with AVP, indicating complex BRET selectively measures GPCR megaplexes and minimizes bystander effects; FIG. 9D shows a 5 minute time point of data shown in FIG. C; FIG. 9E shows a similar experiment to FIG. 9C, except assessing the ability of isoproterenol (10 μM) to quantify β2AR-mKO:Gαi-LgBiT:β-arrestin-2-smBiT in cells that expressed either native β2AR with V2R-mKO or β2AR-mKO with untagged V2R; similar to panel C, only when isoproterenol was paired with β2AR-mKO is a β2AR-mKO:Gαi-LgBiT:β-arrestin-2-smBiT megaplex formed, and no increase in the BRET ratio was observed under conditions with cells expressing β2AR-mKO and untagged V2R; FIG. 9F shows a 5 minute time point of data shown in panel E; In FIG. G and FIG. H, only luciferase complementation in the 480 nm channel (which indicates Gαi-LgBiT:β-arrestin-2-smBiT complex formation) is graphed (no BRET data is included); the same cells and conditions utilized in panels C-F are used (this control experiment assessed the ability of either native V2R or V2R-mKO to induce association of Gαi-LgBiT:β-arrestin-2-smBiT); more particularly FIG. 9G shows that AVP (500 nM) induced association of Gαi and β-arrestin-2 in cells expressing either native V2R or V2R-mKO (slight deviations in E max likely reflect minor differences in surface expression between V2R or V2R-mKO); FIG. 9H shows a similar experiment to panel G, except assessing the ability of isoproterenol (10 μM) to induce association of Gαi-LgBiT:β-arrestin-2-smBiT in cells expressing either untagged β2AR or β2ARmKO (similar to panel G, slight deviations in efficacy likely reflect minor differences in receptor surface expression). For panels C, E, *P<0.05, two-way ANOVA with main effect of receptor condition. For panels D, F, *P<0.05, two-tailed t-test. Panels A, B, n=4 per condition; panels C-H, n=3 per condition. Individual wells in the 96 well plates of the 3 different replicates are shown in panels D and F for the purpose of displaying experimental variability. Graphs show mean±s.e.m.

DETAILED DESCRIPTION

Figure 1A:
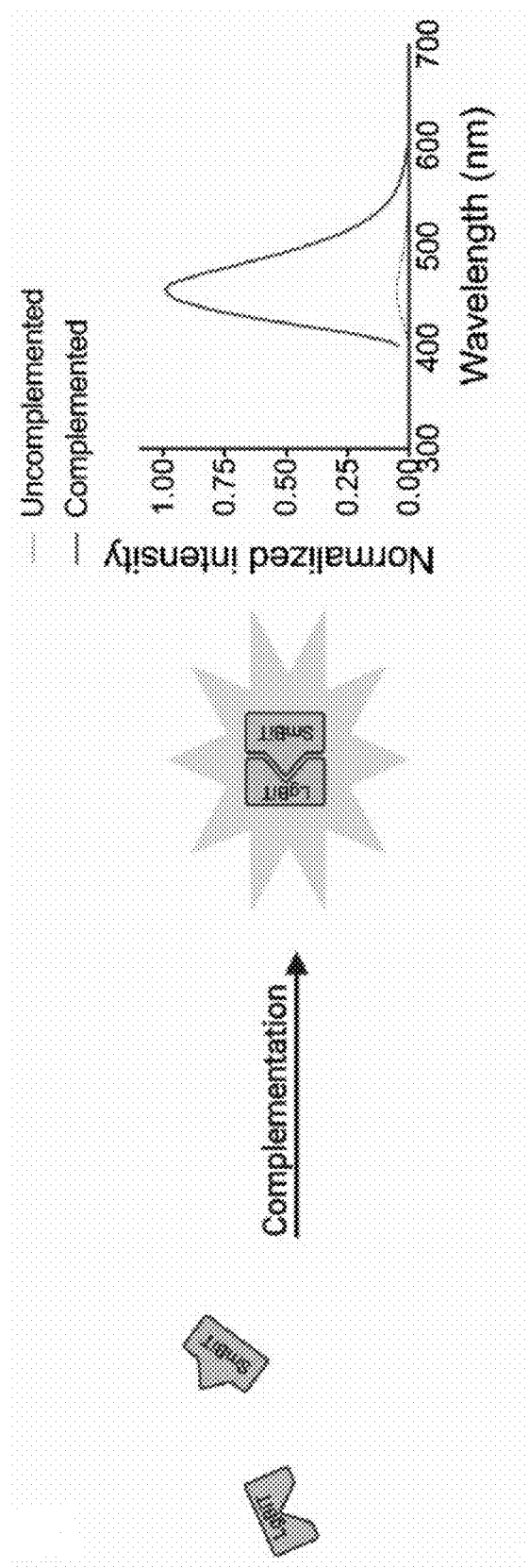
FIGS. 1A-C illustrate light spectra of individual components used for complex BRET and a light filter detection scheme, where

As used herein, the singular forms "a", "an", and "the" include both singular and plural referents unless the context clearly dictates otherwise.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, such as variations of +/−10% or less from the specified value, unless specifically identified to mean a separate variation, such as +1-5% or less, +/−1% or less, or +/−0.1% or less of and from the specified value. It is to be understood that the value to which the modifier "about" refers is itself also specifically, and preferably, disclosed.

As used herein, the term "substantially" means that the recited characteristic, parameter, and/or value need not be achieved exactly, but that deviations or variations, including for example, tolerances, measurement error, measurement accuracy limitations and other factors known to those skilled in the art, may occur in amounts that do not preclude the effect the characteristic was intended to provide. A characteristic or feature that is substantially absent (e.g., substantially non-luminescent) may be one that is within the noise, beneath background, below the detection capabilities of the assay being used, or a small fraction (e.g., <1%, <0.1%, <0.01%, <0.001%, <0.00001%, <0.000001%, <0.0000001%) of the significant characteristic (e.g., luminescent intensity of a bioluminescent protein or bioluminescent complex).

As used herein, the term "bioluminescence" refers to production and emission of light by a chemical reaction catalyzed by, or enabled by, an enzyme, protein, protein complex, or other biomolecule (e.g., bioluminescent complex). In some aspects, a substrate for a bioluminescent entity (e.g., bioluminescent protein or bioluminescent complex) is converted into an unstable form by a bioluminescent entity; the substrate subsequently emits light.

As used herein the term "complementary" refers to the characteristic of two or more structural elements (e.g., peptide, polypeptide, nucleic acid, small molecule, etc.) of being able to hybridize, dimerize, trimerize, or otherwise form a complex with each other. For example, a "complementary peptide and polypeptide" are capable of coming together to form a complex. Complementary elements may require assistance to form a complex (e.g., from interaction elements), for example, to place the elements in the proper conformation for complementarity, to co-localize complementary elements, to lower interaction energy for complementarity, etc.

As used herein, the term "complex" refers to an assemblage or aggregate of molecules (e.g., peptides, polypeptides, etc.) in direct and/or indirect contact with one another. In one aspect, "interact," or more particularly, "directly interact" means two or more molecules (e.g., proteins) are close enough so that attractive noncovalent interactions, such as Van der Waal forces, hydrogen bonding, ionic and hydrophobic interactions, and the like, dominate the interaction of the molecules. In such an aspect, a complex of molecules (e.g., a peptide and polypeptide) is formed under assay conditions such that the complex is thermodynamically favored (e.g., compared to a non-aggregated, or non-complexed, state of its component molecules). The term "complex," unless described as otherwise, refers to the assemblage of two or more (such as three or more) molecules (e.g., peptides, polypeptides or a combination thereof).

As used herein, the term "non-luminescent" refers to an entity (e.g., peptide, polypeptide, complex, protein, etc.) that exhibits the characteristic of not emitting a detectable amount of light in the visible spectrum (e.g., in the presence of a substrate). For example, an entity may be referred to as non-luminescent if it does not exhibit detectable luminescence in a given assay. As used herein, the term "non-luminescent" can be synonymous with the term "substantially non-luminescent." For example, a non-luminescent polypeptide (NLpoly) is substantially non-luminescent, exhibiting, for example, a 10-fold or more (e.g., 100-fold, 200-fold, 500-fold, $1\times10^3$-fold, $1\times10^4$-fold, $1\times10$-fold, $1\times10^6$-fold, $1\times10^7$-fold, etc.) reduction in luminescence compared to a complex of the NLpoly with its non-luminescent complement peptide. In some aspects, an entity is "non-luminescent" if any light emission is sufficiently minimal so as not to create interfering background for a particular assay.

As used herein, the terms "non-luminescent peptide" (e.g., NLpep) and "non-luminescent polypeptide" (e.g., NLpoly) refer to peptides and polypeptides that exhibit substantially no luminescence (e.g., in the presence of a substrate), or an amount that is beneath the noise, or a 10-fold or more (e.g., 100-fold, 200-fold, 500-fold, $1\times10^3$-fold, $1\times10^4$-fold, $1\times10^5$-fold, $1\times10^6$-fold, $1\times10^7$-fold, etc.) when compared to a significant signal (e.g., luminescent complex) under standard conditions (e.g., physiological conditions, assay conditions, etc.) and with typical instrumentation (e.g., luminometer, etc.). In some aspects, such non-luminescent peptides and polypeptides assemble, according to the criteria described herein, to form a bioluminescent complex. As used herein, a "non-luminescent element" is a non-luminescent peptide or non-luminescent polypeptide. The term "bioluminescent complex" refers to the assembled complex of two or more non-luminescent peptides and/or non-luminescent polypeptides. The bioluminescent complex catalyzes or enables the conversion of a substrate for the bioluminescent complex into an unstable form; the substrate subsequently emits light. When uncomplexed, two non-luminescent elements that form a bioluminescent complex may be referred to as a "non-luminescent pair." If a bioluminescent complex is formed by three or more non-luminescent peptides and/or non-luminescent polypeptides, the uncomplexed constituents of the bioluminescent complex may be referred to as a "non-luminescent group."

As used herein, the term "dipole acceptor moiety" refers to a molecule that can accept energy from a donor molecule via resonance energy transfer (e.g., fluorescence resonance energy transfer or electronic energy transfer). For instance, a donor chromophore in an electronic excited state can transfer energy to a dipole acceptor moiety (e.g., an acceptor chromophore) through nonradiative dipole-dipole coupling. The dipole acceptor moiety has a light excitation spectrum (e.g., wavelengths of light that can be absorbed by the dipole acceptor moiety for excitation) and a light emission spectrum (e.g., wavelengths of light released by the dipole acceptor moiety with return of the molecule to a ground, or less excited, state).

As used herein, the term "interaction element" refers to a moiety that assists in bringing together a pair of non-luminescent elements or a non-luminescent group to form a bioluminescent complex, or a moiety that assists in bringing together a dipole acceptor moiety and a pair of non-luminescent elements. In some aspects, a pair of interaction elements (a.k.a. "interaction pair") is attached to a pair of non-luminescent elements (e.g., non-luminescent peptide/polypeptide pair), and the attractive interaction between the two interaction elements facilitates formation of the bioluminescent complex; although the present invention is not limited to such a mechanism, and an understanding of the mechanism is not required to practice the invention. In some aspects, an interaction element is attached to a dipole acceptor moiety. Interaction elements may facilitate formation of the bioluminescent complex by any suitable mechanism (e.g., bringing non-luminescent pair/group and/or dipole acceptor moiety into close proximity, placing a non-luminescent pair/group and/or dipole acceptor moiety in proper conformation for stable interaction, reducing activation energy for complex formation, combinations thereof, etc.). An interaction element may be a protein, polypeptide, peptide, small molecule, cofactor, nucleic acid, lipid, carbohydrate, antibody, etc. An interaction pair may be made of two of the same interaction elements (i.e. homopair) or two or more different interaction elements (i.e. heteropair). In the case of a heteropair, the interaction elements may be the same type of moiety (e.g., polypeptides) or may be two different types of moieties (e.g., polypeptide and small molecule). In some aspects, in which complex formation by the interaction pair or group is studied, an interaction pair may be referred to as a "target pair"/"target group" or a "pair of interest"/"group of interest" and the individual interaction elements are referred to as "target elements" (e.g., "target peptide," "target polypeptide," etc.) or "elements of interest" (e.g., "peptide of interest," "polypeptide or interest," etc.). The term "pair" is used to refer to two elements; however, a pair may be a part of a larger group. Thus, for example, if a complex includes three or more interaction elements, then any two of elements may be considered a pair. In some aspects, multiple interaction elements may be present in a single peptide or polypeptide. For instance, a polypeptide attached to a non-luminescent element can have (i) a first interaction element that pairs with a polypeptide attached to a second non-luminescent element, and (ii) a second interaction element that pairs with a polypeptide attached to a dipole acceptor moiety. Likewise, a polypeptide attached to a dipole acceptor moiety can have (i) a first interaction element that pairs with a polypeptide attached to a first non-luminescent element and (ii) a second interaction element that pairs with a polypeptide attached to a second non-luminescent element. In some aspects, the interactions between first, second, and/or third interaction elements are from protein-protein-protein interactions, i.e., that form a complex.

As used herein, the term "preexisting protein" refers to an amino acid sequence that was in physical existence prior to a certain event or date. A "peptide that is not a fragment of a preexisting protein" is a short amino acid chain that is not a fragment or sub-sequence of a protein (e.g., synthetic or naturally-occurring) that was in physical existence prior to the design and/or synthesis of the peptide.

As used herein, the term "fragment" refers to a peptide or polypeptide that results from dissection or "fragmentation" of a larger whole entity (e.g., protein, polypeptide, enzyme, etc.), or a peptide or polypeptide prepared to have the same sequence as such. Therefore, a fragment is a subsequence of the whole entity (e.g., protein, polypeptide, enzyme, etc.) from which it is made and/or designed. A peptide or polypeptide that is not a subsequence of a preexisting whole protein is not a fragment (e.g., not a fragment of a preexisting protein). A peptide or polypeptide that is "not a fragment of a preexisting bioluminescent protein" is an amino acid chain that is not a subsequence of a protein (e.g., natural or synthetic) that: (1) was in physical existence prior to design and/or synthesis of the peptide or polypeptide, and (2) exhibits substantial bioluminescent activity.

As used herein, the term "subsequence" refers to peptide or polypeptide that has 100% sequence identity with another, larger peptide or polypeptide. The subsequence is a perfect sequence match for a portion of the larger amino acid chain.

As used herein, the term "sequence identity" refers to the degree that two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window). (2) determining the number of positions containing identical (or similar) monomers (e.g., same amino acids occurs in both sequences, similar amino acid occurs in both sequences) to yield the number of matched positions. (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "physiological conditions" encompasses any conditions compatible with living cells, e.g., predominantly aqueous conditions of a temperature, pH, salinity, chemical makeup, etc. that are compatible with living cells.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Sample may also refer to cell lysates or purified forms of the peptides and/or polypeptides described herein. Cell lysates may include cells that have been lysed with a lysing agent or lysates such as rabbit reticulocyte or wheat germ lysates. Sample may also include cell-free expression systems. Environmental samples include environmental material such as surface matter, soil, water, crystals and industrial samples. Such examples are not however to be construed as limiting the applicable sample types.

As used herein, unless otherwise specified, the terms "peptide" and "polypeptide" refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids). The terms "first," "second," "third," etc. when referring to peptides, polypeptides, or other elements or aspects are to be interpreted based on the context in which they are used. By way of example, in some aspects a "first polypeptide" can be conjugated to a dipole acceptor moiety. However, in some aspects a "first polypeptide" can be conjugated to a non-luminescent element.

The study of protein interactions, particularly under physiological conditions and/or at physiologic expression levels, is benefited by high sensitivity. In some aspects, protein interactions with small molecules, nucleic acids, other proteins, etc. are detected in part based on the association of two non-luminescent elements that come together to form a bioluminescent complex capable of producing a detectable signal (e.g., luminescence), or two non-luminescent elements and one dipole acceptor moiety that come together to from a bioluminescent complex capable of producing a detectable signal (e.g., luminescence). The formation of the bioluminescent complex is dependent upon the protein interaction that is being monitored. As used herein, a "signal element" is an element that emits a detectable signal or is capable of emitting a detectable signal upon complexation (e.g., a non-luminescent element or a dipole acceptor moiety).

Some aspects comprise compositions and methods for the assembly of a bioluminescent complex from two or more non-luminescent peptide and/or polypeptide units (e.g., non-luminescent pair) and one or more dipole acceptor moiety. In some aspects, the non-luminescent peptide and/or polypeptide units are not fragments of a preexisting protein (e.g., are not complementary subsequences of a known polypeptide sequence). For instance, bioluminescent activity can be conferred upon a non-luminescent polypeptide via structural complementation with a non-luminescent peptide.

Some aspects comprise non-luminescent pairs and a dipole acceptor moiety for use in detecting and monitoring molecular interactions (e.g., that include protein-protein, protein-DNA, protein-RNA interactions, RNA-DNA, protein-small molecule, RNA-small-molecule, etc.). Also provided herein are complementary panels of interchangeable non-luminescent elements (e.g., peptides and polypeptides) that have variable affinities and luminescence upon formation of the various bioluminescent complexes (e.g., a high-affinity/high-luminescence pair, a moderate-affinity/high-luminescence pair, a low-affinity/moderate-luminescence pair, etc.). Utilizing different combinations of non-luminescent elements provides an adaptable system comprising various pairs ranging from lower to higher affinities, luminescence and other variable characteristics. Likewise, dipole acceptor moieties can be used that have variable luminescence upon formation of a bioluminescent complex (e.g., variable light emission wavelengths, intensities, etc.) This adaptability allows the detection/monitoring of molecular interactions to be fine-tuned to the specific molecule(s) of interest and expands the range of molecular interactions that can be monitored to include interactions with very high or low affinities. Further provided herein are methods by which non-luminescent pairs (or groups) and panels of non-luminescent pairs (or groups) are developed and tested. Also provided are methods by which dipole acceptor moieties and panels of dipole acceptor moieties are developed and tested.

In some aspects, the interaction between the peptide/polypeptide members of the non-luminescent pair or group alone is insufficient to form a bioluminescent complex and produce a resulting bioluminescent signal. However, if an interaction element is attached to each peptide/polypeptide member of the non-luminescent pair and dipole acceptor moiety, then the interactions of the interaction pair or group (e.g., to form an interaction complex) facilitate formation of the bioluminescent complex. In such aspects, the bioluminescent signal from the bioluminescent complex (or the capacity to produce such a signal in the presence of substrate) serves as a reporter for the formation of the interaction complex. If an interaction complex is formed, then a bioluminescent complex is formed, and a bioluminescent signal is detected/measured/monitored (e.g., in the presence of substrate). If an interaction complex fails to form (e.g., due to unfavorable conditions, due to unstable interaction between the interaction elements, due to incompatible interaction elements), then a bioluminescent complex does not form, and a bioluminescent signal is not produced.

In some aspects, the dipole acceptor moiety is excitable at one or more wavelengths within a light excitation spectrum. In some aspects, the bioluminescent complex formed by the non-luminescent pair produces a detectable signal emitted in a light emission spectrum (e.g., at one or more wavelengths within the light emission spectrum) that overlaps with the dipole acceptor light excitation spectrum. Thus, light emitted from the bioluminescent complex formed by the non-luminescent pair can excite the dipole acceptor moiety into an excited state if the dipole acceptor moiety is in sufficient proximity to the bioluminescent complex formed by the non-luminescent pair. In some aspects, the dipole acceptor moiety emits a detectable signal at a light emission spectrum (e.g., at one or more wavelengths within the light emission spectrum) that is different from the light emission spectrum of the bioluminescent complex formed by the non-luminescent pair. Thus, if an interaction element attached to the dipole acceptor moiety pairs with an interaction element attached to one or both of the non-luminescent elements, then the dipole acceptor moiety can accept energy from the bioluminescent complex and produce a detectable signal within a light emission spectrum.

In some aspects, a signal detected from the dipole acceptor moiety is increased (e.g., an absolute increase, as indicated for example by an absolute value of the detected signal) as compared to a comparable signal in which the dipole acceptor moiety is not in close proximity to a complexed non-luminescent pair (e.g., because of a lack of formation of a complex). Some aspects comprise detecting a ratio between a signal produced by the dipole acceptor moiety (e.g., area under the curve of the signal) and the signal produced by a complexed non-luminescent pair, or vice versa. Some aspects comprise comparing the ratio between (i) the detectable signal emitted by the dipole acceptor moiety: the detectable signal emitted by the bioluminescent complex formed by the non-luminescent pair when interaction elements attached to the dipole acceptor moiety or non-luminescent elements interact, e.g., in a complex and (ii) the detectable signal emitted by the dipole acceptor moiety:the detectable signal emitted by the bioluminescent complex formed by the non-luminescent pair when interaction elements attached to the dipole acceptor moiety or non-luminescent elements do not interact, e.g., before formation of a complex, or in conditions in which a complex does not form. In some aspects, protein interactions are determined based on the above ratios.

The signals can be detected by any suitable means. For instance, in some aspects the signals are detected sing a long-pass filter (e.g., in the case of the signal from the dipole acceptor moiety). In some aspects, the signals are detected using a band pass filter. In some aspects, the filters are suitable for detecting a BRET signal.

In certain aspects, the interaction pair or group comprises two or more molecules of interest (e.g., proteins of interest). For example, assays can be performed to detect the interaction of three or more molecules of interest by tethering each one to a separate member of a non-luminescent pair or a dipole acceptor moiety. If the molecules of interest interact (e.g., transiently interact, stably interact, etc.), then (i) the non-luminescent pair is brought into close proximity in a suitable conformation and a bioluminescent complex is formed (and bioluminescent signal is produced/detected (in the presence of substrate)) and (ii) the dipole acceptor moiety is brought into close proximity to the bioluminescent complex. In the absence of an interaction between the molecules of interest (e.g., no complex formation, not even transient interaction, etc.), then (i) the non-luminescent pair does not interact in a sufficient manner, and a bioluminescent signal is not produced or only weakly produced and/or (ii) the dipole acceptor moiety is not brought into close enough proximity to the bioluminescent complex to accept energy from the complex. Such aspects can be used to study the effect of inhibitors on complex formation, the effect of mutations on complex formation, the effect of conditions (e.g., temperature, pH, etc.) on complex formation, the interaction of a small molecule (e.g., potential therapeutic) with target molecules, etc.

Different non-luminescent pairs or groups may require different strength, duration and/or stability of the interaction complex to result in bioluminescent complex formation. In some aspects, a stable interaction complex is required to produce a detectable bioluminescent signal. In other aspects, even a weak or transient interaction complex results in bioluminescent complex formation. In some aspects, the strength or extent of an interaction complex is directly proportional to the strength of the resulting bioluminescent signal. Some non-luminescent pairs produce a detectable signal when combined with an interaction complex with a high millimolar dissociation constant (e.g., $K_d$>100 mM). Other non-luminescent pairs require an interaction pair with a low millimolar (e.g., $K_d$<100 mM), micromolar (e.g., $K_d$<1 mM), nanomolar (e.g., $K_d$<1 μM), or even picomolar (e.g., $K_d$<1 nM) dissociation constant in order to produce a bioluminescent complex with a detectable signal.

Different dipole acceptor moieties may require different strength, duration and/or stability of an interaction complex to result in acceptance of energy from a bioluminescent complex. In some aspects, a stable interaction complex is required to produce a detectable signal following acceptance of energy from a bioluminescent complex. In other aspects, even a weak or transient interaction complex results in acceptance of energy. In some aspects, the strength or extent of an interaction complex is directly proportional to the strength of the resulting signal. Some dipole acceptor moieties produce a detectable signal (e.g., a signal at a modified wavelength as compare to a signal without formation of an interaction complex) when combined with an interaction complex with a high millimolar dissociation constant (e.g., $K_d$>100 mM). Other non-luminescent pairs require an interaction pair with a low millimolar (e.g., $K_d$<100 mM), micromolar (e.g., $K_d$<1 mM), nanomolar (e.g., $K_d$<1 μM), or even picomolar (e.g., $K_d$<1 nM) dissociation constant in order to produce a detectable signal.

In some aspects, one or more of the non-luminescent peptides/polypeptides are not fragments of a pre-existing protein. In some aspects, one or more of the non-luminescent peptides/polypeptides are not fragments of a pre-existing bioluminescent protein. In some aspects, neither/none of the non-luminescent peptides/polypeptides are fragments of a pre-existing protein. In some aspects, neither/none of the non-luminescent peptides/polypeptides are fragments of a pre-existing bioluminescent protein. In some aspects, neither the non-luminescent peptide nor non-luminescent polypeptide that assemble together to form a bioluminescent complex are fragments of a pre-existing protein. In some aspects, a non-luminescent element for use in aspects of the present invention is not a subsequence of a preexisting protein. In some aspects, a non-luminescent pair for use in aspects described herein does not comprise complementary subsequences of a preexisting protein.

In some aspects, non-luminescent peptides/polypeptides are substantially non-luminescent in isolation. In certain aspects, when placed in suitable conditions (e.g., physiological conditions), non-luminescent peptides/polypeptides interact to form a bioluminescent complex and produce a bioluminescent signal in the presence of substrate. In other aspects, without the addition of one or more interaction elements (e.g., complementary interaction elements attached to the component non-luminescent peptide and non-luminescent polypeptide), non-luminescent peptides/polypeptides are unable to form a bioluminescent complex or only weakly form a complex. In such aspects, non-luminescent peptides/polypeptides are substantially non-luminescent in each other's presence alone, but produce significant detectable luminescence when aggregated, associated, oriented, or otherwise brought together by interaction elements. In some aspects, without the addition of one or more interaction elements (e.g., complementary interaction elements attached to the component peptide and polypeptide), peptides and/or polypeptides that assemble into the bioluminescent complex produce a low level of luminescence in each other's presence, but undergo a significant increase in detectable luminescence when aggregated, associated, oriented, or otherwise brought together by interaction elements.

Detectable signals from complexes formed from non-luminescent pairs or groups typically are in a light emission spectrum with lower wavelengths than the light emission spectrum of the dipole acceptor moiety. Exemplary light emission spectra associated with complexes formed from non-luminescent pairs include wavelengths of 500 nm or less, such as from about 350 nm to about 500 nm, or about 400 nm to about 480 nm, or about 450 nm to about 480 nm. Some aspects comprise detecting the detectable signal in the light emission spectrum, or a portion thereof.

In some aspects a light emission spectra is from with dipole donor element that is excited by within a light excitation spectrum. Such a dipole donor element does not necessarily require the complexation of non-luminescent pairs.

In some aspects, the dipole acceptor moiety is a fluorescent moiety, a dye, an arsenical protein label, a dye-protein conjugate pair, or a quantum dot. In some aspects, the fluorescent moiety is a fluorescent protein. A non-limiting list of exemplary fluorescent proteins is provided in Cranfill et al., "Quantitative Assessment of Fluorescent Proteins," Nat. Methods, 13(7): 557-562 (2016) (see, e.g., Supplementary Table 1), which is herein incorporated by reference in its entirety. Exemplary fluorescent proteins include EGFP, mEGFP, Emerald, mEmerald, sfGFP, mPapaya, YPet, Citrine, mCitrine, Venus, mVenus, Topaz, mTopaz, Clover, mClover, mNeonGreen, mOrange, mOrange2, CyOFP, mKO, mKO2, tdTomato, TagRFP, TagRFP-T, DsRed2, mRuby, mRuby2, mApple, mRFP1, mCherry, and FusionRed. In some aspects, the dipole acceptor moiety is a split dipole acceptor, e.g., with a first portion attached to a first interaction element and a second portion attached to a second interaction element.

In some aspects, the dipole acceptor moiety has an excitation spectrum (which can include peak excitation wavelengths that include any wavelength within the range, including the endpoints) of from about 380 nm to about 605 nm, such as about 383 to about 400 nm, about 434 to about 467 nm, about 396 to about 399 nm, about 483 to about 489 nm, about 504 to about 540 nm, about 547 to about 551 nm, about 554 to about 563 nm, about 558 to about 587 nm, or about 587 to about 604 nm. In some aspects, the dipole acceptor moiety has a light emission spectrum (which can include peak emission wavelengths that include any wavelength within the range, including the endpoints) of about 445 to about 700 nm, about 448 to about 454 nm, about 473 to about 492 nm, about 509 to about 511 nm, about 507 to about 510 nm, about 515 to about 540 nm, about 559 to about 565 nm, about 581 to about 584 nm, about 587 to about 610 nm, or about 623 to about 659 nm. In some aspects, the dipole acceptor moiety is a fluorescent protein that emits light at blue, cyan, UV-excitable green, green, yellow-green, orange, orange-red, red, or far-red wavelengths. Some aspects comprise detecting light emitted from the dipole acceptor moiety, e.g., by detecting emission in the light emission spectrum or a portion of the light emission spectrum. In some aspects, a detectable signal is emitted by the dipole acceptor moiety in its light emission spectrum. Some aspects comprise detecting the detectable signal, or a portion thereof.

In some aspects, compositions and methods described herein comprise one or more interaction elements. In a typical aspect, an interaction element is a moiety (e.g., peptide, polypeptide, protein, small molecule, nucleic acid, lipid, carbohydrate, etc.) that is attached to a peptide and/or polypeptide to assemble into the bioluminescent complex or a complex comprising the bioluminescent complex. The interaction element facilitates the formation of a complex by any suitable mechanism, including: interacting with one or both non-luminescent elements or dipole acceptor moiety, inducing a conformational change in a non-luminescent element, interacting with another interaction element (e.g., an interaction element attached to a non-luminescent element or a dipole acceptor moiety), bringing non-luminescent elements and/or a dipole acceptor moiety into close proximity, orienting non-luminescent elements and/or a dipole acceptor moiety for proper interaction, etc.

In some aspects, one or more interaction elements are added to a solution containing the non-luminescent elements and/or dipole acceptor moiety, but are not attached to the non-luminescent elements or dipole acceptor moiety. In such aspects, the interaction element(s) interact with the non-luminescent elements and/or dipole acceptor moiety to induce formation of the bioluminescent complex or create conditions suitable for formation of the bioluminescent complex that can donate energy to the dipole acceptor moiety. In some aspects, a single interaction element is attached to one member of a non-luminescent pair or to a dipole acceptor moiety. In some aspects, one interaction element is attached to each member of a non-luminescent pair and dipole acceptor moiety. Favorable interactions between the interaction elements facilitate interactions between the non-luminescent elements and dipole acceptor moiety. The interaction elements may stably interact, transiently interact, form a complex, etc. The interaction of the interaction elements facilitates interaction of the non-luminescent elements (and formation of a bioluminescent complex) and dipole acceptor moiety by any suitable mechanism, including, but not limited to: bringing the non-luminescent pair members and dipole acceptor moiety into close proximity, properly orienting the non-luminescent pair members and dipole acceptor moiety for interaction, reducing non-covalent forces acting against non-luminescent pair and dipole acceptor moiety interaction, etc.

In some aspects, an interaction group comprises any three chemical moieties that facilitate interaction of an associated non-luminescent pair and dipole acceptor moiety. An interaction group may include, for example: nucleic acids, polypeptides capable of multimerization (e.g., homomultimer, heteromultimer, etc.), proteins, ligands, small molecules, antibodies, epitopes, pairs of small molecules, etc. Any suitable group of interacting molecules may find use as an interaction group.

In some aspects, an interaction group comprises three or more molecules of interest (e.g., proteins of interest) or target molecules. In some aspects, compositions and methods herein provide useful assays (e.g., in vitro, in vivo, in situ, whole animal, etc.) for studying the interactions between a group of target molecules.

In certain aspects, a group of interaction elements, each attached to a non-luminescent elements or dipole acceptor moiety, interact with each other and thereby facilitate formation of the bioluminescent complex in close proximity to the dipole acceptor moiety. In some aspects, the presence of a ligand, substrate, co-factor or additional interaction element (e.g., not attached to non-luminescent element or dipole acceptor moiety) is necessary to induce the interaction between the interaction elements and facilitate complex formation. In some aspects, detecting a signal from the complex indicates the presence of the ligand, substrate, co-factor or additional interaction element or conditions that allow for interaction with the interaction elements. In some aspects, detecting a signal indicates a conformational change that alters the position of one or more interaction elements (e.g., in some aspects non-luminescent elements or dipole acceptor moiety can be attached to three or more interaction elements within a single molecule, and a conformational change within that molecule allows interaction between the interaction elements).

In some aspects, a pair of interaction elements, and a pair of non-luminescent elements are all present in a single amino acid chain (e.g., (interaction element 1)-NLpep-(interaction element 2)-NLpoly, NLpoly-(interaction element 1)-NLpep-(interaction element 2), NLpoly-(interaction element 1)-(interaction element 2)-NLpep, etc.). In some aspects in which a pair of interaction elements, and a pair of non-luminescent elements are all present in a single amino acid chain, a ligand, substrate, co-factor or addition interaction element is required for the interaction pair to form an interaction complex and facilitate formation of the bioluminescent complex.

In certain aspects, an interaction element and a non-luminescent element or dipole acceptor moiety are attached, fused, linked, connected, etc. In some aspects the non-luminescent element or dipole acceptor moiety is attached fused, linked, or connected to the N-terminus of the interaction moiety, or a molecule containing the interaction moiety. In some aspects the non-luminescent element or dipole acceptor moiety is attached fused, linked, or connected to the C-terminus of the interaction moiety, or a molecule containing the interaction moiety. In some aspects, a first non-luminescent element and a first interaction element are attached to each other, a second non-luminescent element and a second interaction element are attached to each other, and a third interaction element and a dipole acceptor moiety are attached to each other. Attachment of signal and interaction elements may be achieved by any suitable mechanism, chemistry, linker, etc. The interaction and non-luminescent elements or dipole acceptor moiety can be attached through covalent connection, but non-covalent linking of the two elements is also provided. In some aspects, the non-luminescent element, or dipole acceptor moiety, and interaction elements are directly connected and, in other aspects, they are connected by a linker.

In some aspects, in which the interaction element is a peptide or polypeptide, the signal and interaction elements can be contained within a single amino acid chain. In some aspects, a single amino acid chain comprises, consists of, or consists essentially of a non-luminescent element and an interaction element, or a dipole acceptor moiety and an interaction element. In some aspects, a single amino acid chain comprises, consists of, or consists essentially of a non-luminescent element, an interaction element, and optionally one or more an N-terminal sequence, a C-terminal sequence, regulatory elements (e.g., promoter, translational start site, etc.), and a linker sequence. In some aspects, a single amino acid chain comprises, consists of, or consists essentially of a dipole moiety acceptor, an interaction element, and optionally one or more an N-terminal sequence, a C-terminal sequence, regulatory elements (e.g., promoter, translational start site, etc.), and a linker sequence. In some aspects, the signal and interaction elements are contained within a fusion polypeptide. The signal and interaction elements (and any other amino acid segments to be included in the fusion) may be expressed separately; however, in other aspects, a fusion protein is expressed that comprises or consist of both the interaction and signal sequences.

In some aspects, a first fusion protein comprising a first non-luminescent element and first interaction element, a second fusion protein comprising a second non-luminescent element and second interaction element, and a third fusion protein comprising a dipole acceptor moiety and a third interaction element are expressed within the same cells (the terms "first," "second," and "third" in this context are arbitrary, e.g., the fusion protein comprising the dipole acceptor moiety can also be considered the "first" fusion protein, etc.). In some aspects, the first, second, and third fusion proteins are purified and/or isolated from the cells, or the interaction of the fusion proteins is assayed within the cells. In some aspects, the first, second, and third fusion proteins are expressed in separate cells and combined (e.g., following purification and/or isolation, or following fusion of the cells or portions of the cells, or by transfer of a fusion protein from one cell to another, or by secretion of one or more fusion proteins into the extracellular medium) for signal detection. In some aspects, one or more fusion proteins are expressed in cell lysate (e.g., rabbit reticulocyte lysate) or in a cell-free system. In some aspects, one or more fusion proteins are expressed from the genome of a virus or other cellular pathogen.

In certain aspects, nucleic acids, DNA, RNA, vectors, etc. are provided that encode peptide, polypeptides, fusion polypeptide, fusion proteins, etc. Such nucleic acids and vectors may be used for expression, transformation, transfection, injection, etc.

In some aspects, a non-luminescent element and an interaction element, and/or a dipole acceptor moiety and an interaction element, are connected by a linker. In some aspects, a linker connects the non-luminescent and/or dipole acceptor moiety with the interaction element while providing a desired amount of space/distance between the elements. In some aspects, a linker allows both the non-luminescent and interaction elements, and/or dipole acceptor moiety and interaction element, to form their respective pairs (e.g., non-luminescent pair and interaction pair) simultaneously. In some aspects, a linker assists the interaction element in facilitating the formation of a non-luminescent pair interaction, or a dipole acceptor moiety/bioluminescent complex interaction. In some aspects, when an interaction pair or group is formed, the linkers that connect each non-luminescent element or dipole acceptor moiety to their respective interaction elements position the non-luminescent elements/dipole acceptor moiety at the proper distance and conformation to form a bioluminescent complex that transfers resonance energy to the dipole moiety acceptor. In some aspects, an interaction element and non-luminescent element, and/or the dipole acceptor moiety and interaction element, are held in close proximity (e.g., <4 monomer units) by a linker. In some aspects, a linker provides a desired amount of distance (e.g., 1, 2, 3, 4, 5, 6 . . . 10 . . . 20, or more monomer units) between signal and interaction elements (e.g., to prevent undesirable interactions between signal and interaction elements, for steric considerations, to allow proper orientation of non-luminescent elements upon formation of an interaction complex, to allow propagation of a complex-formation from interaction complex to non-luminescent elements, etc.). In certain aspects, a linker provides appropriate attachment chemistry between the signal and interaction elements. A linker may also improve the synthetic process of making the signal and interaction element (e.g., allowing them to be synthesized as a single unit, allowing post synthesis connection of the two elements, etc.).

In some aspects, a linker is any suitable chemical moiety capable of linking, connecting, or tethering an interaction element to a non-luminescent element or dipole acceptor moiety. In some aspects, a linker is a polymer of one or more repeating or non-repeating monomer units (e.g., nucleic acid, amino acid, carbon-containing polymer, carbon chain, etc.). When a non-luminescent element, or dipole acceptor element, and interaction element are part of a fusion protein, a linker (when present) is typically an amino acid chain. When a non-luminescent element, or dipole acceptor moiety, and interaction element are tethered together after the expression of the individual elements, a linker may comprise any chemical moiety with functional (or reactive) groups at either end that are reactive with functional groups on the signal and interaction elements, respectively. Any suitable moiety capable of tethering the signal and interaction elements may find use as a linker.

A wide variety of linkers may be used. In some aspects, the linker is a single covalent bond. In some aspects, the linker comprises a linear or branched, cyclic or heterocyclic, saturated or unsaturated, structure having 1-20 nonhydrogen atoms (e.g., C, N, P, O and S) and is composed of any combination of alkyl, ether, thioether, imine, carboxylic, amine, ester, carboxamide, sulfonamide, hydrazide bonds and aromatic or heteroaromatic bonds. In some aspects, linkers are longer than 20 nonhydrogen atoms (e.g. 21 non-hydrogen atoms, 25 non-hydrogen atoms, 30 non-hydrogen atoms, 40 non-hydrogen atoms, 50 non-hydrogen atoms, 100 non-hydrogen atoms, etc.) In some aspects, the linker comprises 1-50 non-hydrogen atoms (in addition to hydrogen atoms) selected from the group of C, N, P, O and S (e.g. 1, 2, 3, 4, 5, 6, 7, 8, 9, 10, 1, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 non-hydrogen atoms).

The described aspects are not limited by the types of linkers available. The signal and interaction elements can be linked, either directly (e.g. linker consists of a single covalent bond) or linked via a suitable linker. The described aspects are not limited to any particular linker group. A variety of linker groups are contemplated, and suitable linkers could comprise, but are not limited to, alkyl groups, methylene carbon chains, ether, polyether, alkyl amide linker, a peptide linker, a modified peptide linker, a Poly (ethylene glycol) (PEG) linker, a streptavidin-biotin or avidin-biotin linker, polyaminoacids (e.g. polylysine), functionalised PEG, polysaccharides, glycosaminoglycans, dendritic polymers (WO93/06868 and by Tomalia et al, in Angew. Chem. Int. Ed. Engl. 29:138-175 (1990), herein incorporated by reference in their entireties), PEG-chelant polymers (W94/08629, WO94/09056 and WO096/26754, herein incorporated by reference in their entireties), oligonucleotide linker, phospholipid derivatives, alkenyl chains, alkynyl chains, disulfide, or a combination thereof. In some aspects, the linker is cleavable (e.g., enzymatically (e.g., TEV protease site), chemically, photoinduced, etc.)

In some aspects, substantially non-luminescent peptides and polypeptides are provided with less than 100% sequence identity and/or similarity to any portion of an existing luciferase (e.g., a firefly luciferase, a Renilla luciferase, an Oplophorus luciferase, enhanced Oplophorus luciferases as described in U.S. 2010/0281552 and U.S. 2012/0174242, herein incorporated by reference in their entireties). Some aspects involve the formation of bioluminescent complexes of non-luminescent peptides and polypeptides with less than 100% sequence identity with all or a portion (e.g., 8 or more amino acids, less than about 25 amino acids for peptides) of NANOLUC® Luciferase (e.g., SEQ ID NO:1):
MVFTLEDFVGDWRQTAGY-
NLDQVLEQGGVSSLFQNLGVSVTPIQRIVLS-
GENGLKIDIHVIIP YEGLSGDQMGQIEKIFKVVYPVD-
DHHFKVILHYGTLVIDGVTPNMIDYFGRPYEGIAVFD
GK KITVTGTLWNGNKIIDERLINPDGSLL-
FRVTINGVTGWRLCERILA Certain aspects of the present invention involve the formation of bioluminescent complexes of non-luminescent peptides and polypeptides with less than 100%, but more than 40% (e.g., >40%, >45%, >50%, >55%, >60%,>65%, >70%, >75%, >80%, >85%, >90%, >95%, >98%, >99%) sequence identity with all or a portion (e.g., 8 or more amino acids, less than about 25 amino acids for peptides) of NANOLUC® Luciferase. In some aspects, non-luminescent peptides and polypeptides are provided with less than 100% sequence similarity with a portion (e.g., 8 or more amino acids, less than about 25 amino acids for peptides) of SEQ ID NO: 1 (e.g., peptides and polypeptides that interact to form bioluminescent complexes). In some aspects, non-luminescent peptides and polypeptides are provided with less than 100%, but more than 40% (e.g., >40%, >45%, >50%, >55%, >60%, >65%, >70%, >75%, >80%,>85%, >90%, >95%, >98%, >99%) sequence similarity with a portion (e.g., 8 or more amino acids, less than about 25 amino acids for peptides) of SEQ ID NO: 1 (e.g., peptides and polypeptides that interact to form bioluminescent complexes). Non-luminescent peptides are provided that have less than 100% sequence identity and/or similarity with about a 25 amino acid or less portion of SEQ ID NO: 1, wherein such peptides form a bioluminescent complex when combined under appropriate conditions (e.g., stabilized by an interaction pair) with a polypeptide having less than 100%, but more than 40% (e.g., >40%, >45%, >50%, >55%, >60%, >65%, >70%, >75%, >80%, >85%, >90%, >95%, >98%,>99%) sequence identity and/or similarity with another portion SEQ ID NO: 1. Non-luminescent peptides are provided that have less than 100% sequence identity and/or similarity with about a 25 amino acid or less portion of SEQ ID NO: 1, wherein such peptides form a bioluminescent complex when combined under appropriate conditions (e.g., stabilized by an interaction pair) with a polypeptide having less than 100%, but more than 40% (e.g., >40%, >45%, >50%, >55%, >60%, >65%,>70%, >75%, >80%, >85%, >90%, >95%, >98%, >99%) sequence identity and/or similarity with another portion SEQ ID NO: 1. Non-luminescent peptides are provided that have less than 100%, but more than 40% (e.g., >40%, >45%,>50%, >55%, >60%, >65%, >70%, >75%, >80%, >85%, >90%, >95%, >98%, >99%) sequence identity and/or similarity with about a 25 amino acid or less portion of SEQ ID NO: 1, wherein such peptides form a bioluminescent complex when combined under appropriate conditions (e.g., stabilized by an interaction pair) with a polypeptide having less than 100%, but more than 40% (e.g., >40%, >45%, >50%, >55%, >60%, >65%, >70%, >75%, >80%, >85%,>90%, >95%, >98%, >99%) sequence identity and/or similarity with another portion SEQ ID NO: 1. Similarly, non-luminescent polypeptides are provided that have less than 100%, but more than 40% (e.g., >40%, >45%, >50%, >55%,>60%, >65%, >70%, >75%, >80%, >85%, >90%, >95%, >98%, >99%) sequence identity or similarity with a portion of SEQ ID NO: 1, wherein such polypeptides form a bioluminescent complex when combined under appropriate conditions (e.g., stabilized by an interaction pair) with a peptide having less than 100%, but optionally more than 40% (e.g., >40%, >45%, >50%, >55%, >60%, >65%, >70%, >75%, >80%, >85%, >90%, >95%, >98%, >99%) sequence identity and/or similarity with another portion SEQ ID NO: 1.

In some aspects, non-luminescent peptides that find use in aspects of the present invention include peptides comprising one or more of amino acid sequences of Table 1 of US 2018/0313825, which is herein incorporated by reference in its entirety, and nucleic acids coding for the peptide sequences of Table 1 of US 2018/0313825.

In some aspects, a non-luminescent peptide or polypeptide and/or an interaction element and/or a dipole acceptor moiety, comprises a synthetic peptide, peptide containing one or more non-natural amino acids, peptide mimetic, or conjugated synthetic peptide (e.g., conjugated to a functional group (e.g., fluorophore, luminescent substrate, etc.)).

Also provided are compositions and methods that are useful in a variety of fields including basic research, medical research, molecular diagnostics, etc. Although the reagents and assays described herein are not limited to any particular applications, and any useful application should be viewed as being within the scope of the present invention, the following are exemplary assays, kits, fields, experimental set-ups, etc. that make use of the presently claimed invention.

Some applications that make use of aspects of the present invention involve the monitoring/detection of protein multimerization (e.g., heteromultimers, homomultimers), protein-protein interactions, protein-RNA interactions, protein-DNA interactions, nucleic acid hybridization, protein-small molecule interactions, or any other combinations of molecular entities. A first entity of interest can be attached to a first member of a non-luminescent pair, a second entity of interest can be attached to the second member of a non-luminescent pair, and a third entity of interest can be attached to a dipole acceptor moiety. If a detectable signal from the non-luminescent pair is produced under the particular assay conditions, then interaction of the first and second entities is inferred. A detectable signal from the dipole acceptor moiety can then indicate interaction between the first, second, and third entities. Such assays are useful for monitoring molecular interactions under any suitable conditions (e.g., in vitro, in vivo, in situ, whole animal, etc.), and find use in, for example, drug discovery, elucidating molecular pathways, studying equilibrium or kinetic aspects of complex assembly, high throughput screening, proximity sensor, etc.

In some aspects, a non-luminescent pair of known characteristics (e.g., spectral characteristics, mutual affinity of pair) is used to elucidate the affinity of, or understand the interaction of, an interaction pair of interest. In some aspects, a well-characterized interaction pair is used to determine the characteristics (e.g., spectral characteristics, mutual affinity of pair) of a non-luminescent pair. In some aspects, a dipole acceptor moiety of known characteristics (e.g., spectral characteristics) is used to elucidate the affinity of, or understand the interaction of, an interaction group of interest. In some aspects, a well-characterized interaction group is used to determine the characteristics (e.g., spectral characteristics) of a dipole acceptor moiety.

Aspects described herein may find use in drug screening and/or drug development. For example, the interaction of a small molecule drug or an entire library of small molecules with target proteins (e.g., complex) of interest (e.g., therapeutic target) is monitored under one or more relevant conditions (e.g., physiological conditions, disease conditions, etc.). In other aspects, the ability of a small molecule drug or an entire library of small molecules to enhance or inhibit the interactions between multiple entities (e.g., complexes involving a receptor and ligand, multi-protein interactions, etc.) is assayed. In some aspects, drug screening applications are carried out in a high through-put format to allow for the detection of the binding of tens of thousands of different molecules to a target, or to test the effect of those molecules on the binding of other entities.

In some aspects, the present invention provides the detection of molecular interactions in living organisms (e.g., bacteria, yeast, eukaryotes, mammals, primates, human, etc.) and/or cells. In some aspects, fusion proteins comprising signal and interaction (target) polypeptides are coexpressed in the cell or whole organism, and signal is detected and correlated to the formation of the interaction complex. In some aspects, cells are transiently and/or stably transformed or transfected with vector(s) coding for signal element(s), interaction element(s), fusion proteins (e.g., comprising a signal and interaction element), etc. In some aspects, transgenic organisms are generated that code for the necessary fusion proteins for carrying out the assays described herein. In other aspects, vectors are injected into whole organisms. In some aspects, a transgenic animal or cell (e.g., expressing a fusion protein) is used to monitor the biodistribution of a small molecule or a biologic tethered (e.g., conjugated or genetically fused) to NLpeptide sequence that would form a complex in the subcellular compartments and/or tissues where it concentrates.

In some aspects, drugs are designed to promote or disfavor GPCR-mediated formation of Gαi-βarr complexes to enhance the therapeutic benefit of drugs for a large variety of diseases since GPCRs are the target of ~30% of FDA-approved medications. For some examples, opioids, antipsychotics, anti-depressants, anti-hypertensives, diabetic medications, inflammatory skin diseases, cancers, stem cell reprogramming, and drug abuse treatment could all be treatment modalities for disorders that could be treated by drugs targeting the Gαi-βarr complexes.

In some aspects, a peptide (e.g., non-luminescent peptide or dipole acceptor moiety) portion of a complex is employed as a protein tag (e.g., within cells). In such aspects, a polypeptide (e.g., non-luminescent peptide or dipole acceptor moiety) portion of a complex (e.g., capable of forming a luminescent complex with the non-luminescent peptide) is applied to cells (e.g., as part of a reagent) to detect/quantify the presence of proteins tagged with the non-luminescent peptide. For example, a protein of interest is fused to a high affinity NLpep (e.g., NLpep86). The NLpep is then transfected into cells of interest, a reagent containing NanoGlo+ NLpoly11S is then added to cells+media, and luminescence is detected. In some aspects, the small size of the peptide is useful for protein tagging. In some aspects, non-luminescent polypeptides and/or dipole acceptor moiety used in such a system are stable enough to exist in a suitable buffer for extended periods of time (e.g., in the presence of the furimazine substrate). In certain aspects, the non-luminescent polypeptide has minimal detectable luminescence in the absence of the complementing peptide (e.g., even in the presence of furimazine substrate). In some aspects, optimized buffer conditions are utilized to meet criteria necessary for protein tagging. High affinity spontaneously polypeptides and peptides are useful in such systems, and have utility in, for example, immunoassays, detection of virus particles, the study of protein dynamics in living cells, etc. In some aspects, such a system provides a small protein tag (e.g., 11 amino acids) providing high sensitivity detection, stability (e.g., particularly under denaturing conditions), and/or a broad dynamic range.

The compositions and methods provided herein, as well as any techniques or technologies based thereon find use in a variety of applications and fields. A non-limiting list of example applications follows. In each example, the technique will involve at least two non-luminescent elements and at least one dipole acceptor moiety element, each of which can independently be attached to a first, second, or third peptide or polypeptide. Antibody-free Western Blot: For example, first peptide or polypeptide (e.g., a protein of interest) is created (e.g., by genetic engineering) and expressed by any suitable means. The proteins can be separated (e.g., by PAGE) and transferred to a membrane. The membrane can then be washed with a second and third peptide or polypeptide (e.g. including a complimentary non-luminescent element, thus allowing a luminescent complex to form, and a dipole acceptor moiety, allowing a larger complex to form) and placed on imager (e.g., utilizing a CCD camera) with Furimazine (PBI-3939) atop the membrane, and the protein(s) of interest are detected (e.g., via the luminescence of the complex). "LucCytochemistry": For example, a first peptide or polypeptide (e.g., protein of interest is expressed fused to a non-luminescent peptide or polypeptide, or a dipole acceptor moiety) is prepared, and then detected with a luminescence following complexing to a second and third peptide or polypeptide in a fashion analogous to immunocytochemistry. Protein localization assay: For example, a localization signal is added to a first and/or second peptide or polypeptide (e.g., via genetic engineering) and expressed in cells (e.g., a nuclear localization signal added would result in expression of the polypeptide in the nucleus). A second and/or third peptide or polypeptide is created (e.g., via genetic engineering) and expressed in cells with the first and/or second peptide or polypeptide. Luminescence is produced if the proteins of interest localizes in the same subcellular compartment (e.g., the nucleus) as the signal-localized polypeptides. Protein Stability Assay: For example, a first peptide or polypeptide is incubated under one or more conditions of interest. A second and/or third peptide or polypeptide is added (e.g., at various time points), and luminescence is used to quantify the amount of protein of interest (e.g., a proxy for stability). Protein Detection/Quantification: For example, a first peptide or polypeptide is prepared and expressed and/or manipulated by any method. The second and third peptides or polypeptides are then added to detect and/or quantify the protein of interest. Protein Purification: For example, first and/or second peptide or polypeptide is expressed by any method. The mixture of proteins is passed through immobilized second and/or third polypeptides or peptides (e.g., on beads, on a column, on a chip, etc.), washed with suitable buffer and eluted (e.g., with a buffer of high ionic strength or low pH). A mutant form of the peptide or polypeptide that does not activate the luminescence of the complex may be used to elute the protein of interest. Pull-down: For example, an immobilized first and/or second peptide or polypeptide is used to isolate a protein of interest (and interacting proteins) that is a second and/or third peptide or polypeptide of interest. G-Coupled Protein Receptor (GPCR) Internalization Assay: For example, a first peptide or polypeptide is fused to a GPCR of interest (e.g., via genetic engineering) and expressed on the surface of cells. A second and third polypeptide or peptide are added to the media of the cells and used to detect the GPCR on cell surface. A ligand is added to stimulate the internalization of the GPCR, and a decrease in luminescence is observed. Membrane Integrity Assay for Cell Viability: For example, when the cell membrane of a cell expressing a first peptide or polypeptide becomes compromised, the first peptide or polypeptide enters the cell (e.g., a peptide that otherwise can't cross the cell membrane), thereby forming a luminescent complex, and generating luminescence. 5-Hydroxymethyl Cytosine Detection: For example, a cysteine is added to a first peptide or polypeptide and incubated with DNA and a methyltransferase. The methyltransferase catalyzes the addition of the thiol (cysteine) only onto cytosine residues that are 5-hydroxymethylated. Unincorporated peptide is then separated from the DNA (using any method possible), and a second and third peptide or polypeptide are added to detect the peptide conjugated to the DNA. Formyl Cytosine Detection:

For example, similar to the 5-hydroxymethyl cytosine detection above, this detection method uses chemistry with specific reactivity for formyl cytosine. Viral Incorporation: Nucleic acid coding for a first peptide or polypeptide is incorporated into a viral genome, and the second and third polypeptide or peptide are constitutively expressed in the target cells. Upon infection of the target cells and expression of the first peptide or polypeptide, the bioluminescent complex forms and a signal is detected (e.g., in the presence of substrate). Chemical Labeling of Proteins. A first peptide or polypeptide is fused or tethered to a reactive group (e.g., biotin, succinimidyl ester, maleimide, etc.). A protein(s) of interest (e.g., antibody) is tagged with the first peptide or polypeptide through binding of the reactive group to the protein of interest. Second and third peptide or polypeptides are added to the system, and a luminescent complex is produced upon binding to the polypeptide to the peptide. Protease Assay: For example, a peptide sequence that is recognized by a protease of interest can be joined to NLPep in such a way that prevents bioluminescence upon exposure to NLPoly. Ways to do this include attaching a luminescence quencher to the protease recognition sequence or binding the protease recognition sequence to NLPep in such a way that complementation is hindered. Upon activity of the protease to cleave the recognition sequence, the ability of NLPoly to complement to NLPep and emit luminescence is restored, and thus the system is a sensitive protease assay. RNA detection. Biomolecule Linker characterization: For example, a linker attached to a biomolecule such as an antibody and can be evaluated for its stability under a set of conditions through attaching NLPep to the molecule via the linker of interest. Over time, the production of free NLPep through linker degradation can be monitored by addition of NLPoly and furimazine and quantification of bioluminescence produced. Mutation assay: For example, a point mutation, a frameshift mutation, etc. introduced in vitro or in vivo results in either a gain of signal or loss of signal from a luminescent complex. Such an assay could be used, for example, to test compounds for mutagenicity. Target engagement for peptide inhibitors: Use of low affinity NLpep-conjugated peptides (expressed in cells) to monitor target engagement of peptide-based inhibitors. NLpoly is tethered to the target of interest. Engagement results in loss of signal from luminescent complex. Gain of signal Protease biosensors: A protease cleavage site is expressed between NLpoly and a dark peptide NLpep (low affinity). Cleavage releases dark peptide allowing for high affinity NLpep to complement NLpoly. Gain of function protease assay: The sequence of an NLpep is engineered proximal to a cleavage site of a full length substrate for a protease (e.g., caspase, ADAM, etc). The peptide remains sterically inaccessible as long as the substrate remains intact and the peptide is "buried". Both the genetically engineered protease substrate and a NLpoly (e.g., NLpoly11S) are co-transfected into a target cell line. Luciferase activity is induced upon induction of protease activity which leads to the cleavage of the substrate and exposure of the activator peptide on the N- or C-terminus of one of the fragments. This principle is expandable to detect conformational changes and/or protein modifications as well. Intracellular analyte quantification using recombinant intrabodies: Antibody fragments expressed within cells as NLpoly or NLpep fusion. Complementary subunit is genetically fused to an analyte of interest. When analyte is present, antibody binds and luminescent complex is formed. The application is expandable to intracellular PTM (e.g. phosphorylation) biosensors, in which the intrabody only binds to the analyte when it has been phosphorylated (or otherwise bound by the modification-specific Ab). The above applications of the compositions and methods of the present invention are not limiting and may be modified in any suitable manner while still being within the scope of the present invention.

The present invention also provides methods for the design and/or optimization of non-luminescent pairs/groups and the bioluminescent complexes that form therefrom. Any suitable method for the design of non-luminescent pairs/groups that are consistent with aspects described herein, and/or panels thereof, is within the scope of the present invention.

In certain aspects, non-luminescent pairs/groups are designed de novo to lack luminescence individually and exhibit luminescence upon association. In such aspects, the strength of the interaction between the non-luminescent elements is insufficient to produce a bioluminescent signal in the absence of interaction elements to facilitate formation of the bioluminescent complex.

In other aspects, non-luminescent elements and/or non-luminescent pairs are rationally designed, for example, using a bioluminescent protein as a starting point. For example, such methods may comprise: (a) aligning the sequences of two or more related proteins; (b) determining a consensus sequence for the related proteins; (c) providing first and second fragments of a bioluminescent protein that is related to the ones from which the consensus sequence was determined, wherein the fragments are individually substantially non-luminescent but exhibit luminescence upon interaction of the fragments; (d) mutating the first and second fragments at one or more positions each (e.g., in vitro, in silico, etc.), wherein said mutations alter the sequences of the fragments to be more similar to a corresponding portion of the consensus sequence, wherein the mutating results in a non-luminescent pair that are not fragments of a preexisting protein, and (e) testing the non-luminescent pair for the absence of luminescence when unassociated and luminescence upon association of the non-luminescent pair. In other aspects, first and second fragments of one of the proteins used in determining the consensus sequence are provided, mutated, and tested.

In some aspects, a peptide of a luminescent pair is a "dark peptide" or one that binds to its complement (e.g., NLpoly) (e.g., with low or high affinity) but produces minimal or no luminescence. In some aspects, a high affinity dark peptide finds use in inverse complementation, or gain of signal assays for measuring inhibitors. In some aspects, a low affinity dark peptide is used to bring down background of NLpoly11S in a reagent for the detection of a high affinity peptide tag (e.g. NLpep86).

In some aspects, a peptide of a luminescent pair is a "quencher peptide," or one that contains a quencher moiety (e.g., DAB), and the quencher absorbs the light/energy produced by both a NLpoly in isolation (e.g., the signal produced independent of a complementing NLpep) and a NLpoly-NLpep complex (e.g., the signal produced as a result of complex formation). Exemplary dark quencher peptides would have a suitable absorption spectrum and include DAB-161, DAB-162, DAB-163, DAB-164, DAB-165, and DAB-166; wherein DAB=Dabcyl (475 nm quencher)+dPEG4 spacer.

In some aspects, the above methods are not limited to the design and/or optimization of signal pairs or groups. The same steps are performed to produce pairs or groups of elements that lack a given functionality (e.g., enzymatic activity) individually, but display such functionality when associated. In any of these cases, the strength of the interaction between the signal elements may be altered via mutations to ensure that it is insufficient to produce functionality in the absence of interaction elements that facilitate formation of the bioluminescent complex.

The following examples are included as illustrative of the compositions and methods described herein. The examples are in no way intended to limit the scope of the invention. Other aspects will be apparent to those skilled in the art.

EXAMPLES

Example 1: Materials and Methods

Cell Culture and Transfection

Human embryonic kidney cells (HEK 293, HEK 293T, Rockman βarrestin-1/2 HEK 293 knockout, triple $G_\alpha$ subfamily knockout ('Δ3G') HEK 293, and quadruple Gα subfamily knockout ('total G') HEK 293) were maintained in minimum essential medium supplemented with 1% anti-anti and 10% fetal bovine serum. Cells were grown at 37° C. with humidified atmosphere of 5% $CO_2$. For BRET and luminescence studies, HEK 293T cells were transiently transfected via an optimized calcium phosphate protocol. For immunoblot studies utilizing siRNA, 'Δ3G' or 'total G' HEK 293, cells were transiently transfected with LIPOFECTAMINE® 3000 (Thermo Fisher) or RNAIMAX™ (Thermo Fisher) according to manufacturer specifications. For TGF alpha shedding assay studies, 'Δ3G' HEK 293 cells were transfected using FUGENE® 6 (Promega) or LIPOFECTAMINE® 2000 (Thermo Fisher) according to manufacturer specifications.

Generation of Constructs

Cloning of constructs was performed using conventional techniques such as restriction enzyme/ligation methods. Linkers between the fluorescent proteins or luciferases and the cDNAs for receptors, transducers, kinases, or adaptor proteins were flexible (GGGGS) and ranged between 15-18 amino acids. CXCR3 C-terminus phosphomutant constructs were generated using a QUIKCHANGE™ mutagenesis kit (Agilent, Santa Clara, Calif.). The constructs used are set forth in Table 1 below:

TABLE 1

Constructs Used

| Name | Main Component | Addition 1 | Addition 2 | N-term Linker | C-term Linker |
|---|---|---|---|---|---|
| V2R | human vasopressin 2 receptor | N-term 3xHA-tag | | | |
| β2AR | human beta 2 adrenergic receptor | N-term 3xHA-tag | | | |
| D1R | mouse dopamine d1 receptor | N-term 3xHA-tag | | | |
| D2R | mouse dopamine d2 receptor | N-term 3xHA-tag | | | |
| CXCR3 | human C-X-C motif chemokine receptor 3 | | | | |
| AT1R | human angiotensin II receptor type 1 | N-term 3xHA-tag | | | |
| AT1R-RlucII | human angiotensin II receptor type 1 | N-term 3xHA-tag | C-term RlucII | | |
| V2R-LgBiT | human vasopressin 2 receptor | N-term 3xHA-tag | C-term LgBiT | | TGGGGSGGGGSGGGGS |
| V2R-SmBiT | human vasopressin 2 receptor | N-term 3xHA-tag | C-term SmBiT | | TGGGGSGGGGSGGGGS |
| β2AR-LgBiT | human beta 2 adrenergic receptor | N-term 3xHA-tag | C-term LgBiT | | TGGGGSGGGGSGGGGS |
| SmBiT-βarr2 | mouse beta-arrestin 2 | N-term SmBiT | | GTGGGGSGGGGSGGGGS | |
| SmBiT-βarr1 | rat beta-arrestin 1 | N-term SmBiT | | GTGGGGSGGGGSGGGGS | |
| LgBiT-GNAS | human stimulatory G protein | LgBiT | | | |
| LgBiT-GNAI1 | human inhibitory G protein 1 | LgBiT | | | |
| LgBiT-GNAI1 C352I | human inhibitory G protein 1 C352I | LgBiT | | | |

TABLE 1-continued

Constructs Used

| Name | Main Component | Addition 1 | Addition 2 | N-term Linker | C-term Linker |
|---|---|---|---|---|---|
| LgBiT-GNAI2 | human inhibitory G protein 2 | LgBiT | | | |
| LgBiT-GNAI3 | human inhibitory G protein 3 | LgBiT | | | |
| LgBiT-GNAQ | human Gq protein | LgBiT | | | |
| LgBiT-GNA12 | human G12 protein | LgBiT | | | |
| V2R-mKO | human vasopressin 2 receptor | N-term 3xHA-tag | C-term mKO | | SDPGG |
| β2AR-mKO | human beta 2 adrenergic receptor | N-term 3xHA-tag | C-term mKO | | SDPGG |
| βarr2-mKO | mouse beta-arrestin 2 | C-term mKO | | | RARDPPVAT |
| βarr2-YFP | mouse beta-arrestin 2 | C-term YFP | | | Caron Lab Stocks |
| βarr2-RLucII | mouse beta-arrestin 2 | C-term RlucII | | | RARDPPARAT |
| Erk2-mKO | rat extracellular regulated kinase 2 (Erk2) | C-term mKO | | | SDPGG |
| mKO-Erk2 | rat extracellular regulated kinase 2 (Erk2) | N-term mKO | | QAS | |
| mKO | monomeric kusabira orange (cytosolic) | | | | |
| GNAI1-GFP | human inhibitory G protein 1 | GFP | | | |
| FLAG-βarr1 | rat beta-arrestin 1 | FLAG tag | | | |
| Mars1-V2R | human vasopressin 2 receptor | Mars1 | | | |
| GNAI1-mVenus | human inhibitory G protein 1 | mVenus | | | |

Split Luciferase and Complex BRET Assays

HEK293T cells seeded in 6-well plates were co-transfected with 500 ng of smBiT tagged β-arrestin-2, and either 250 ng of LgBiT tagged receptor or 2000 ng of untagged receptor and varying concentrations of LgBiT Gα protein expression vector (most experiments were conducted between 50-200 ng of Gα plasmid) or 2000 ng of mKO tagged β-arrestin-2 and 500 ng of smBiT tagged V2R using a calcium phosphate protocol. Twenty-four hours post-transfection, cells were plated onto clear bottom, white-walled 96-well plates at 50,000-100,000 cells/well in "BRET media"—clear minimum essential medium (GIBCO) supplemented with 2% FBS, 10 mM HEPES, 1×GLUTAMAX™, and 1× Anti-Anti (GIBCO). Select cells were then treated overnight with pertussis toxin pretreatment at a final concentration of 200 ng/mL. The following day, media were removed, and cells were incubated at room temperature with 80 μL of Hanks' balanced salt solution (GIBCO) supplemented with 20 mM HEPES and 3 μM coelenterazine-h for 15 minutes. For luminescence split luciferase studies, plates were read with a BioTek SYN-ERGY™ Neo2 plate reader set at 37° C. with a 485 nm emission filter. Cells were stimulated with either vehicle (Hank's Balanced Salt Solution with 20 mM HEPES) or indicated concentration of agonist. For split luciferase luminescence experiments, plates were read both before and after ligand treatment to calculate Δnet change in luminescence and subsequently normalized to vehicle treatment. For complex BRET experiments, plates were read on a Berthold Mithras LB940 using pre-warmed media and instrument at 37° C. using a standard Rluc emissions filter (480 nm) with a custom mKO 542 nm long-pass emission filter (Chroma Technology Co., Bellows Falls, Vt.). Readings were performed using a kinetic protocol with injection of ligands as indicated in figures. The BRET ratio was calculated by dividing the mKO signal by the luciferase signal.

For some experiments, a Net BRET ratio was calculated by subtracting the vehicle BRET ratio from the ligand stimulated BRET ratio, or an adjusted BRET ratio was calculated by subtracting the ligand treated cytosolic mKO signal from the ligand treated effector mKO signal.

Immunoblotting

Cells were serum starved for at least four hours, stimulated with the indicated ligand, subsequently washed 1× with ice-cold PBS, lysed in ice-cold RIPA buffer containing phosphatase and protease inhibitors (Phos-STOP (Roche), Complete EDTA free (Sigma)) and rotated for forty-five minutes, and cleared of insoluble debris by centrifugation at >12,000×g (4° C., 15 minutes), after which the supernatant was collected. Protein was resolved on SDS-10% polyacrylamide gels, transferred to nitrocellulose membranes, and immunoblotted with the indicated primary antibody overnight (4° C.). Phospho-ERK (Cell Signaling Technology, #9106) and total ERK (Millipore #06-182) were used to assess ERK activation. A1-CT antibody that recognizes both isoforms of β-arrestin was utilized, with protein loading assessed by alpha-tubulin (Sigma #T6074). Galpha i-1 (13533, Santa Cruz Biotechnology), Galpha q/11/14 (365906, Santa Cruz Biotechnology), Galpha 12 (515445, Santa Cruz Biotechnology), Galpha 13 (293424, Santa Cruz Biotechnology), Galpha s/olf (55545, Santa Cruz Biotechnology) antibodies were used to verify 'Δ3G' HEK 293 cells.

Horseradish peroxidase-conjugated polyclonal mouse anti-rabbit-IgG or anti-mouse-IgG were used as secondary antibodies. Immune complexes on nitrocellulose membrane were imaged by SUPERSIGNAL™ enhanced chemiluminescent substrate (Thermo Fisher). Following detection of phospho signal, nitrocellulose membranes were stripped and reblotted for total kinase signal. For quantification, phosphoprotein signal was normalized to total protein signal using Image Lab (Bio-Rad) within the same blot.

siRNA Knockdown

'Δ3G' HEK 293 cells were transiently transfected with either LIPOFECTAMINE® 3000 (Thermo Fisher) or RNAIMAX™ (Thermo Fisher) per manufacturer specifications in a six-well tissue culture sterile plate with 1 μg of receptor and either 7 μg of either control siRNA or 3.5 μg siRNA directed to β-arrestin-1 and β-arrestin-2 sequences (LIPOFECTAMINE® 3000 conditions) or 1000 ng receptor and 400 ng β-arrestin-1 and β-arrestin-2 siRNA or 800 ng of control siRNA (RNAIMAX™ conditions). 24 hours later, the cells were transiently transfected with 1000 ng of receptor using LIPOFECTAMINE® 3000 (Thermo Fisher) and left to incubate for an additional 48 hours.

Wound-Healing Migration Assay—Immortalized Cells

HEK 293T cells stably expressing the AT1R were utilized. Briefly, 70 μl of cell suspension at a concentration of 5×10⁵ cells per mL was applied into each well of silicone inserts (Ibidi, Martinsried, Germany) on 24 well plate, and after 24 hrs incubation, the inserts were removed to create a wound field. The cells were incubated additionally for 12 hrs with 1 μM of TRV120023 and visualized with a Zeiss Axio Observer microscope (Carl Zeiss, Thornwood, N.Y.). Wound healing was then analyzed using ImageJ (NIH, Bethesda, Md.) wound healing tool macros.

Wound-Healing Migration Assay—Primary Human Cells

Human pulmonary arterial smooth muscle cells (PASMCs) were isolated from human lungs from a de-identified health donor (International Institute for the Advancement of Medicine, Edison, N.J.) with Institutional Review Board approval. Human PASMCs were seeded into 24-well plates at a density of $1.5 \times 10^4$ cells per well in Human Smooth Muscle Cell Basal Medium supplemented with Human SMC Growth Supplement (Cell Application, Inc.). At 30% confluency, cells were transfected with 50 ng of control or β-arrestin-1 and β-arrestin-2 ON TARGETPLUS™ siRNA pools (Dharmacon, Inc.). When the cells reached 100% confluency, they were serum starved for 4 hours with 2 hrs of PTX (200 ng/mL) treatment. Scratches were made using small pipette tips. Cells were washed using DPBS and stimulated with basal smooth muscle cell medium containing 1 μM Angiotensin-II (Millipore Sigma) or 10 μM TRV120023 (Genscript USA Inc.). The wound closure was monitored using live-cell station Zeiss Axio Observer microscope (Carl Zeiss, Thornwood, N.Y.). The images were captured in real-time at 0 hour and for every hour until 16 hours. The initial edges of the scratch at 0 hour time point were marked and migrated distance 12-16 hrs afterwards was measured using METAMORPH® Premier software (Molecular Devices, San Jose, Calif.) at the Duke Light Microscopy Core Facility (Durham, N.C.).

TGF-Alpha Shedding Assay

GPCR Gα activity was assessed by the transforming growth factor-α (TGF-α) shedding assay. Briefly, HEK 293 cells lacking Gαq, Gα11, Gαs/olf, and Gα12/13 ('ΔGsix' HEK 293 cells) were transiently transfected with receptor, modified TGF-α-containing alkaline phosphatase (AP-TGF-α), and the indicated Gα subunit. Cells were reseeded twenty-four hours later in Hanks' Balanced Salt Solution (HBSS) (Gibco, Gaithersburg, Md.) supplemented with 5 mM HEPES in a Costar 96-well plate (Corning Inc., Corning, N.Y.). Cells were then stimulated with the indicated concentration of ligand for one hour. Conditioned media (CM) containing the shed AP-TGF-α was transferred to a new 96-well plate. Both the cell and CM plates were treated with para-nitrophenylphosphate (p-NPP, 100 mM) (Sigma-Aldrich, St. Louis, Mo.) substrate for one hour, which is converted to para-nitrophenol (p-NP) by AP-TGF-α. This activity was measured at $OD_{405}$ in a SYNERGY™ Neo2 Hybrid Multi-Mode (BioTek, Winooski, Vt.) plate reader immediately after p-NPP addition and after one-hour incubation. Gα activity was calculated by first determining p-NP amounts by absorbance through the following equation:

$$100 * \frac{\Delta OD\ 405\ CM}{\Delta OD\ 405\ CM + \Delta OD\ 405\ cell}$$

where ΔOD 405=OD 405 1 hour−OD 405 0 hour and ΔOD 405 cell and ΔOD 405 CM represent the changes in absorbance after one hour in the cell and CM plates, respectively. Data were normalized to a single well that produced the maximal signal.

Thermal Shift Assay

Protein thermal melting shift experiments were performed using the STEPONEPLUS™ Real-Time PCR System (Applied Biosystems). Proteins were buffered in 20 mM HEPES pH 7.5, 100 mM NaCl, 4 mM $MgCl_2$. β-arrestin-2, $G_{\alpha i\beta\gamma}$, V2Rpp, Fab30, and GTPγS (nonhydrolyzable GTP analog) were added at a final concentration of 5 μM, 10 μM, 30 μM, and 120 μM, respectively. All reactions were set up in a 96-well plate at final volumes of 20 μl and SYPRO™ Orange (Thermo Fisher Scientific) was added as a probe at a dilution of 1:1000. Excitation and emission filters for the SYPRO™ Orange dye were set to 475 nm and 580 nm, respectively. The temperature was raised with a step of 0.5° C. per 30 second from 25° C. to 99° C. and fluorescence readings were taken at each interval. All measurements were carried out three times. Data were analyzed using APPLIED BIOSYSTEMS® PROTEIN THERMAL SHIFT™ Software. Expression and purification of heterotrimeric G protein was conducted. In brief, Hive Five insect cells were infected with two viruses made from BestBac baculovirus system, one expressing human Gβ1-His6 and Gγ2 and the other Gαi1. Approximately forty-eight hours after infection the cells were harvested, solubilized, and heterotrimeric Gαi purified using Ni-NTA chromatography and HITRAP® Q sepharose anion exchange (GE Healthcare Life Sciences).

Purified Component Pull Down

Expression and purification of β-arrestin-2 and heterotrimeric $G_{\alpha i}$ were purified as described above. Briefly, purified glutathione S-transferase tagged β-arrestin-2 and purified heterotrimeric G protein were added together at a final concentration of 4 μM and 1 μM, respectively, and placed on a tube revolver at room temperature for 30 minutes. Once complete, the solution was added to 40 uL of washed glutathione agarose beads and placed on a tube rotator at room temperature for 60 minutes. After removal of the supernatant, samples were washed three times with 300 uL of 20 mM HEPES pH 7.5, 100 mM NaCl. The sample was then eluted with 200 uL of 2×SDS-sample buffer (8% SDS, 5% β-mercaptoethanol, 10% glycerol and 25 mM Tris pH 6.8). Protein was resolved on SDS-10% polyacrylamide gels, transferred to nitrocellulose membranes, and immunoblotted with antibodies directed to either 400 ng β-arrestin-1/2 (A1-CT, from laboratory of R J Lefkowitz) or Gαi1 (13533, Santa Cruz Biotechnology).

Immunoprecipitation

Immunoprecipitation was conducted. Briefly, 4 μg of HA-V2R, 4 μg of Gαi-GFP and 4 μg of pcDNA-ARRB1-Flag and/or pcDNA were transfected into HEK 293 cells seeded in 6 cm plates. Forty-eight hours post-transfection, after approximately 4 hours of serum starvation, cells were stimulated with AVP for 5 and 10 mins at 37° C. Cells were then lysed on ice for 10 min in FLAG lysis buffer (50 mM Tris-HCl, pH 7.4, 1% Triton X-100, 150 mM NaCl, 1 mM EDTA) supplemented with protease inhibitor cocktail tablet (Roche). Cell lysates were incubated with anti-FLAG M2 affinity gel (A2220, Sigma) overnight and immunoprecipitated ARRB1-FLAG were eluted with Flag peptides (F3290, Sigma). For primary antibody incubation, GFP polyclonal antibody (A6455, Invitrogen), HA-Tag (3724S, cell signaling biotechnology), and ANTI-FLAG M2 antibody (F3165, Sigma) were utilized.

Confocal Microscopy

HEK293T cells plated in fibronectin-coated 35 mm glass bottomed dishes (MatTek Corp. P35G-0-14-C) were transiently transfected via the calcium-phosphate method with DNA encoding $G_{\alpha i}$-mVenus (125 ng), βarr2-mKO (125 ng), and/or Mars1-V2R (500 ng). Mars1 binds a membrane impermeant fluorogen (SCi1) and induces its fluorescence in the near-infrared spectrum. Cells were pulse labelled with SCi1 (diluted 1:5000 from 0.5 mg/mL stock) for 15 minutes before treatment with or without 100 nM AVP. Cells were then fixed at basal, 5 minutes, and 30 minutes after treatment with 4% paraformaldehyde. Samples were then imaged with a Plan-Apochromat 63x/1.4 Oil lens on a Zeiss LSM880 using corresponding laser lines to excite mVenus, mKO, or Mars1 (488 nm, 561 nm, 633 nm respectively). Spectral gating via a 34 spectral array detector was performed using single color transfection controls.

Drugs

VUF10661, AVP, dopamine, angiotensin II, neurotensin and isoproterenol were all purchased from Sigma Aldrich (St. Louis, Mo.). VUF10661 and isoproterenol were dissolved in dimethyl sulfoxide (DMSO) to make stock solutions and stored in a desiccator cabinet. Stock solutions of AVP, angiotensin II, neurotensin, (Sigma-Aldrich) were prepared according to manufacturer specifications. TRV120023 was provided by Trevena (King of Prussia, Pa.). Stock solutions of neurotensin were made in 0.1% BSA in PBS. Dopamine was prepared fresh in BRET media supplemented with 0.03% ascorbic acid (Sigma-Aldrich). H3192 and SR121463 were kindly provided by the laboratory of R. J. Lefkowitz. All drug dilutions were performed with BRET media or cell culture media. PTX was obtained from List Biological Laboratories (Campbell, Calif.). All compound stocks were stored at −20° C. until use.

Statistical Analyses

Dose-response curves were fitted to a log agonist versus stimulus with three parameters (span, baseline, and EC50) with the minimum baseline corrected to zero using Prism 8.0 (GraphPad, San Diego, Calif.). For comparing ligands in concentration-response assays or time-response assays, a two-way ANOVA of ligand and concentration or ligand and time, respectively, was conducted. For some analyses, a post hoc comparison was also made. Unless otherwise noted, statistical tests were two-sided and Bonferroni analyses were corrected for multiple comparisons.

Example 2: Complex Bioluminescent Resonance Energy Transfer (BRET)

Classically, G protein-coupled receptors (GPCRs) couple to a specific Gα protein subtype and activate G proteins by catalyzing guanine nucleotide exchange. These distinct Gα protein subtypes then amplify specific second messenger signaling systems, such as cAMP. β-arrestins were subsequently discovered to inhibit, or 'arrest,' canonical G protein-mediated signaling, while later found to promote other forms of GPCR signaling, such as phosphorylation of extracellular signal-regulated kinase (ERK). More recently, the ability of G proteins and β-arrestins to coordinate their signaling has been suggested by the demonstration of a "megaplex" signaling complex consisting of a GPCR bound to both G protein and β-arrestin. However, the ability of Gα proteins to directly interact with β-arrestins to form signaling scaffolds on the plasma membrane has not previously been appreciated. A 'complex' bioluminescent resonance energy transfer (BRET) approach was developed to identify tripartite interactions between GPCRs, Gα proteins and β-arrestins. It was found that agonist treatment of the Gαs-coupled vasopressin type 2 receptor (V2R) catalyzed the formation of Gαi arrestin scaffolds that were not observed between β-arrestin and other Gα subtypes, despite the inability of the V2R to promote canonical Gαi signaling. Gαi:β-arrestin complexes were also formed downstream of each of the GPCRs that were tested, which included receptors canonically coupled to Gαs, Gαi, and Gαq. Gαi:β-arrestin scaffolds were not observed to form with other Gα subtypes. Notably the Gαi:β-arrestin scaffolds formed complexes with GPCRs and could also bind ERK. Disrupting Gαi and β-arrestin interactions attenuated V2R-mediated transduction of ERK phosphorylation. In addition, disrupting Gαi and β-arrestin interactions eliminated GPCR-mediated migration towards a β-arrestin-biased agonist that does not stimulate canonical Gαi signaling. These results reveal a new GPCR signaling mechanism, and the formation of Gαi:β-arrestin signaling scaffolds.

β-Arrestin, Gαi, and Receptor Form Complexes

Figure 1B:
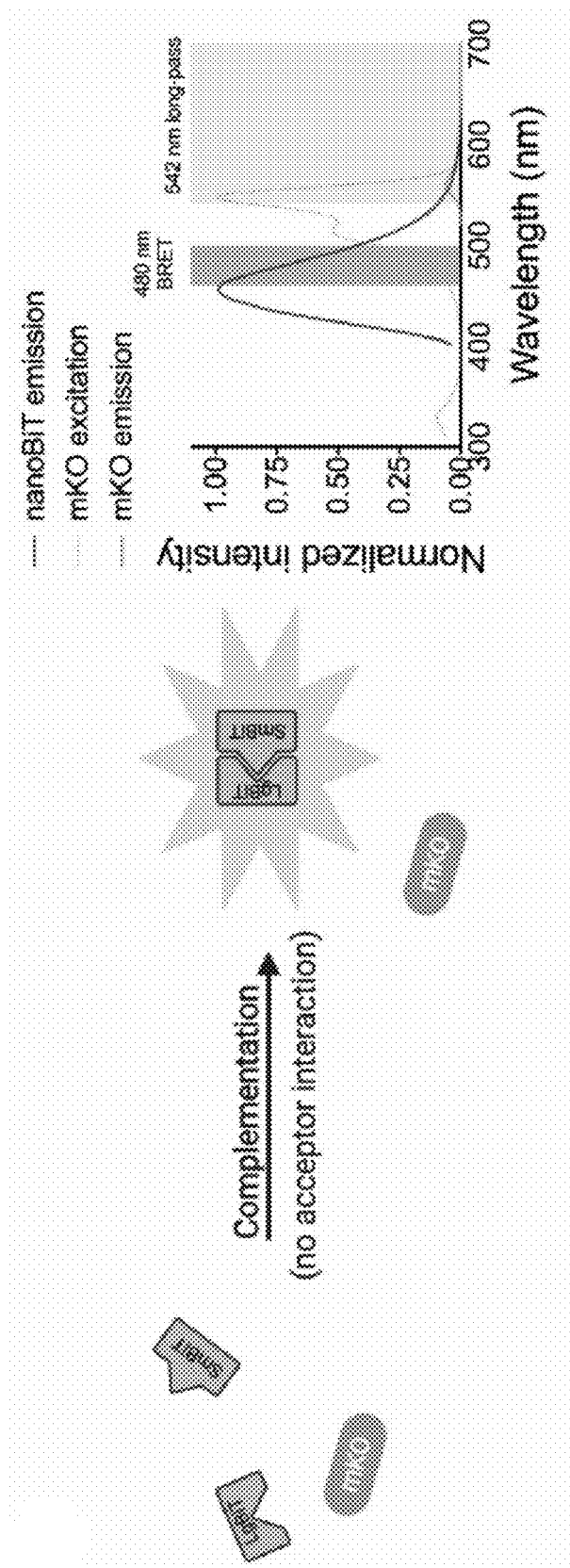
Figure 1C:
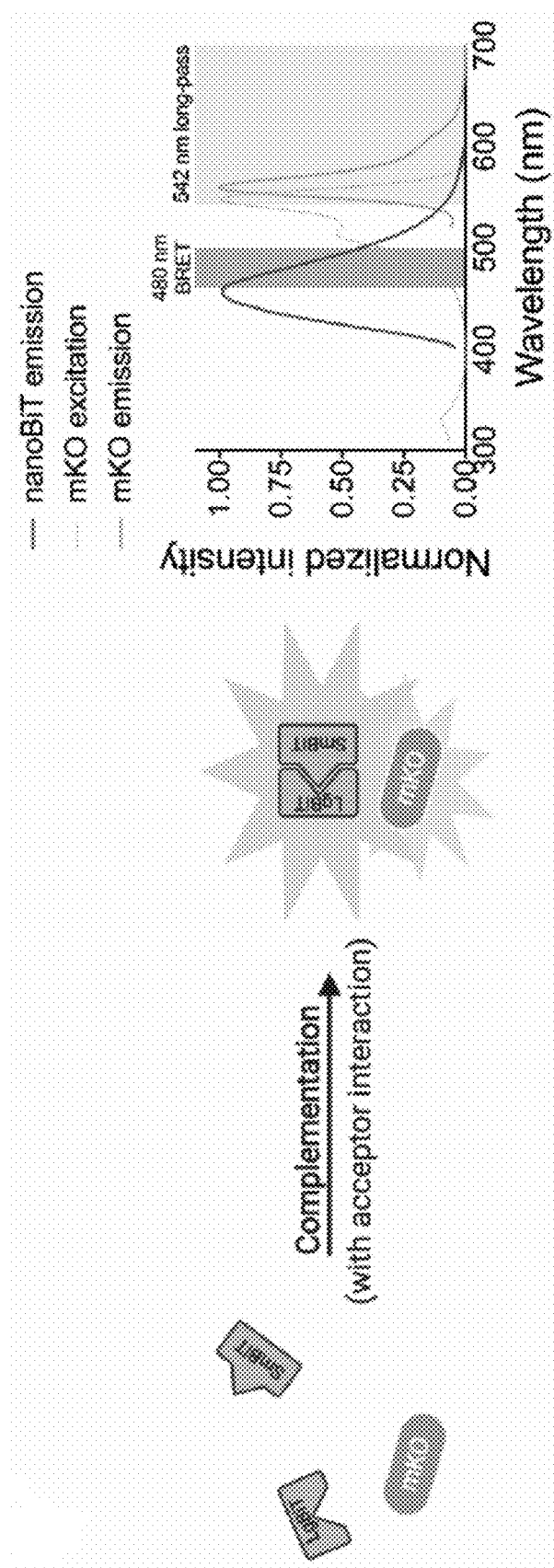
Figure 2A:
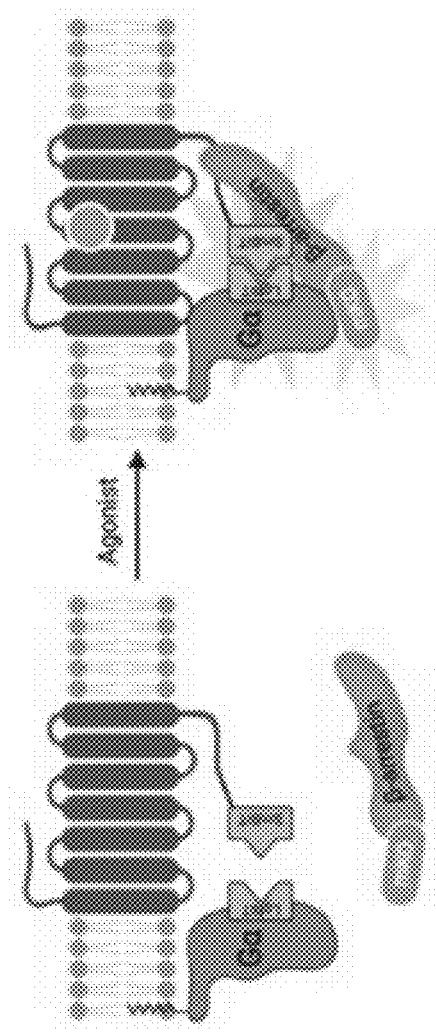
FIGS. 2A-J shows formation of G protein:β-arrestin: GPCR complexes, where
Figure 2B:
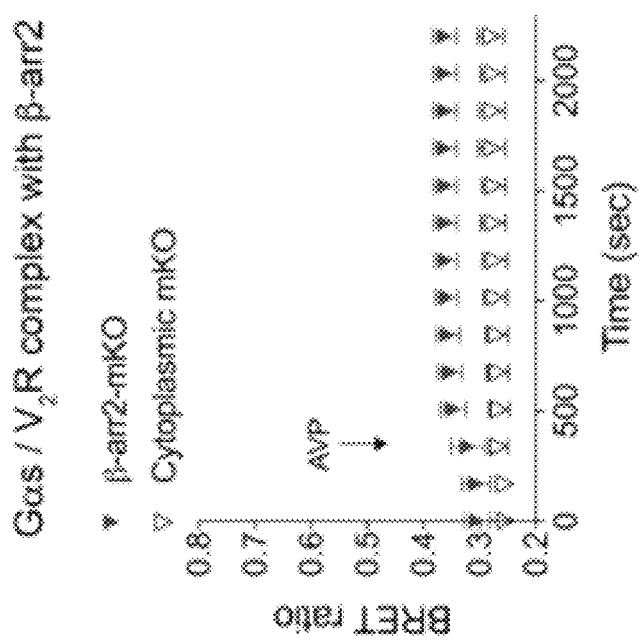
Figure 2C:
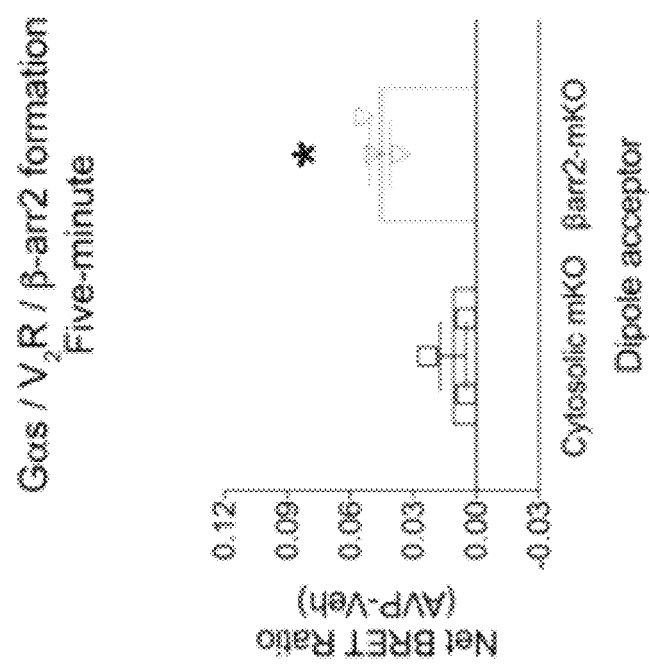
Figure 2D:
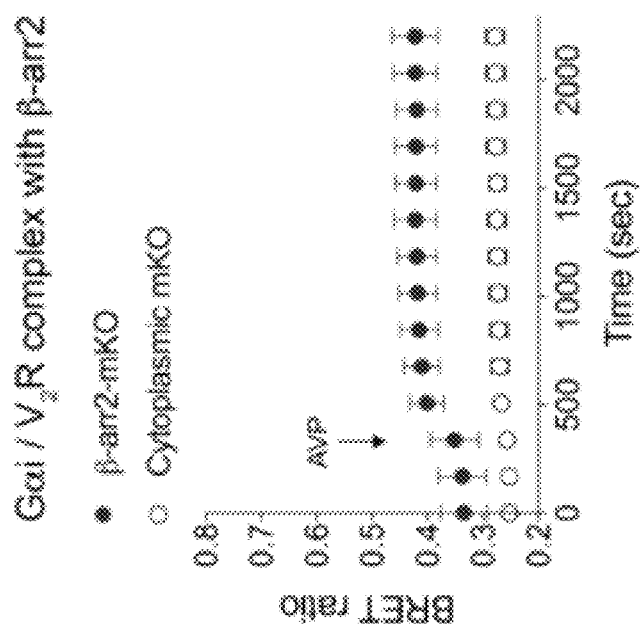
Figure 2E:
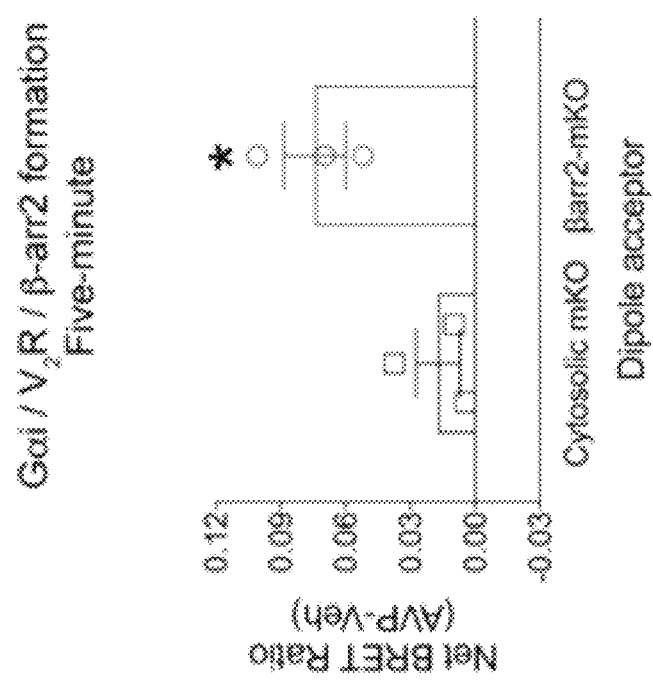
Figure 2F:
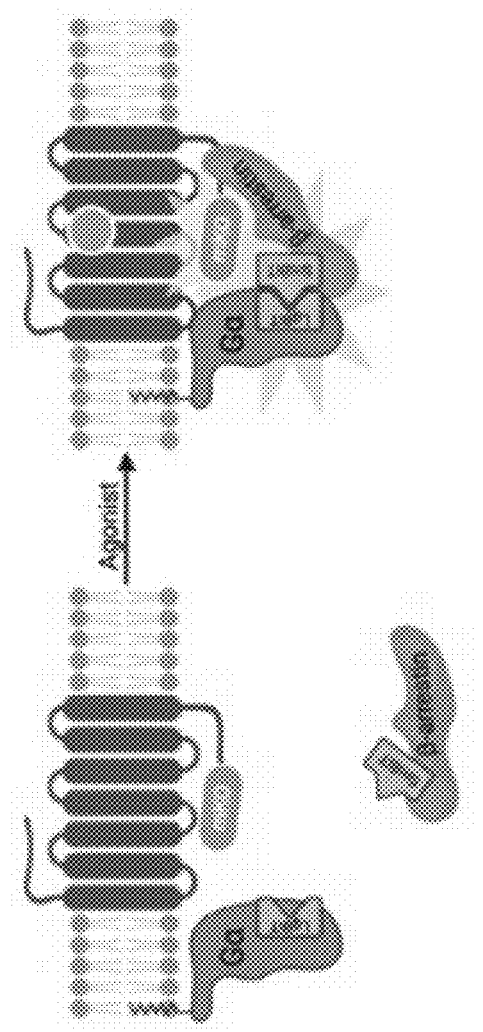
Figure 2G:
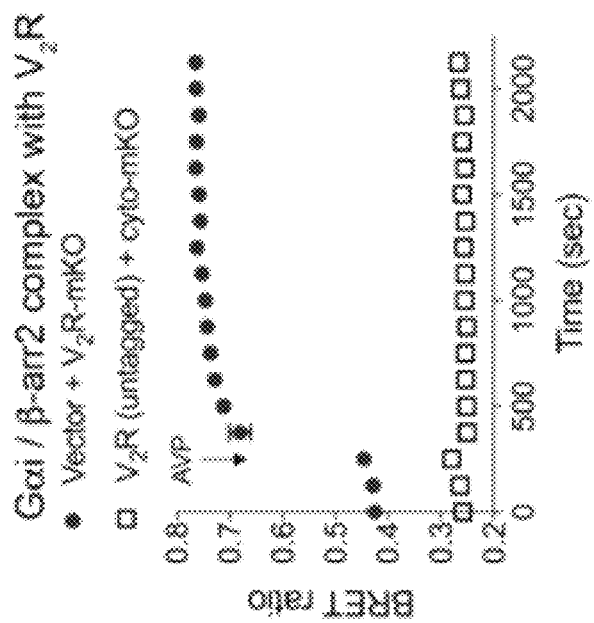
Figure 2H:
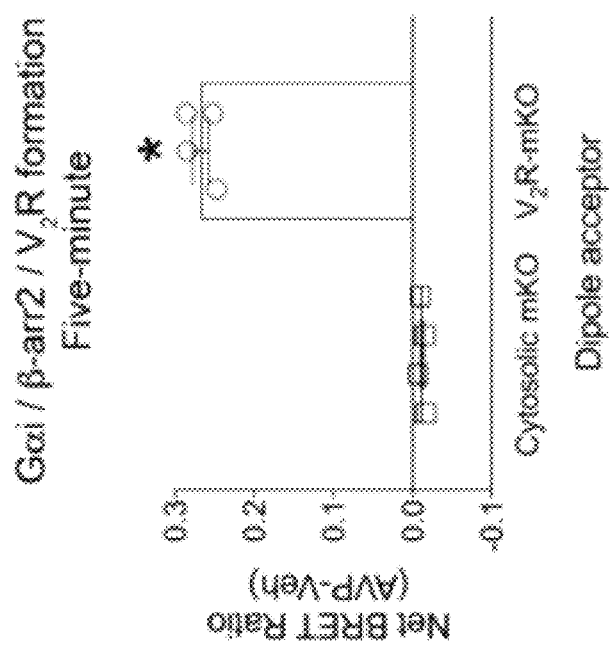
Figure 2I:
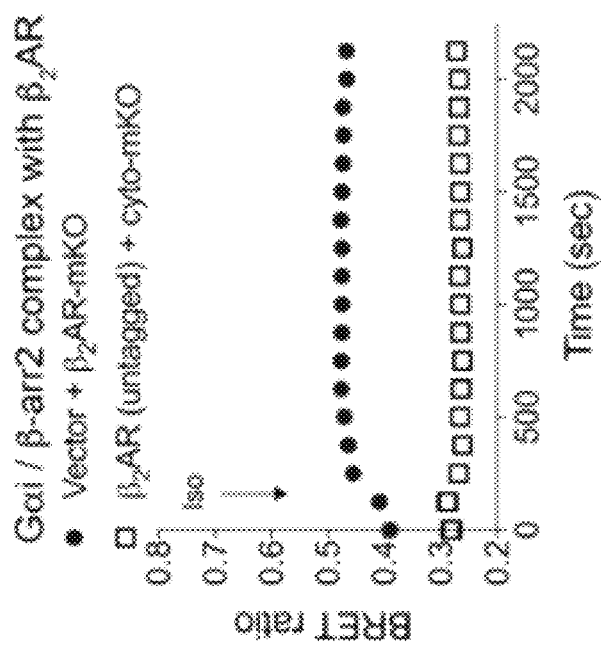
Figure 2J:
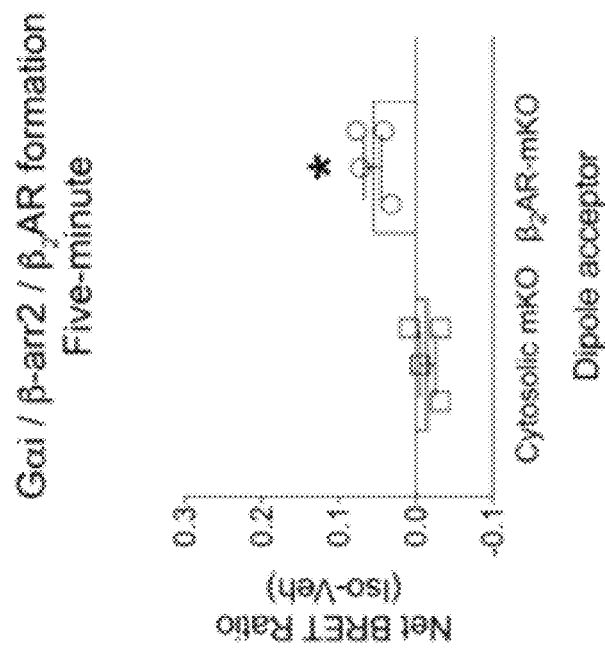
Figure 9A:
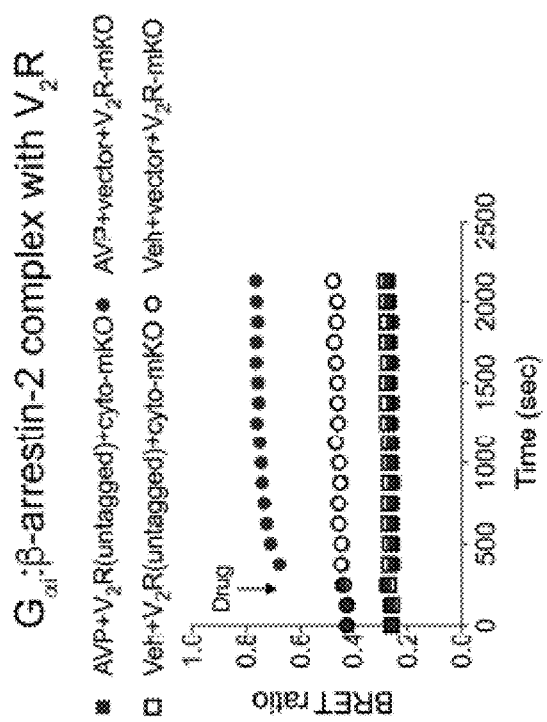
FIGS. 9A-H show additional complex BRET controls in which HEK 293T cells were transiently transfected with the indicated receptor(s) and assay components (cytosolic mKO (untagged) was utilized as a non-specific dipole acceptor control), where
Figure 9B:
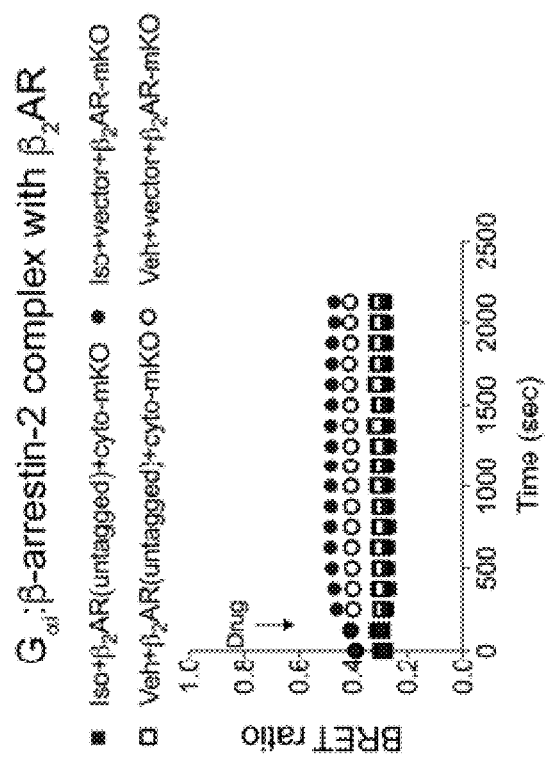
Figure 9C:
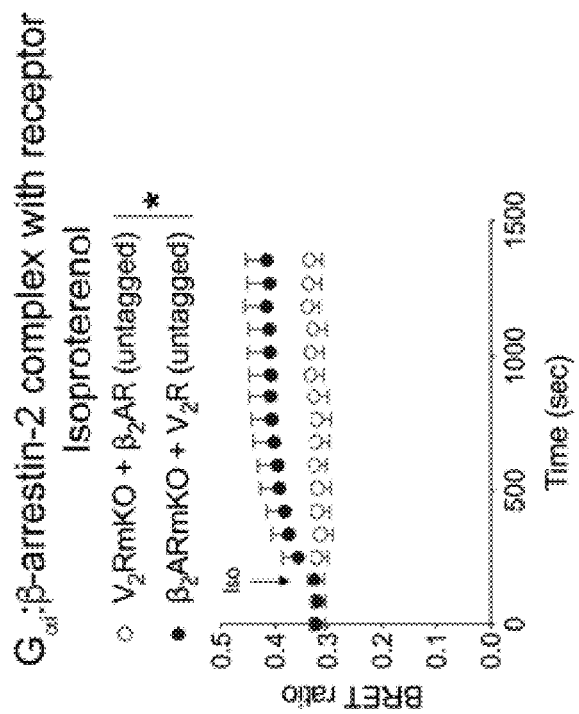
Figure 9D:
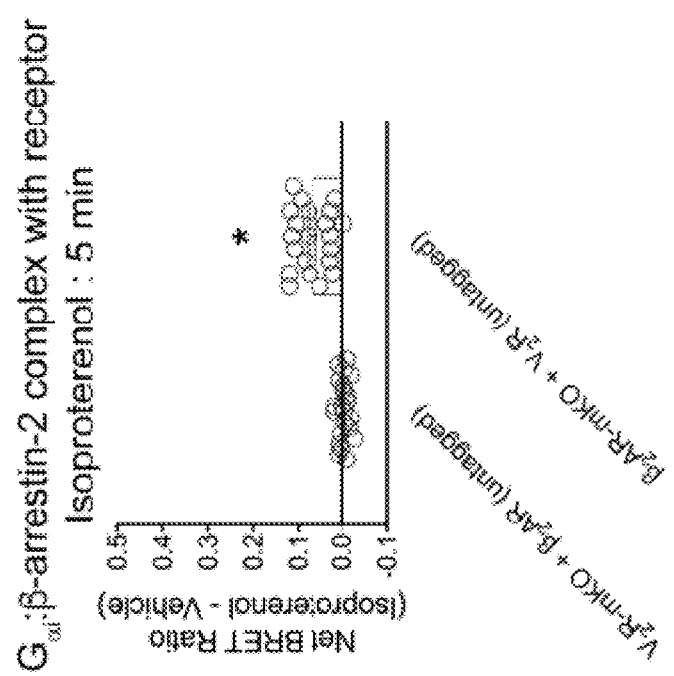
Figure 9E:
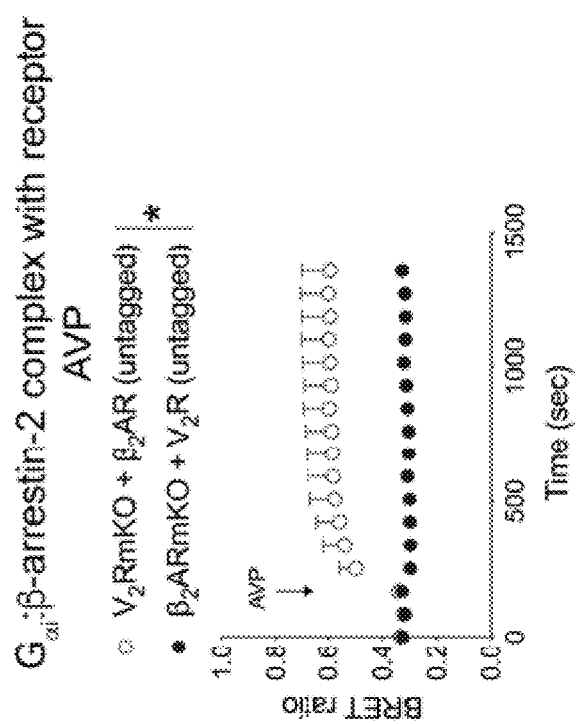
Figure 9F:
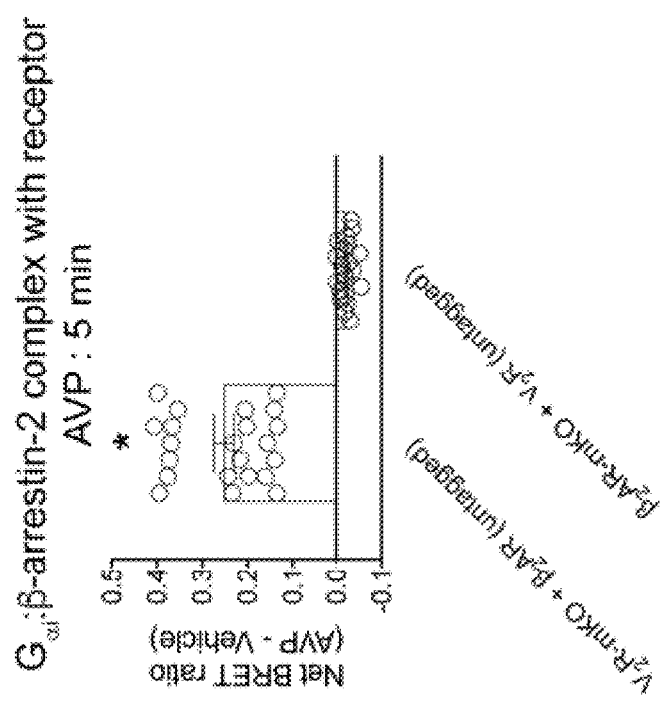
Figure 9G:
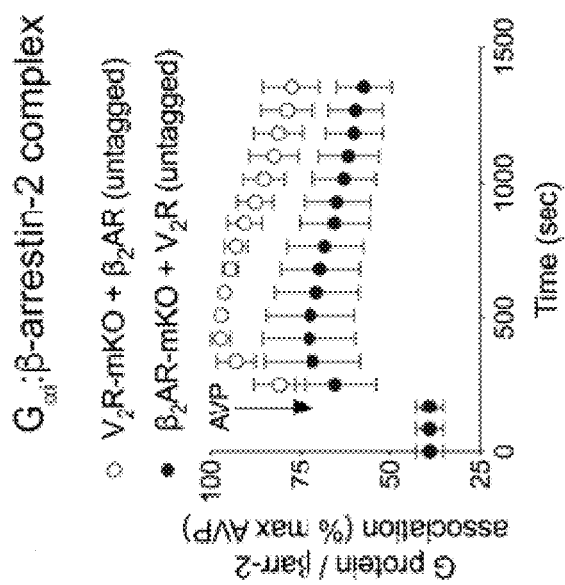
Figure 9H:
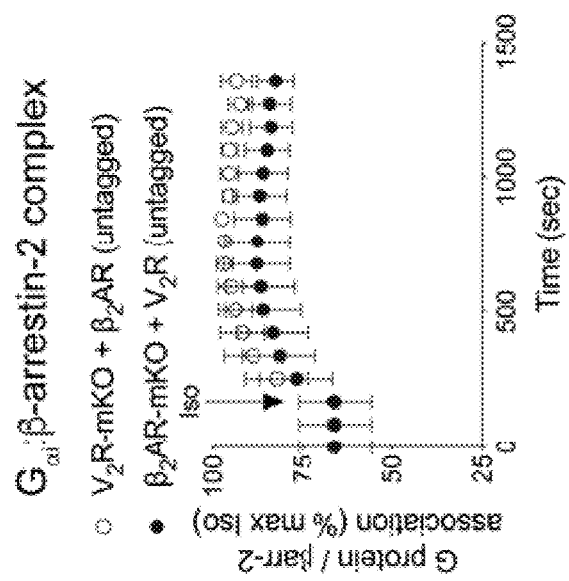

Complex BRET used a split luciferase system (NANOBIT®), relying on a small 11 amino acid complementing peptide (smBiT) fused to one protein and a near-full length nanoluciferase (LgBiT) fused to another protein (FIG. 1). The complementation of the split luciferase components is driven by the interaction of their fusion partners (e.g., β-arrestin and Gα proteins) as smBiT and LgBiT possess low affinity for each other. When complemented, the split luciferase can then transfer energy to a third protein tagged with the fluorescent protein acceptor, monomeric Kusabira Orange (mKO), generating a BRET response (FIGS. 1B and 1C). This technology enabled real-time quantification of interactions between three proteins in living cells, and it was used to confirm simultaneous interactions between Gαs, β-arrestin, and V2R following agonist treatment (FIGS. 2B and 2C). Using this technology, it was surprisingly discovered that the canonically Gαs-coupled V2R also formed a complex with Gαi and β-arrestin following agonist treatment (FIGS. 2D and 2E). To further interrogate Gαi:β-arrestin:V2R complexes, the location of the dipole donor and acceptor components was swapped (FIG. 2F). Rearranging the complex BRET components increased the observed signal and further confirmed that Gαi:β-arrestin complexes can associate with the V2R (FIGS. 2G and 2H; FIG. 9A). Agonist treatment of the canonically Gαs-coupled β2AR also formed Gαi:β-arrestin:β2AR complexes (FIGS. 2I and 2J; FIG. 9B). The specificity of Gαi:β-arrestin:GPCR complex formation was further validated by co-transfecting both untagged and mKO-tagged β2AR and V2R. Only treating the mKO-tagged receptor with its cognate agonist formed an observable Gαi:β-arrestin:GPCR complex (FIGS. 9C-H), indicating a specific interaction of Gαi:β-arrestin with its cognate receptor and not a bystander effect.

Gαi:β-Arrestin:V2R Complexes Form at the Plasma Membrane

Figure 3A:
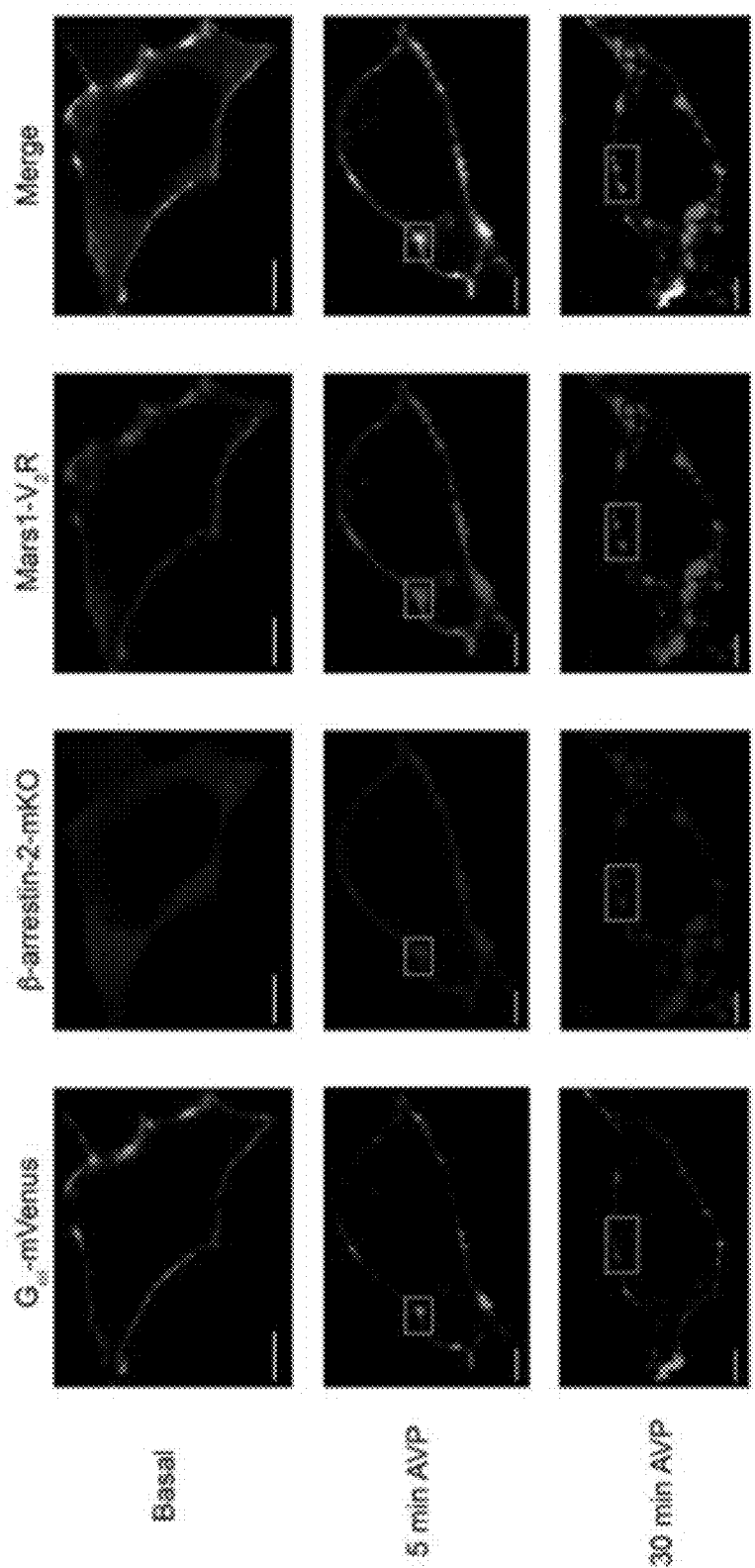
FIGS. 3A-D show results of confocal microscopy experiments on Gαi:β-arrestin:V2R complexes, with confocal microscopy analysis of AVP-induced complexes of Gαi:β-arrestin:V2R in HEK 293 cells transfected with mVenus-tagged Gαi, mKO-tagged β-arrestin-2 and Mars1-tagged V2R, where
Figure 3B:
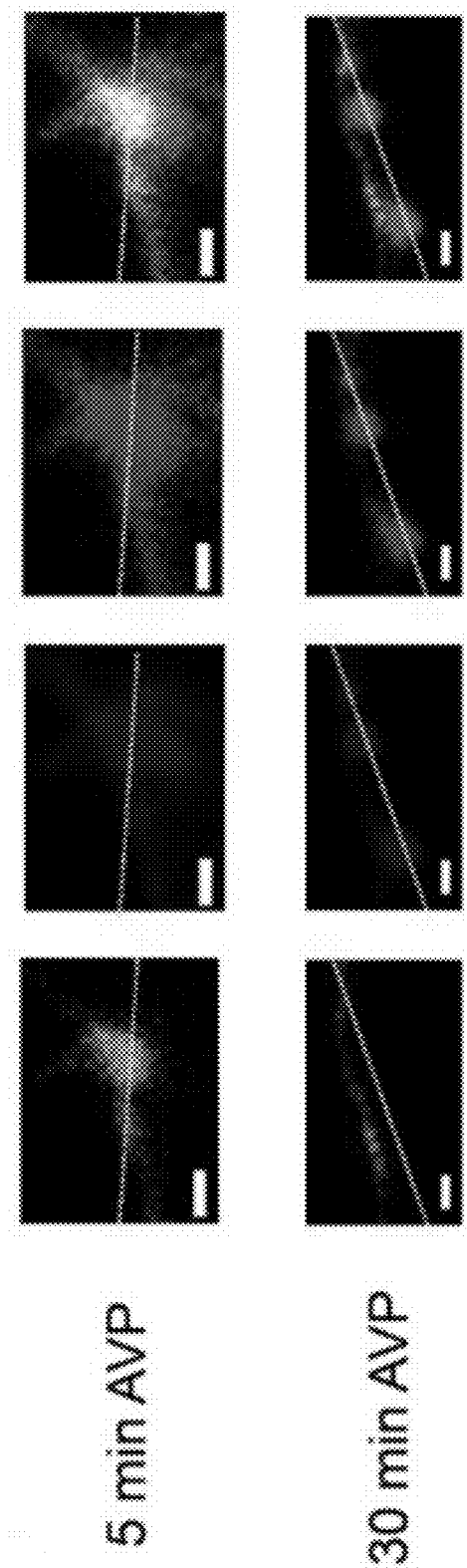
Figure 3C:
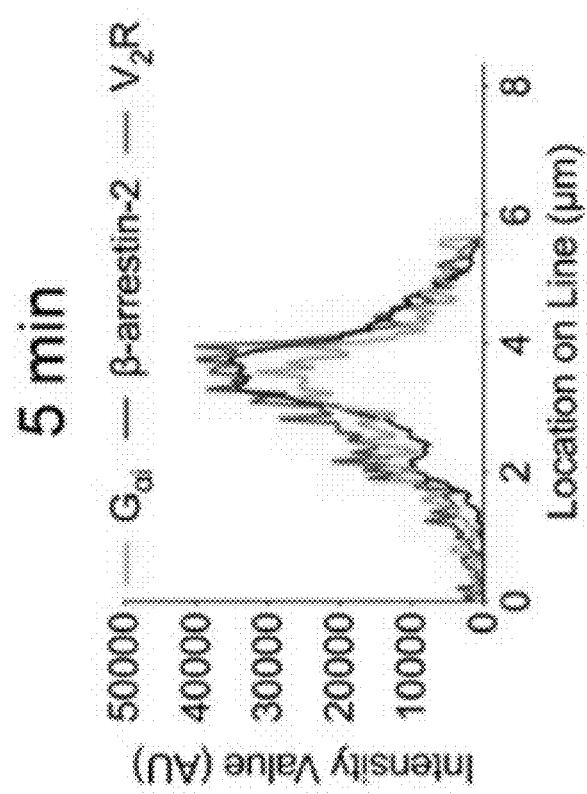
Figure 3D:
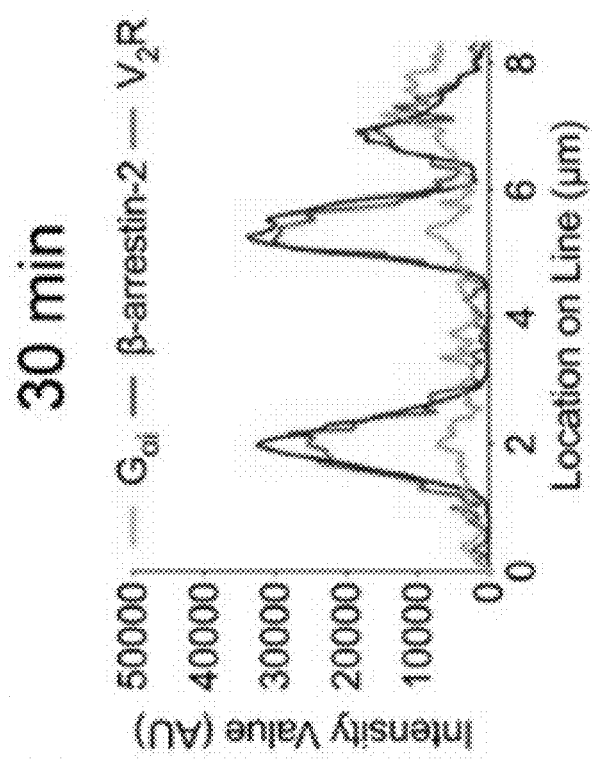

Colocalization of Gαi, β-arrestin, and V2R was visualized using confocal microscopy (FIG. 3A). Imaging parameters were validated using single-color controls to ensure accurate quantification of each component channel. Colocalization of Gαi, β-arrestin, and V2R occurred after agonist treatment and was most prominent at the plasma membrane. Line scan analyses demonstrated plasma membrane-localized puncta with colocalization of Gαi, β-arrestin, and V2R components after 5 minutes of agonist treatment (FIGS. 3B and 3C). Thirty minutes after agonist treatment, clear endosomal β-arrestin:V2R colocalization was observed that lacked substantial Gαi (FIG. 3D). These observations are consistent with colocalization of Gαi, β-arrestin, and V2R that occurs after agonist treatment and is most prominent at the plasma membrane.

Figure 4A:
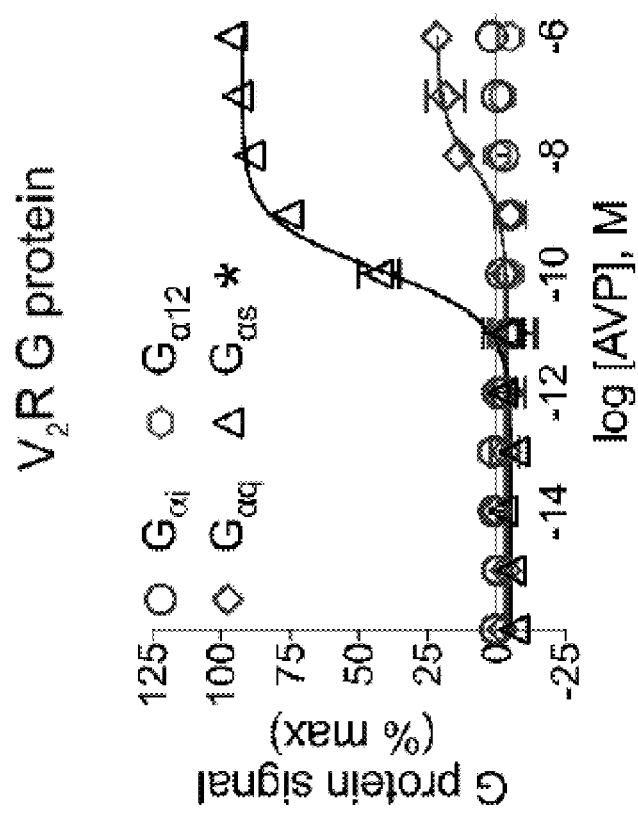
FIGS. 4A-L show that the canonically Gαs-coupled V2R forms only Gαi:β-arrestin complexes, where
Figure 4B:
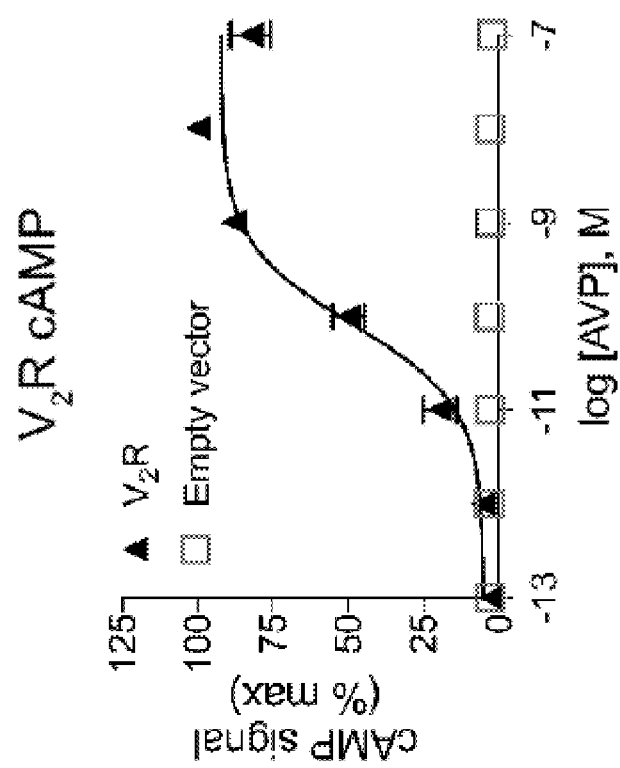
Figure 4C:
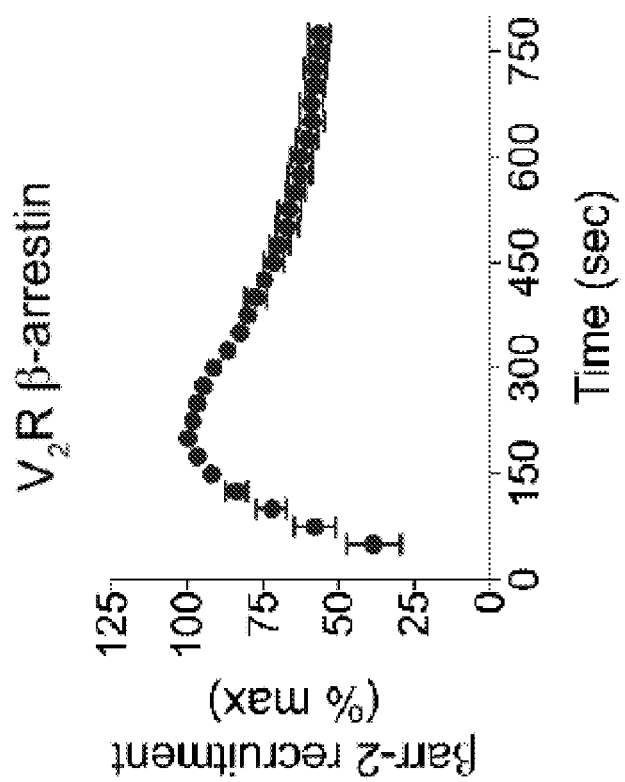
Figure 4D:
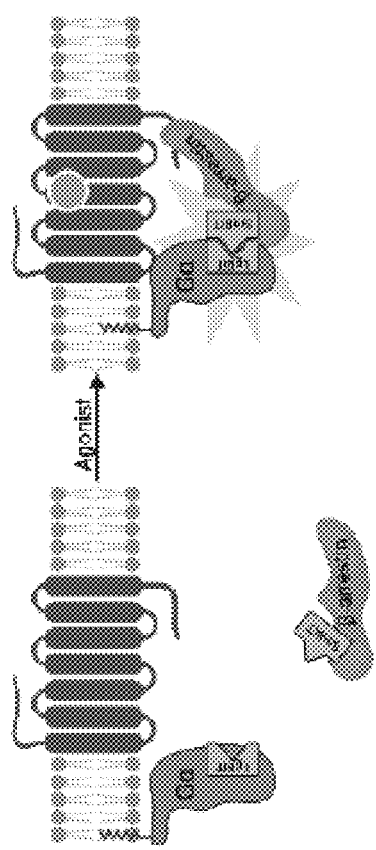
Figure 4E:
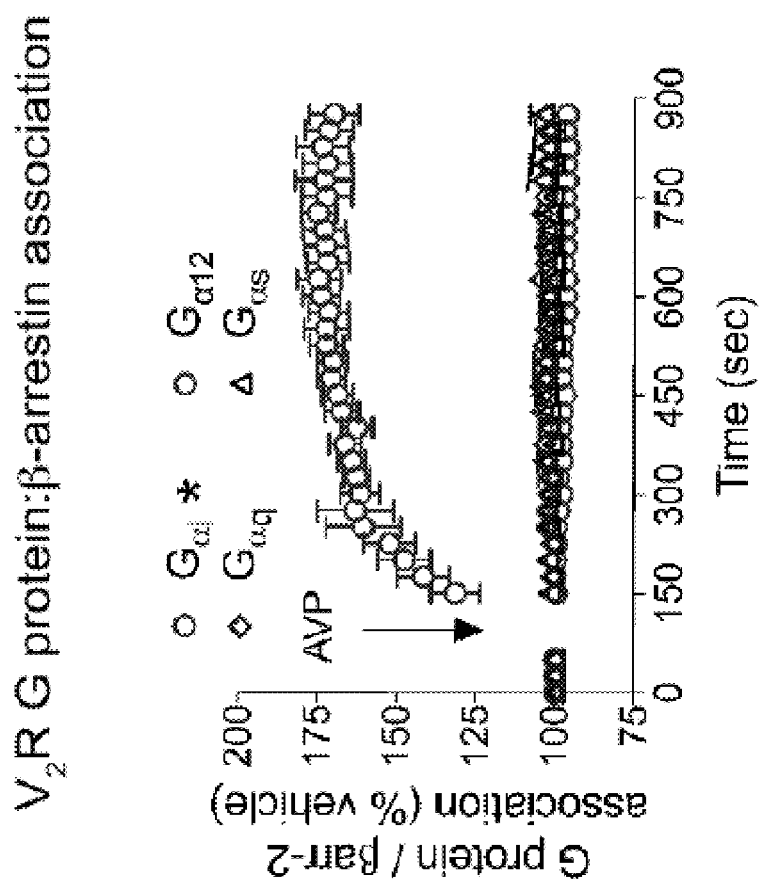
Figure 4F:
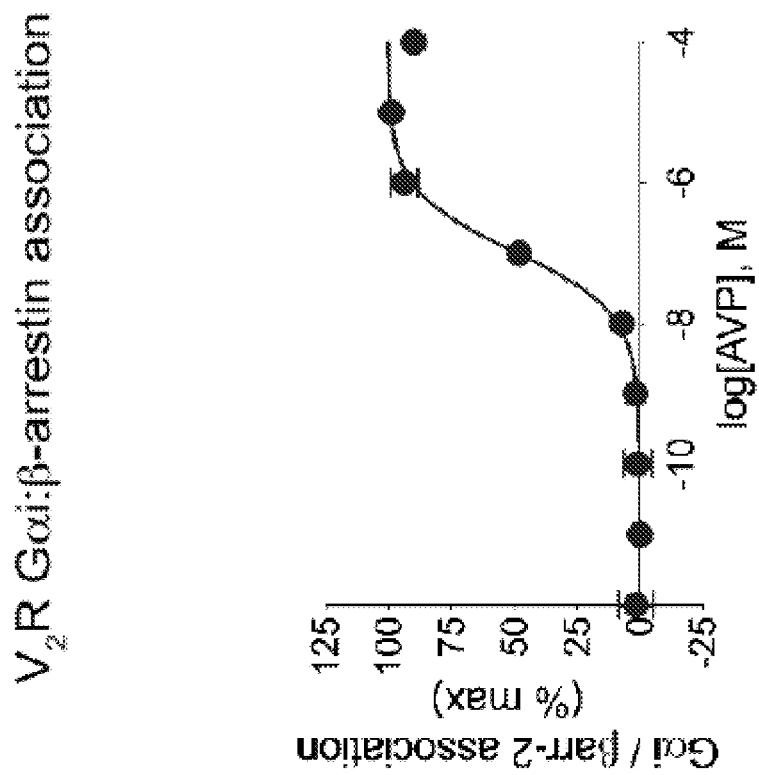

Gαi Forms Complexes with β-Arrestin that are Distinct from Gαs:β-Arrestin Megaplexes The difference in magnitude of signal observed in complex BRET between Gαi and Gαs in G protein: β-arrestin: V2R complexes suggested distinct interaction orientations. G protein signaling can exist at receptors following β-arrestin-dependent internalization and β-arrestins can be catalytically activated by an agonist-occupied receptor. It was therefore explored whether a direct functional interaction between G proteins and β-arrestins could be catalyzed by agonist treatment of the V2R. It was confirmed that the V2R canonically signalled via Gαs (FIG. 4A), increased intracellular levels of cAMP (FIG. 4B), and recruited β-arrestin (FIG. 4C). Notably V2R did not canonically signal via Gαi in a TGF-α shedding assay that relies upon overexpressed conditions (FIG. 4A). The formation of G protein and β-arrestin scaffolds among the four primary Gα families, Gαs, Gαi, Gαq, and Gα12, using the split luciferase (NANOBIT®) system was evaluated (FIG. 4D). In contrast to canonical V2R-Gαs protein signaling, only Gαi, but not Gαs, Gαq, or Gα12, formed an observable complex with β-arrestin following V2R treatment with AVP (FIGS. 4E and 4F).

Given the absence of canonical Gαi signaling, the amounts of Gα subunits transfected were varied by up to 10-fold in the Gα:β-arrestin complex formation assay. There was no observed interaction between Gαs, Gαq, or Gα12 and β-arrestin following agonist treatment of either the V2R or β2AR. However, an interaction between Gαi and β-arrestin was observed under these conditions. Transient overexpression of increasing amounts of Gαi directly correlated with increased basal association between Gαi and β-arrestin. Taken together with the decreased agonist-induced signal, these data are supportive of a unique association between Gαi and β-arrestin that can be promoted by GPCRs. As controls, it was verified that the various Gα protein subtypes were expressed at similar levels. Furthermore, Gαi isoforms 2 and 3, as well as the highly homologous Gαo, also interacted with β-arrestin following agonist treatment of the V2R. A similar Gαi-family interaction with β-arrestin-1 was also observed.

Figure 4G:
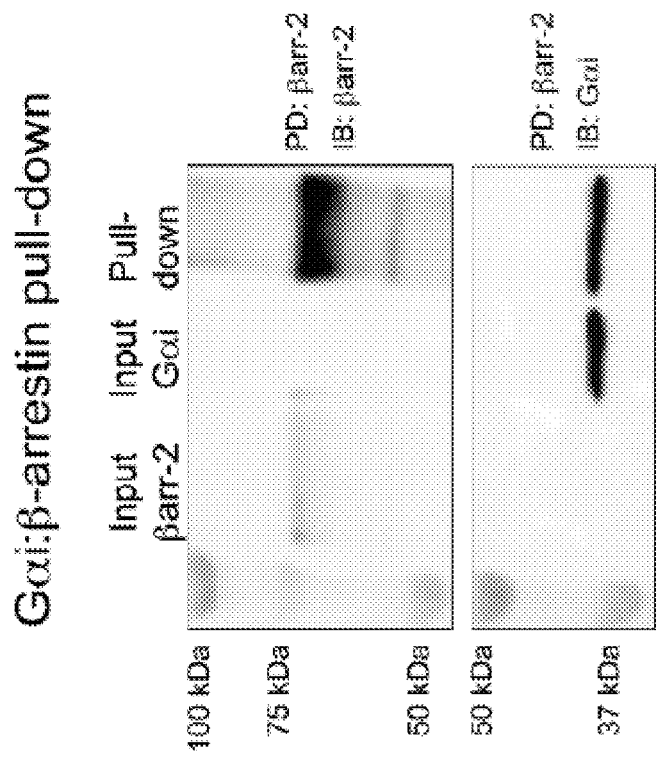

It was then tested whether Gαi and β-arrestin could interact in multiple orthogonal assays. First, nanoBRET was performed between Gα-NANOLUC® and β-arrestin-2-mKO to confirm that this complex formed only with Gαi and not Gαs. Second, it was found that purified Gαi and β-arrestin demonstrated a physical interaction in a pulldown assay (FIG. 4G). Third, a thermal shift assay was performed with purified Gαi and β-arrestin-2-394X (which induces an active conformation of β-arrestin). In the presence of non-hydrolyzable GTP, there was a significant shift in both Gαi and β-arrestin peaks, indicating an interaction. These biochemical experiments verify that Gαi and β-arrestin can directly interact without the need for other partners. Fourth, in a cellular context, it was found that co-immunoprecipitation of β-arrestin yielded both V2R and Gαi association when overexpressed in HEK 293 cells.

Figure 4H:
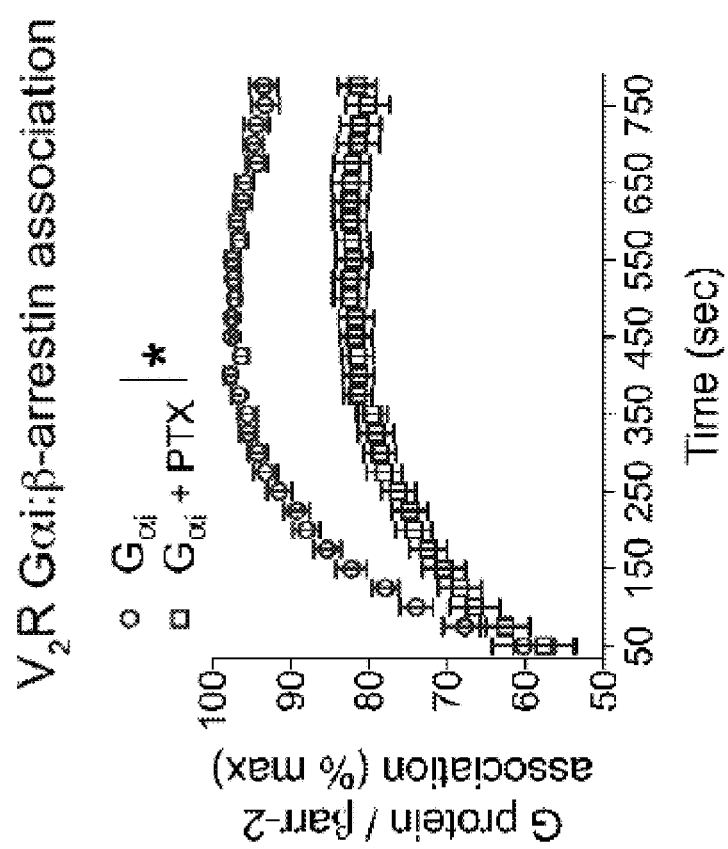
Figure 4I:
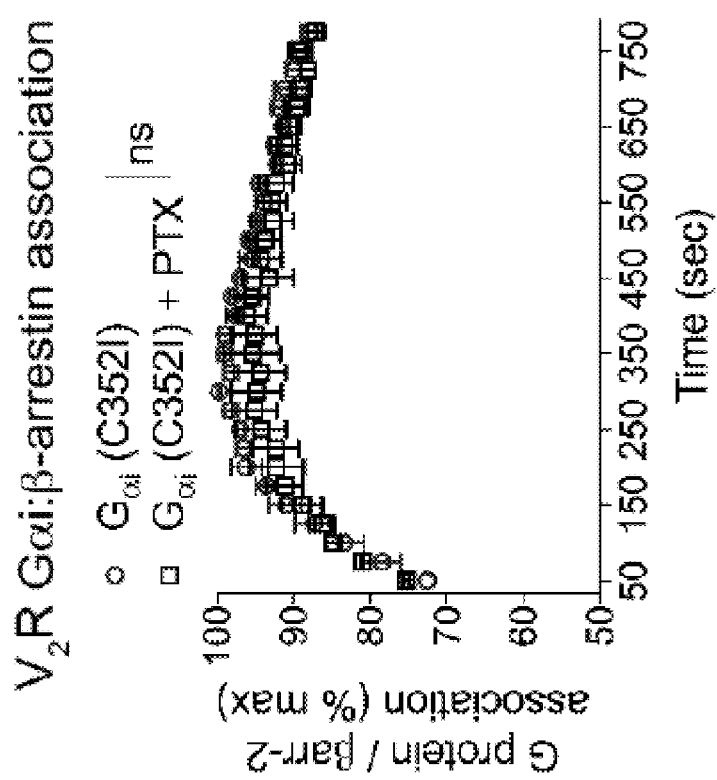

The interaction between Gαi and β-arrestin was partially sensitive to pertussis toxin (FIG. 4H), which promotes enzymatic ADP ribosylation of cysteine 352 in helix 5 of Gαi. Mutation of cysteine 352 to isoleucine rescued the effect of pertussis toxin (FIG. 4I). Pertussis toxin pretreatment did not affect β-arrestin recruitment to either the V2R or β2AR, which suggests that pertussis toxin did not reduce Gαi:β-arrestin complex formation by interfering with β-arrestin recruitment to the receptor.

It was then investigated if β-arrestin was required for Gαi recruitment to the V2R. It was found that Gαi was recruited to the V2R following agonist treatment in both wild-type and β-arrestin1/2 knockout cells. Gαs was also recruited to the V2R following agonist treatment. Either β-arrestin-2 rescue in β-arrestin1/2 knockout cells or β-arrestin-2 overexpression in wild-type cells attenuated Gαi:V2R association. These results show that canonically Gαs-coupled receptors can also recruit Gαi and that β-arrestins are not required for Gαi recruitment to the receptor.

Figure 5A:
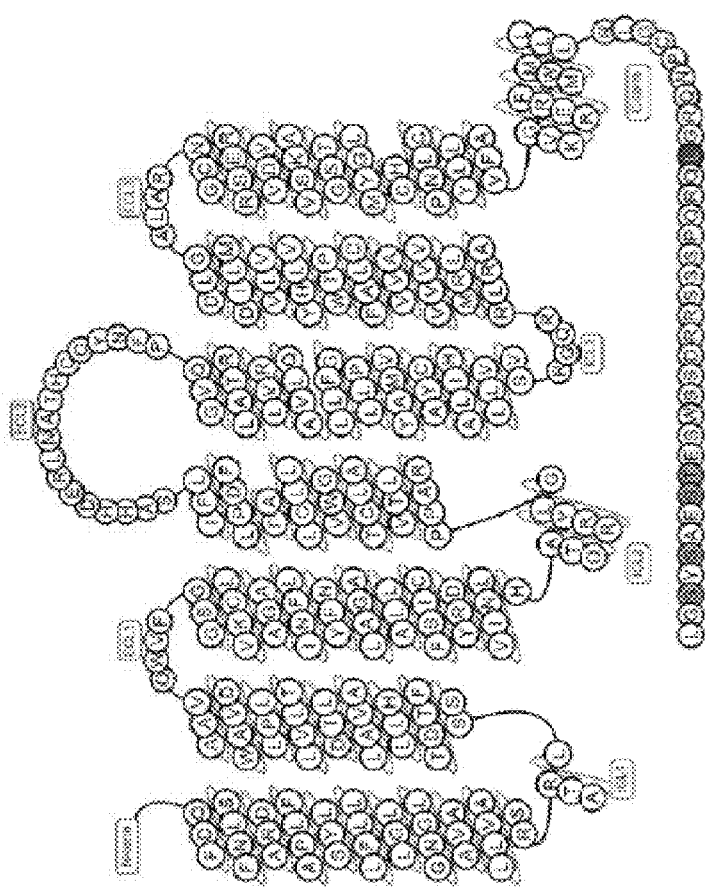
FIGS. 5A-F show that truncation or mutation of serine/threonine residues in the C-terminus of CXCR3 attenuate Gαi:β-arrestin-2 complex formation, where
Figure 5B:
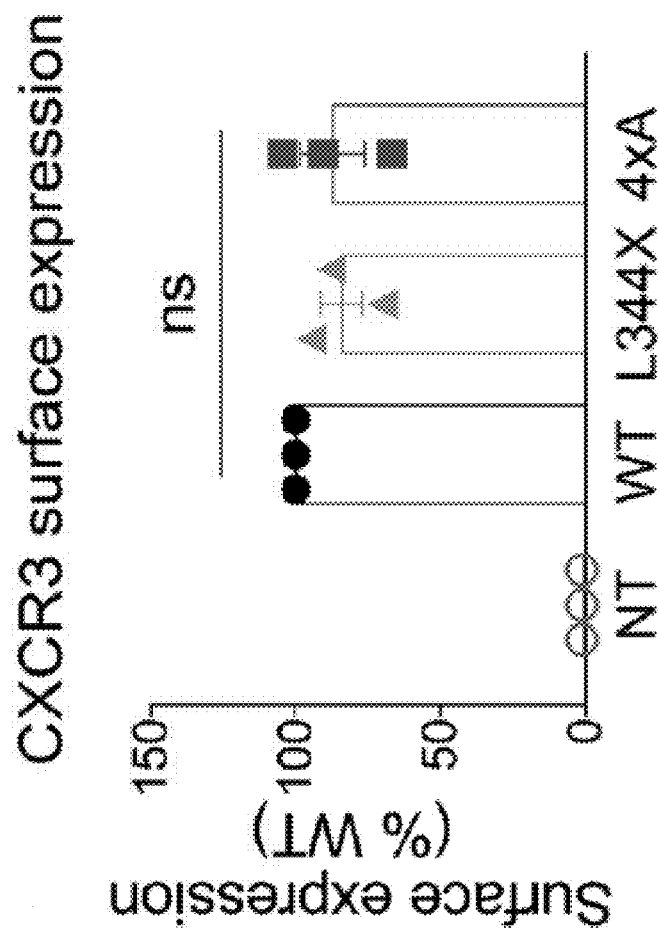
Figure 5C:
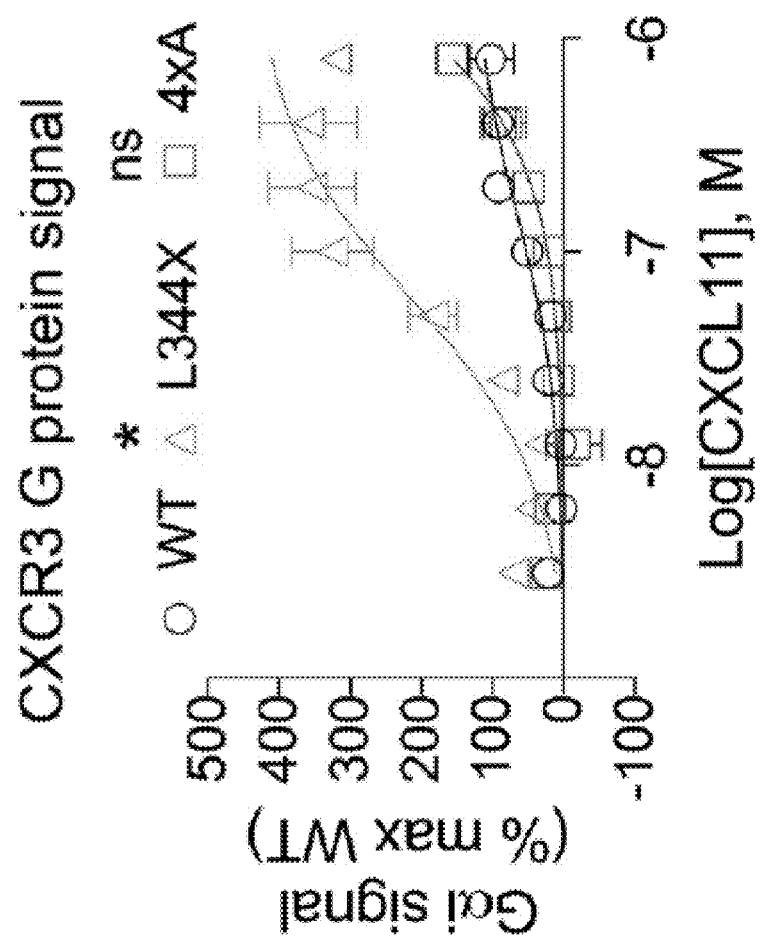
Figure 5D:
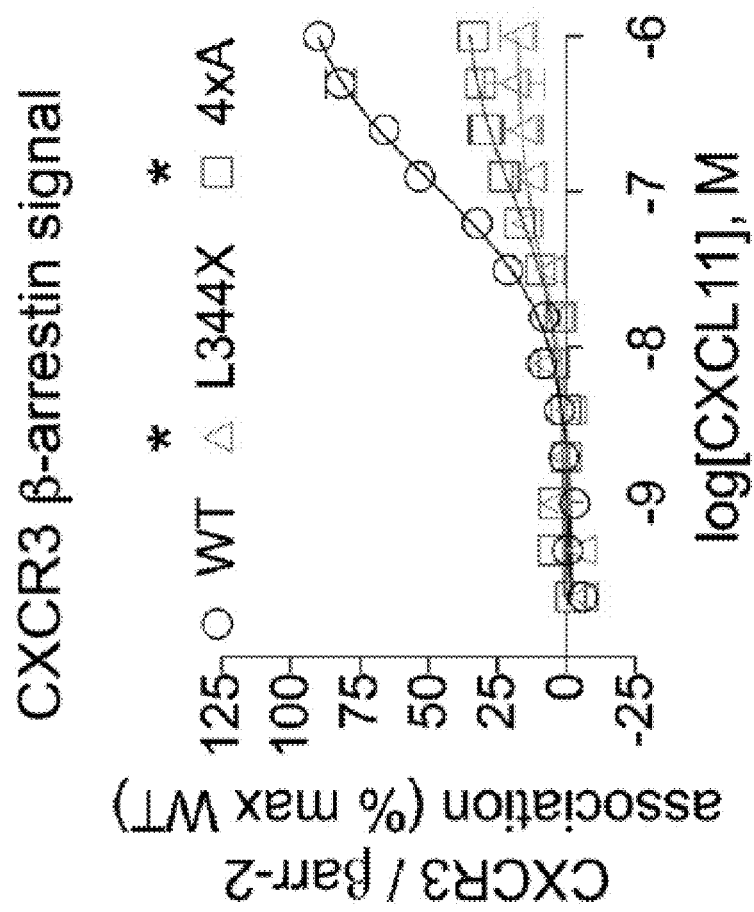
Figure 5E:
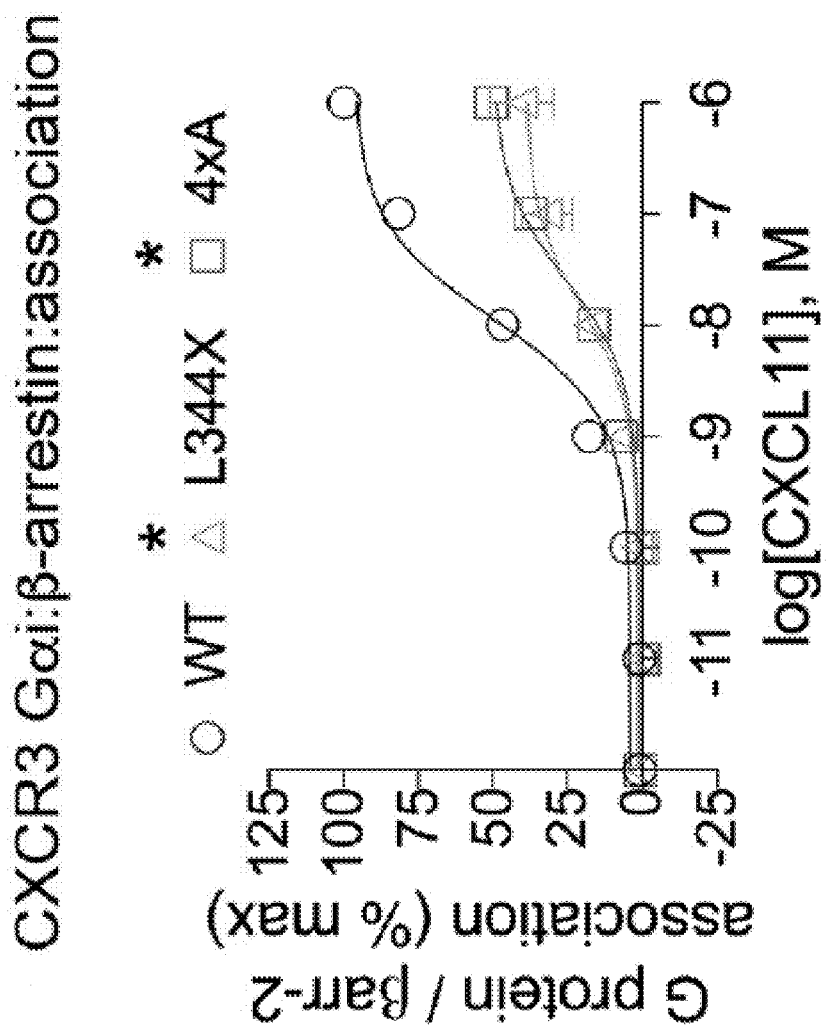
Figure 5F:
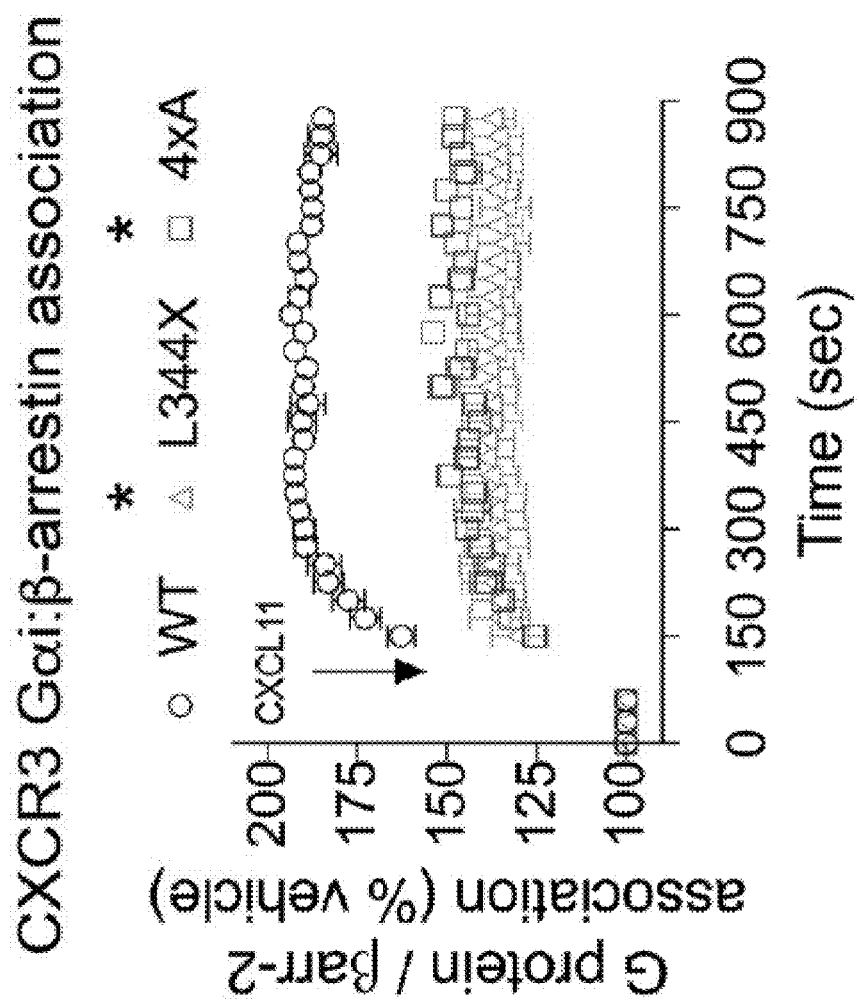
Figure 6A:
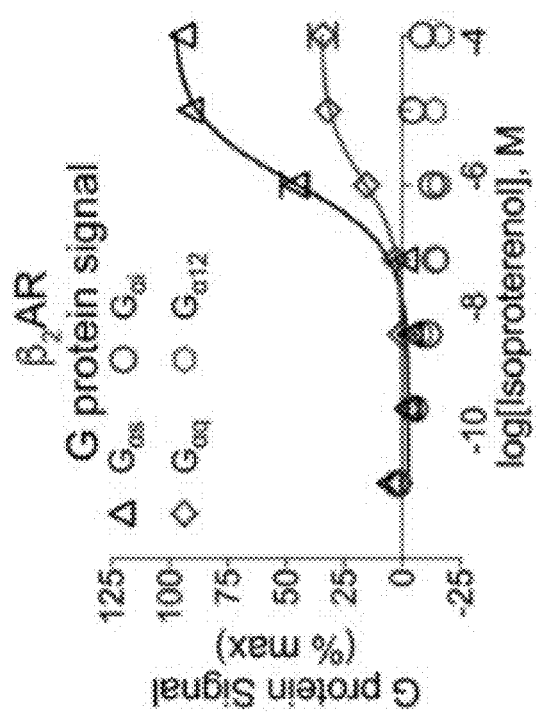
FIGS. 6A-J show that GPCRs form Gαi:β-arrestin complexes following agonist treatment regardless of canonical G protein coupling, with canonical G protein signaling with $β_2AR$ (FIG. 6A); CXCR3 (FIG. 6B); $D_1R$ (FIG. 6C); $D_2R$ (FIG. 6D); $NTS_1R$ assessed with TGF-α shedding assay following treatment with the indicated agonist (FIG. 6E); Gαi:β-arrestin complex formation with $β_2AR$ (10 μM isoproterenol) (FIG. 6F); CXCR3 (1 μM VUF10661) (FIG. 6G); $D_1R$ (500 nM dopamine) (FIG. 6H); $D_2R$ (500 nM dopamine) (FIG. 6I); and $NTS_1R$ (10 nM neurotensin) (FIG. 6J). $*P<0.05$ by two-way ANOVA, main effect of Gαi subtype. For panels A-E, n=4 per condition. For panel F, n=3-6; for panel G, n=3-4; for panel H, n=4, for panel I, n=3-4; for panel J, n=3 biological replicates per condition. Graphs show mean±s.e.m. Iso, isoproterenol.
Figure 6B:
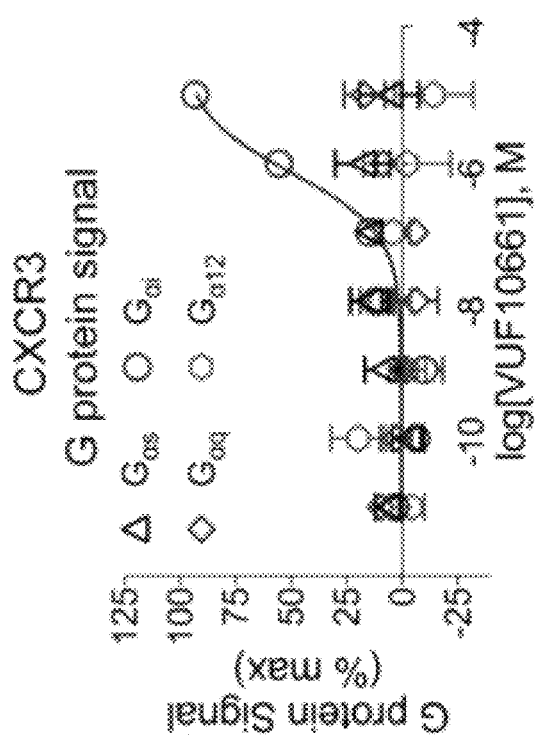
Figure 6C:
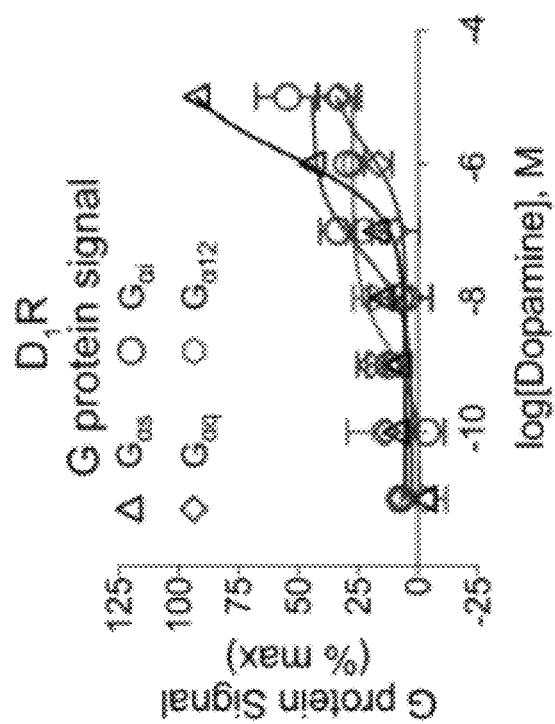
Figure 6D:
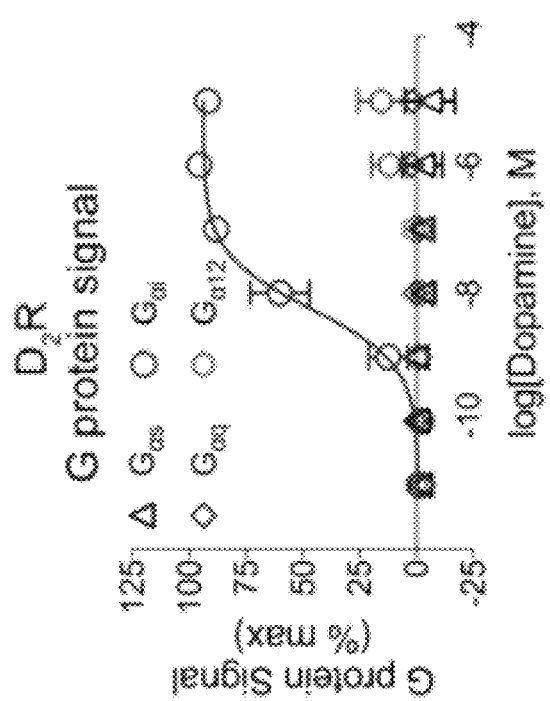
Figure 6E:
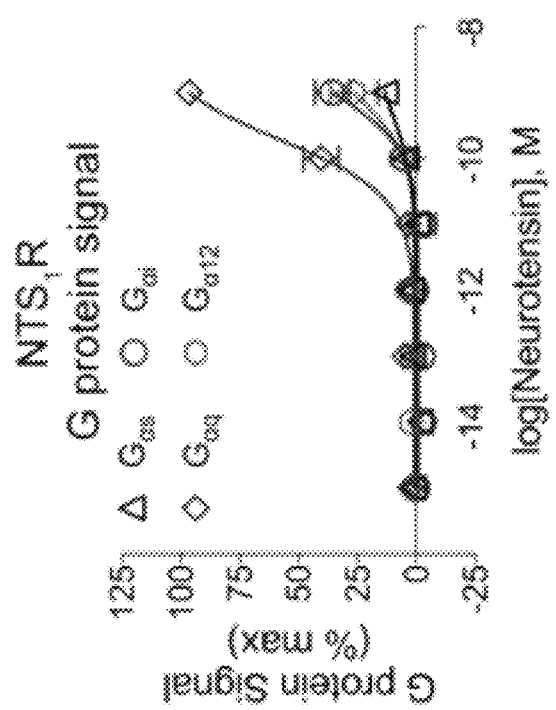
Figure 6F:
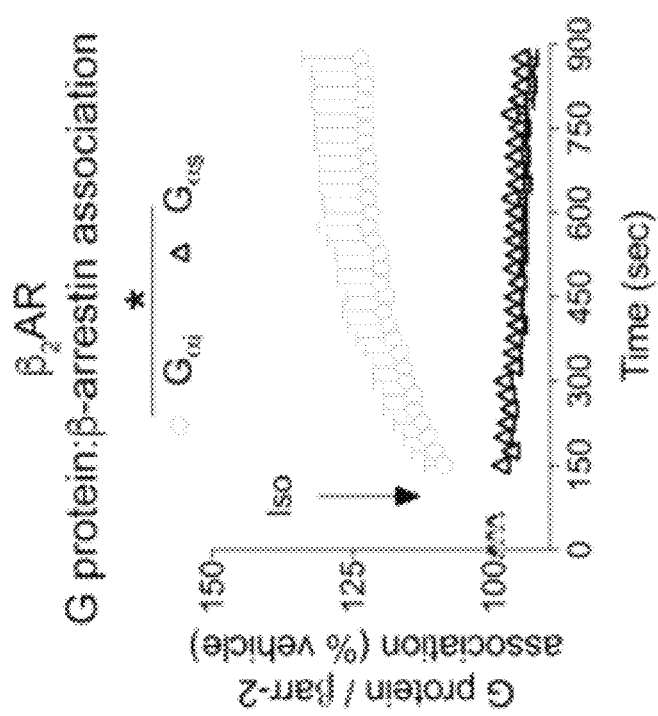
Figure 6G:
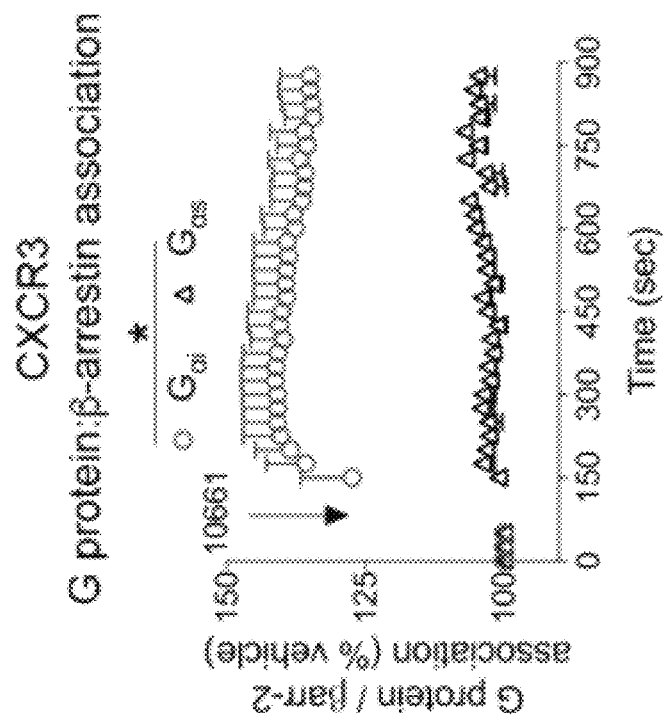
Figure 6H:
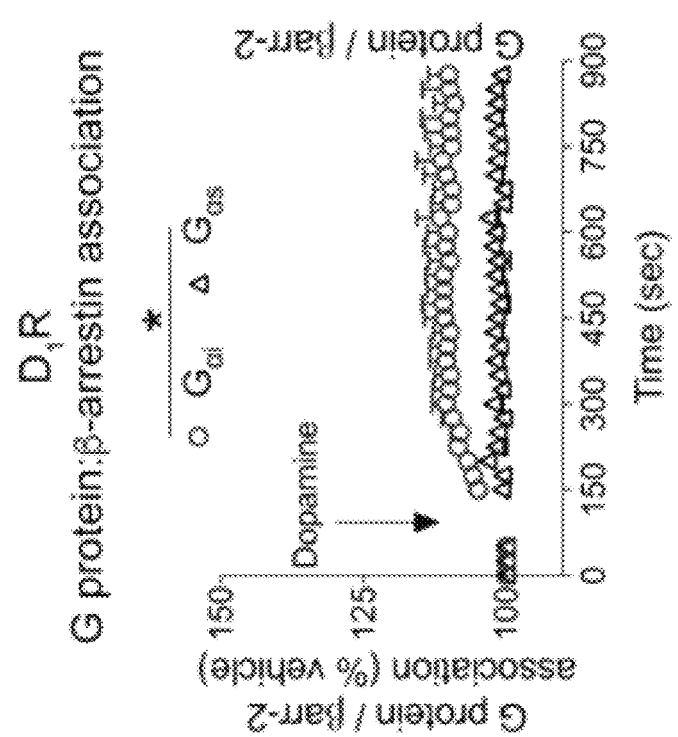
Figure 6I:
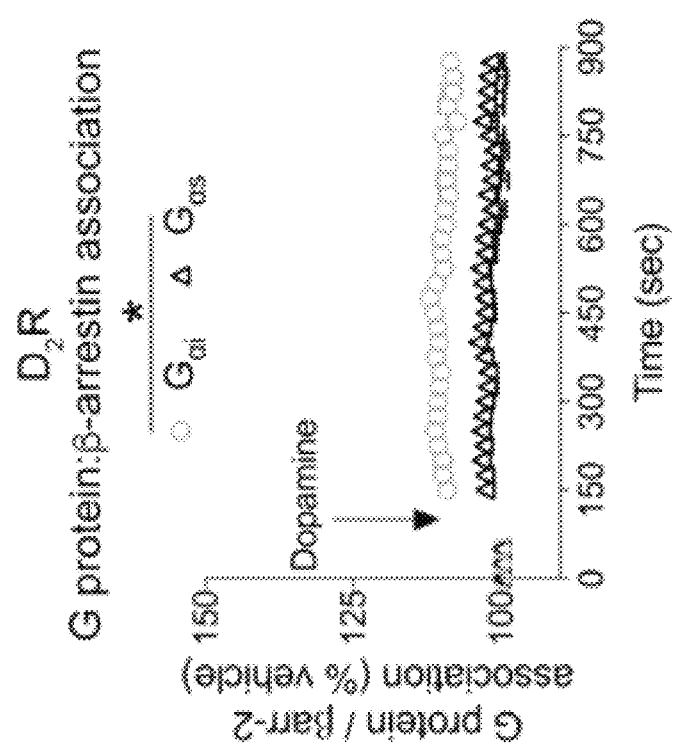
Figure 6J:
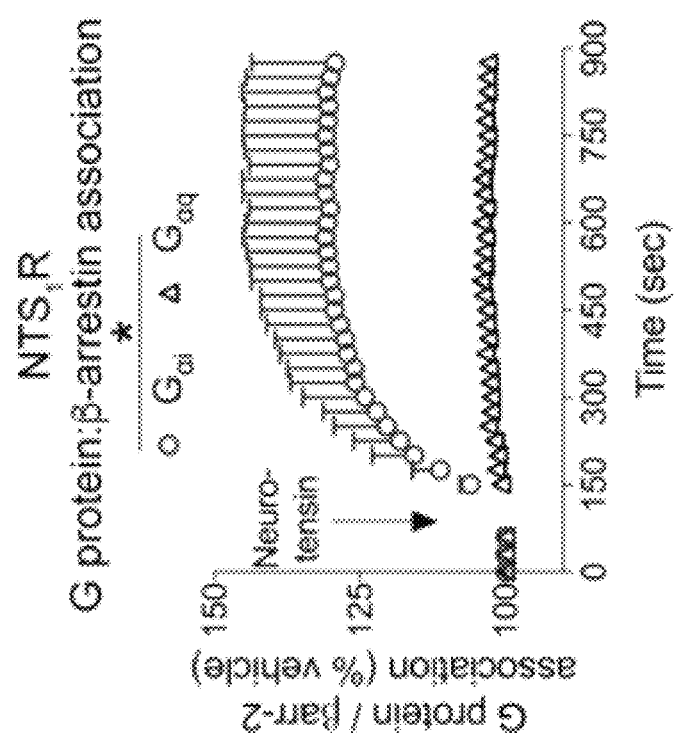

After investigating Gαi recruitment, it was investigated whether disrupting β-arrestin recruitment would impair Gαi:β-arrestin complex formation. GPCR kinases (GRKs) phosphorylate intracellular serine and threonine residues, often within the C-terminal tail, to promote binding of β-arrestin. β-arrestin interacts with both a phosphorylated GPCR tail, as well as the receptor core. To probe the contribution of the phosphorylated tail the canonically Gαi-coupled chemokine receptor CXCR3 with a functional C-terminal truncation mutant (CXCR3 L344X, lacking phosphorylatable tail residues) was used. Both the L344X mutation or a mutation of four C-terminal serine and threonine residues to alanine (CXCR3 4xA) resulted in CXCR3 receptors that were equivalently expressed on the cellular surface as WT CXCR3 (FIGS. 5A and 5B). Canonical Gαi signaling downstream of CXCR3 L344X showed a greater response (left shifted EC50 and higher E max) than either WT CXCR3 or CXCR3 4xA (FIG. 5C). For β-arrestin-2 recruitment, both CXCR3 L344X and CXCR3 4xA had an attenuated response (lower E max) relative to WT CXCR3 (FIG. 5D). Similarly, the mutant CXCR3s displayed reduced Gαi:β-arrestin complex formation (FIG. 5E) but with similar kinetics (FIG. 5F) compared with the WT CXCR3. These findings suggest that β-arrestin recruitment to the receptor drives Gαi:β-arrestin complex formation, but unlike the Gαs:β-arrestin:GPCR megaplex, an interaction with the receptor C-terminal tail is dispensable.

Figure 4J:
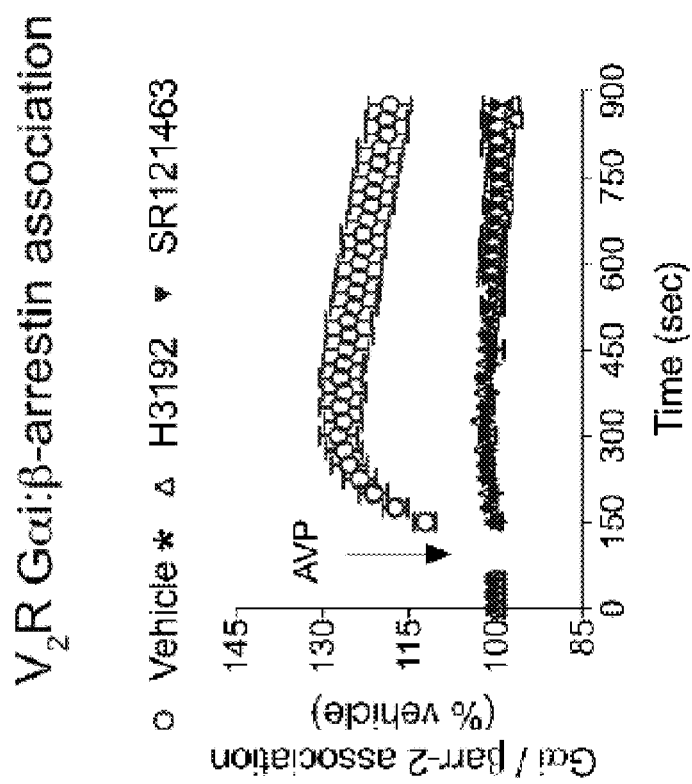
Figure 4K:
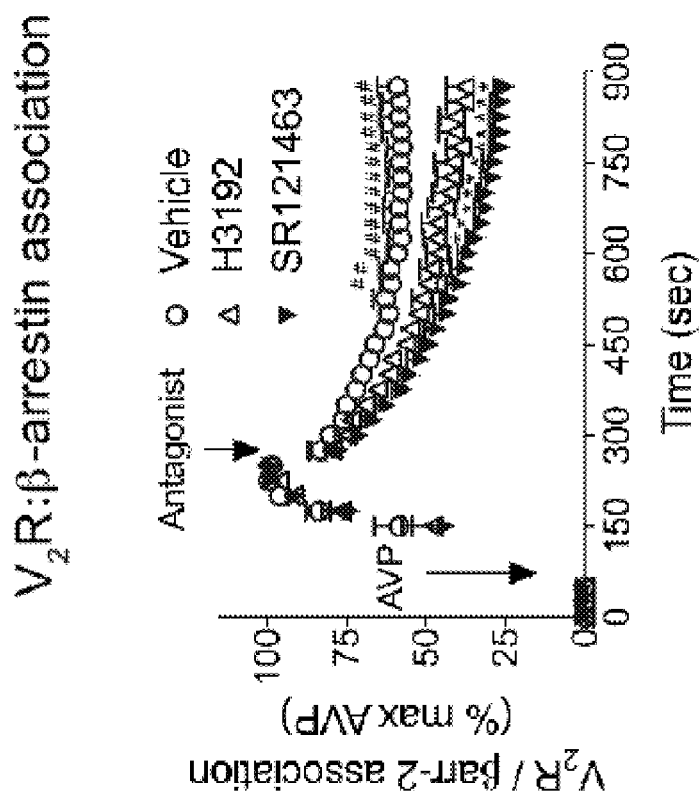
Figure 4L:
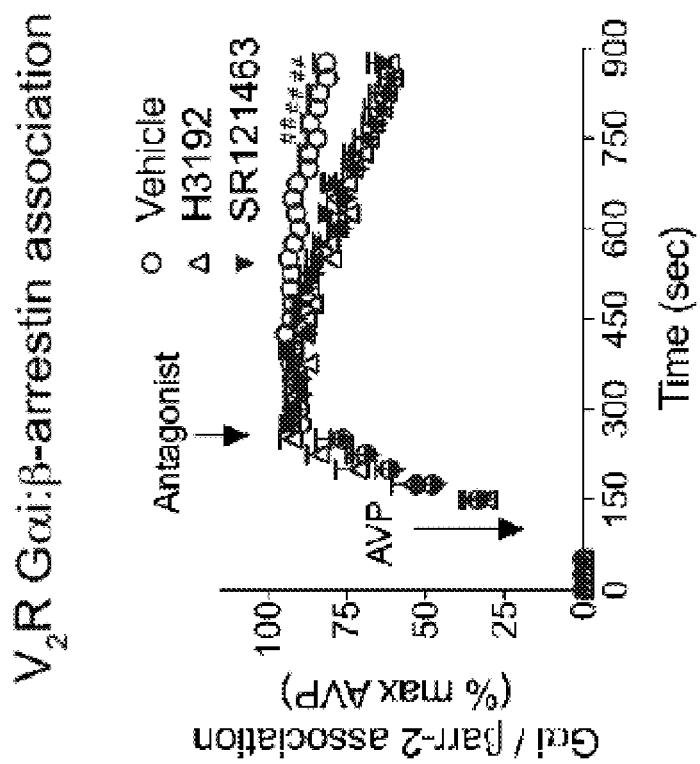

Next, V2R antagonists were used to assess the reversibility of Gαi:β-arrestin complex formation. Pretreatment of HEK 293 cells overexpressing V2R with either a membrane-permeant V2R antagonist (SR121463) or a membrane-impermeant V2R antagonist (H3192) prevented formation of Gαi:β-arrestin complexes (FIG. 4J). The ability of these antagonists with different cell permeability properties to disrupt β-arrestin association either with V2R or Gαi was assessed. It is well-established that interactions between the V2R and β-arrestin occur both at the plasma membrane as well within intracellular endosomes. The membrane-permeant antagonist was more efficient at reversing V2R:β-arrestin association than the membrane-impermeant antagonist (FIG. 4K). In contrast, both antagonists equivalently disrupted Gαi:β-arrestin complexes (FIG. 3L), suggesting that Gαi:β-arrestin complexes are present primarily at the plasma membrane, consistent with the confocal findings. The antagonist experiments also demonstrate the reversible nature of this complex as well as confirm that the underlying interaction between Gαi and β-arrestin determines the complementation (and thereby signal) of the NANOBIT® system. After antagonist addition the half-life of the Gαi:β-arrestin complexes was longer than that of the V2R:β-arrestin complexes, as shown in the below Table 1. Together, these findings suggest that Gαi:β-arrestin complexes are distinct from the previously described Gαs:β-arrestin:GPCR megaplex.

TABLE 1

Half-life of V2R:β-arrestin-2 and $G_{\alpha i}$:β-arrestin-2 complexes is differentially affected by membrane permeant versus impermeant V2R antagonists.

| | Half-life (sec) | | |
|---|---|---|---|
| Experimental condition | Vehicle | H3192 (impermeable) | SR121463 (permeable) |
| V2R-LgBiT:β-arrestin-smBiT | 660 | 430 | 320 |
| $G_{\alpha i}$-LgBiT:β-arrestin-smBiT | 2570 | 1150 | 1140 |

A Variety of GPCRs Promote the Formation of Gαi:β-Arrestin Complexes

Given the paradoxical results of the Gαs-coupled V2R catalyzing a unique Gαi:β-arrestin complex, it was investigated whether this phenomenon was generalizable to other GPCRs. Five GPCRs (β2AR, CXCR3, neurotensin 1 receptor (NTS$_1$R), and dopamine receptors D1 (D$_1$R) and D2 (D$_2$R)) were selected to compare their Gαi:β-arrestin complex formation ability to their ability to form complexes between β-arrestin and their canonically coupled Gα subtype (or Gαs in the case of canonically Gαi-coupled GPCRs). It was first confirmed that the canonical G protein coupling of these GPCRs (FIGS. 6-A-E). Only CXCR3 and D$_2$R canonically signaled through Gαi, with β$_2$AR and D$_1$R primarily coupling to Gαs and NTS$_1$R primarily to Gαq. All five of these GPCRs formed Gαi:β-arrestin complexes following agonist treatment with no discernable complexes between the other Gα subunits and β-arrestin (FIGS. 6F-J), suggesting that formation of Gαi:β-arrestin complexes is a unique and common mechanism across GPCRs.

Gαi:β-Arrestin Complexes Facilitate ERK Scaffolding and Signaling

Figure 7A:
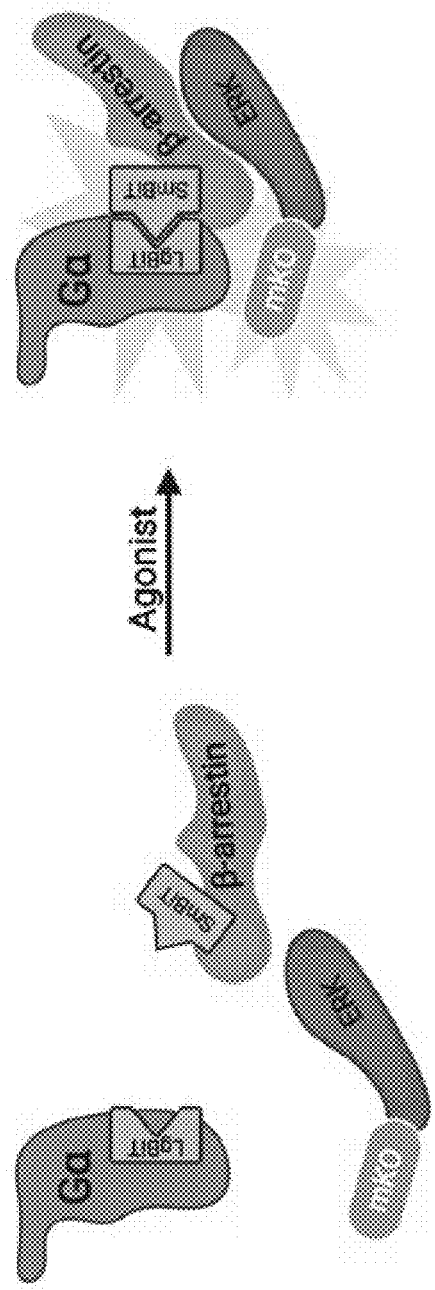
FIGS. 7A-F show that Gαi: β-arrestin scaffolds form functional complexes with ERK, where
Figure 7B:
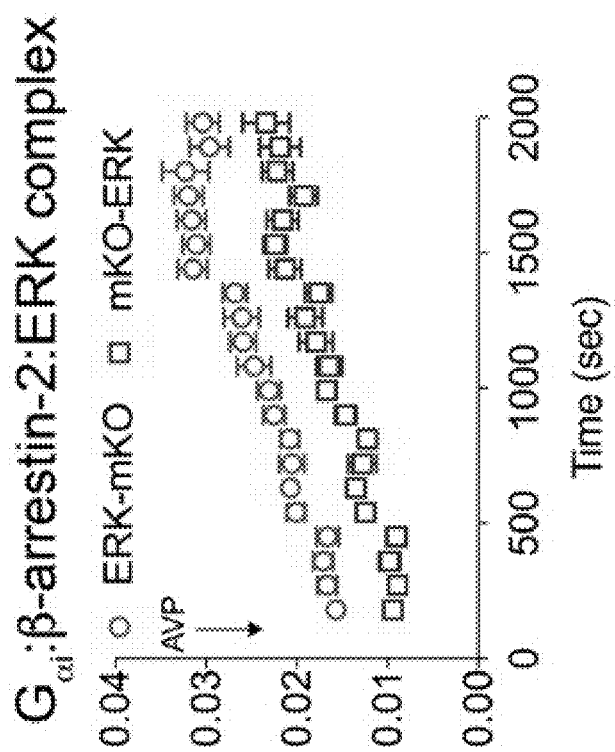

After identifying Gαi:β-arrestin complexes generated by multiple receptors, their potential functional consequences were tested by assessing whether these complexes could scaffold ERK1/2 MAP kinases, which play critical roles in cell cycle regulation/proliferation and survival/apoptotic signaling. Without being bound by theory, GPCRs are thought to regulate ERK activation via phosphorylation through separate G protein and β-arrestin signaling pathways. To investigate if Gαi:β-arrestin complexes could directly scaffold to ERK downstream of the V2R, complex BRET was used by tagging ERK at either its N- or C-terminus with the dipole acceptor mKO (FIG. 7A). Data were normalized to an untagged (cytosolic) mKO to account for changes in protein localization following agonist treatment. Agonist treatment of V2R catalyzed the formation of a Gαi:β-arrestin:ERK complex (FIG. 7B). The magnitude of the adjusted complex BRET ratio was dependent on the location of the mKO tag on ERK (ERK-mKO compared to mKO-ERK), consistent with orientation and distance dependence of resonance energy transfer between the luciferase donor and mKO dipole acceptor.

Figure 7C:
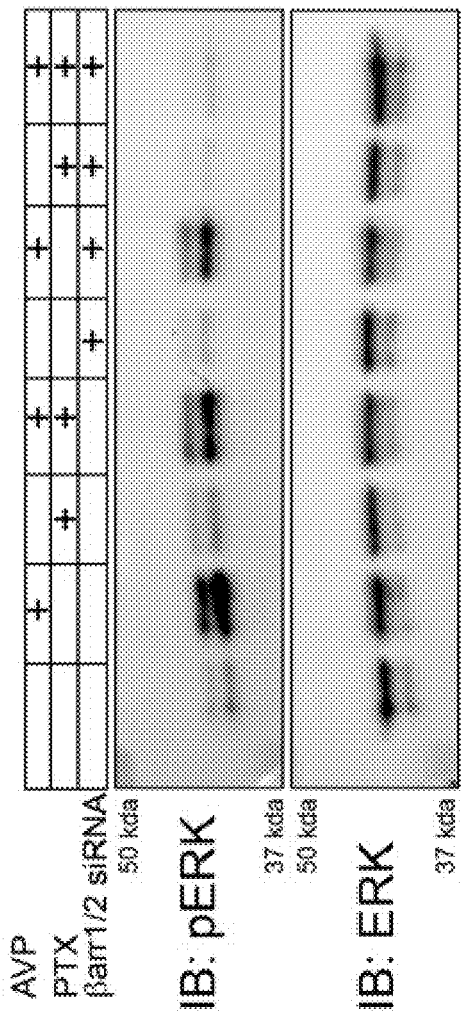
Figure 7D:
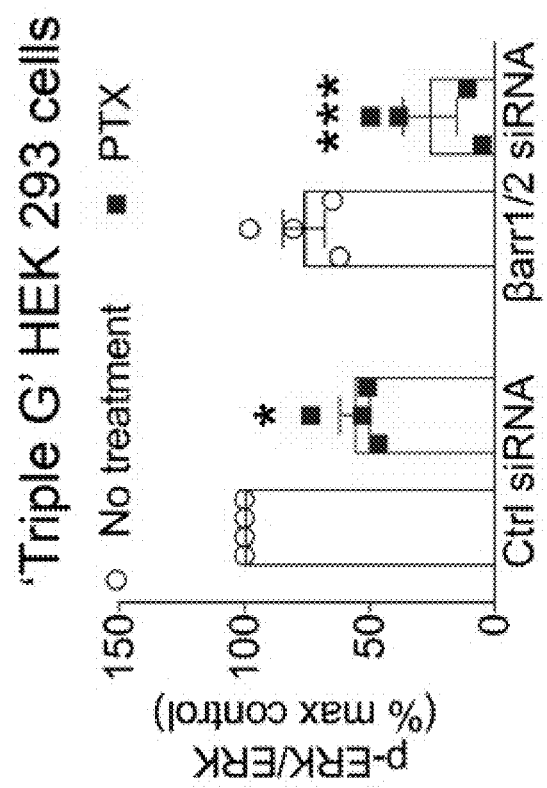
Figure 7E:
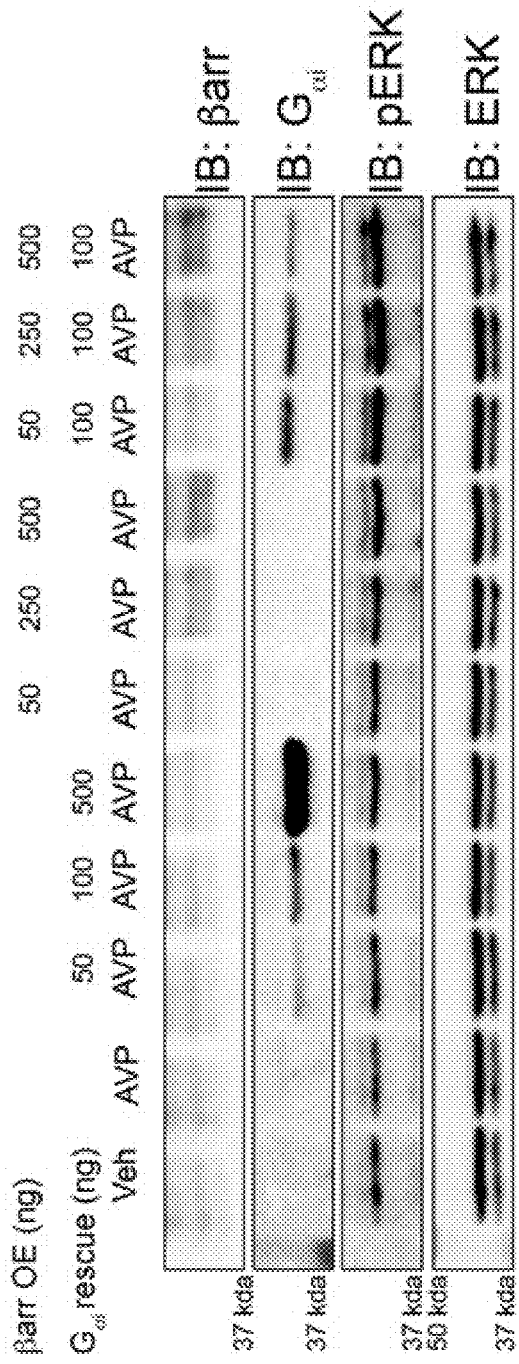
Figure 7F:
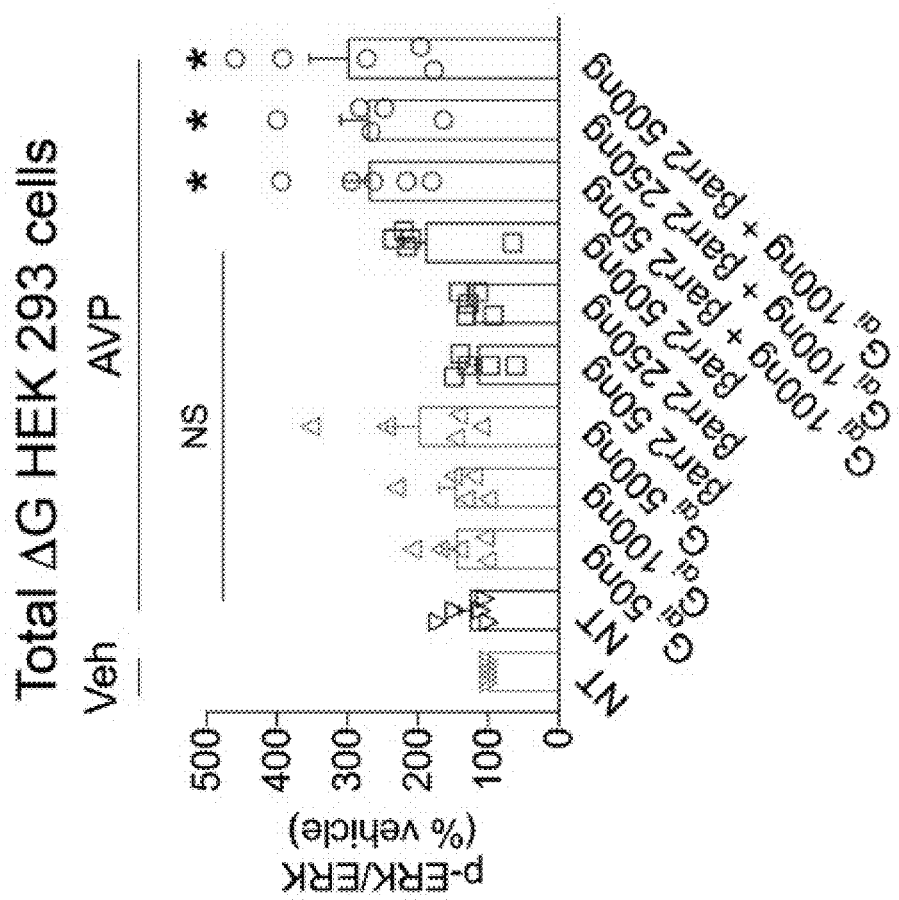

To selectively evaluate the contributions of Gαi signaling on ERK phosphorylation, triple Gα subfamily-KO ('Δ3G') HEK 293 cells depleted via CRISPR/Cas9 technology of three Gα protein subfamilies, Gαs/Gαolf, Gαq/11, and Gα12/13 (only Gαi members present) were used. Agonist treatment of these 'triple G' HEK 293 cells overexpressing V2R robustly increased phosphorylated ERK (FIGS. 7C and 7D). Pretreatment with pertussis toxin abrogated, but did not eliminate, ERK phosphorylation in 'triple G' cells (FIGS. 7C and 7D). In 'triple G' cells, pertussis toxin pretreatment in combination with β-arrestin1/2 knockdown essentially eliminated ERK phosphorylation (FIGS. 7C and 7D), consistent with functional coordination of Gαi and β-arrestin. Similar effects of pertussis toxin pretreatment on ERK phosphorylation were observed in 'triple G' cells transiently overexpressing the β2AR, D1R, or NTS1R. Quadruple Gα subfamily-KO ('total G') HEK 293 cells (lacking all Gα proteins) and rescued Gαi expression and/or increased expression of β-arrestin supported these findings. Increasing expression of both, but not of either protein alone, significantly increased ERK phosphorylation following AVP treatment in 'total G' cells relative to control condition (FIGS. 7E and 7F). These results are consistent with a role of Gαi:β-arrestin complexes in promoting ERK phosphorylation.

Figure 8A:
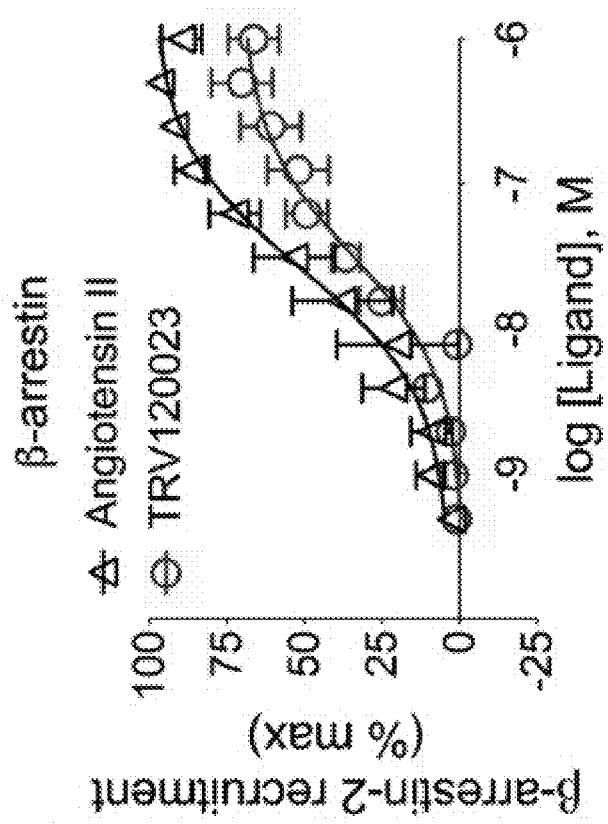
FIGS. 8A-G show that cell migration to the β-arrestin-biased ligand TRV120023 require both Gαi and β-arrestins, including a BRET assay quantifying the recruitment of β-arrestin-2-YFP to $AT_1R$-RlucII following treatment with either angiotensin II or TRV120023, with the assessment of canonical G protein signaling via TGF-α shedding assay at the Angiotensin II type 1 receptor ($AT_1R$) following treatment with either the endogenous ligand (FIG. 8A), angiotensin II (FIG. 8B) or the β-arrestin-biased ligand TRV120023 (FIG. 8C)
Figure 8B:
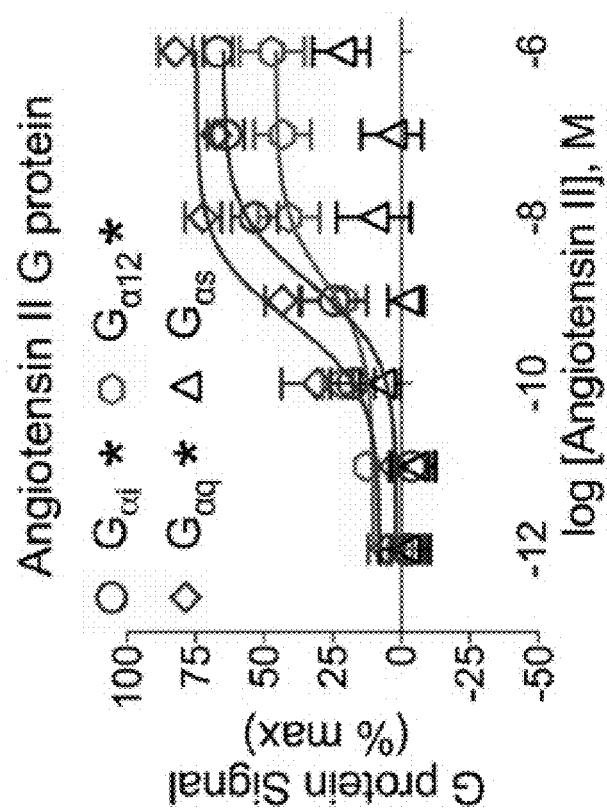
Figure 8C:
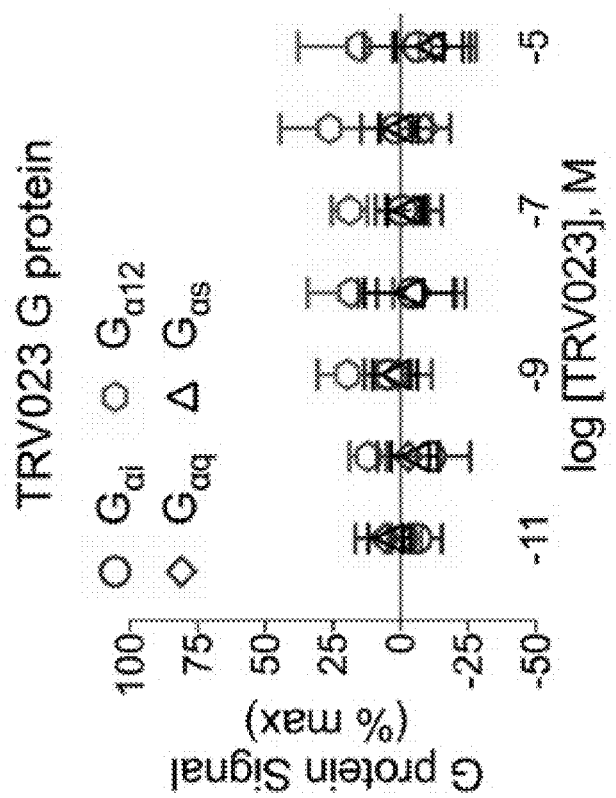
Figure 8D:
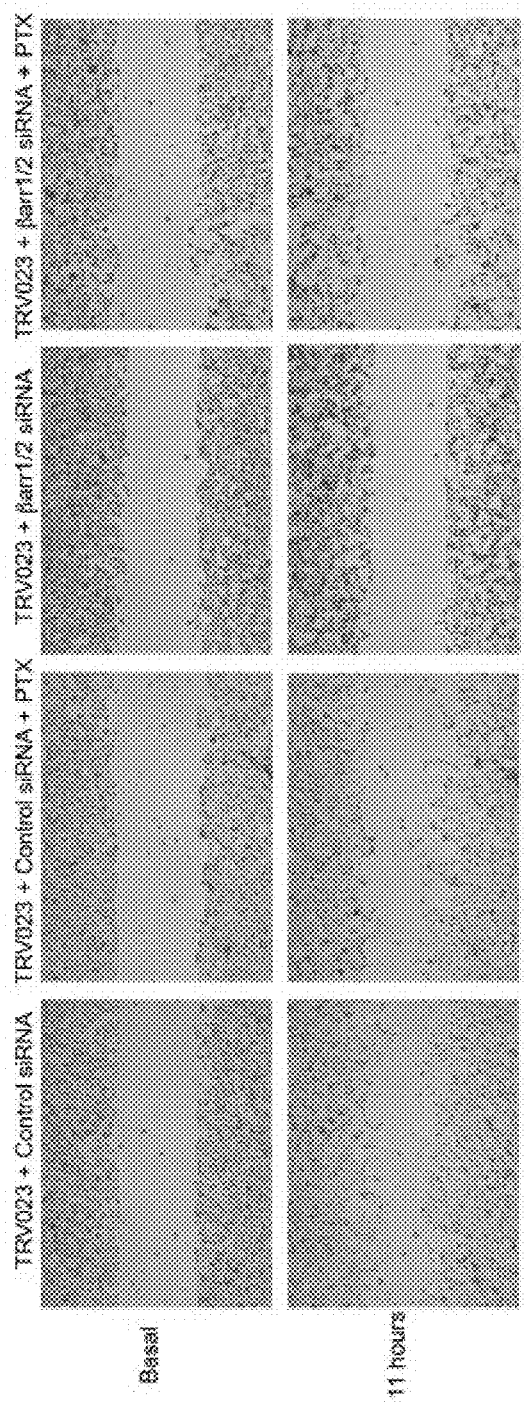
Figure 8E:
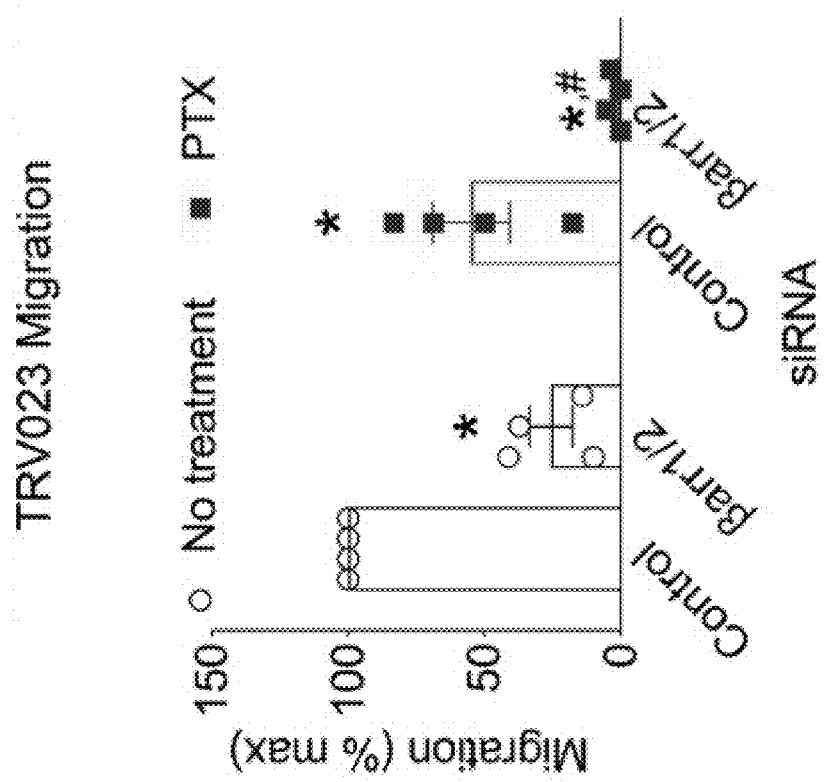
Figure 8F:
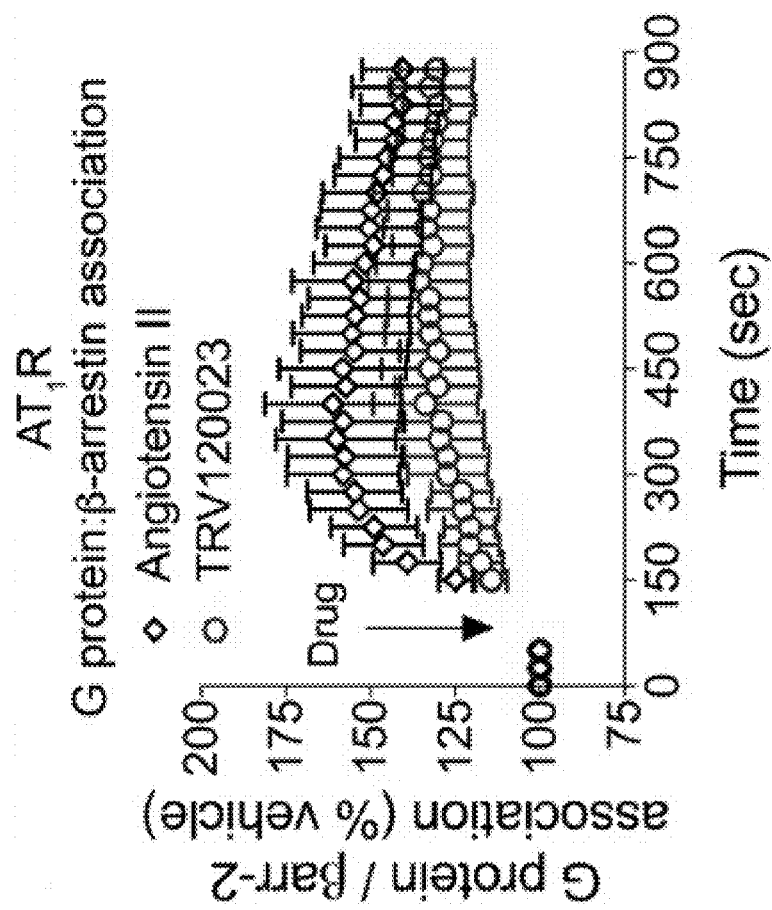

A β-Arrestin-Biased AT1R Agonist Promotes Formation of the Gαi: β-Arrestin Complex and Displays Pertussis Toxin-Sensitive Cell Migration To evaluate whether the formation of Gαi:β-arrestin complexes also occur in the absence of canonical G protein activation, the angiotensin type 1 receptor (AT1R) β-arrestin-biased agonist, TRV120023, which does not promote canonical G protein signaling but robustly recruits β-arrestin (FIG. 8A), was used. The biased agonist TRV120023 contrasts with the endogenous ligand of AT1R, Angiotensin II (AngII), which canonically signals through both Gαq and Gαi (FIG. 8B) and recruits β-arrestin (FIG. 8A). TRV120023 is a β-arrestin-biased agonist as shown in the assays, and it had no appreciable ability to promote canonical G protein signaling through any of the four Gα-family proteins tested (FIG. 8C) while strongly stimulating β-arrestin recruitment to the receptor (FIG. 8A). Because TRV120023 does not appreciably activate canonical G protein signaling, it would be predicted that it would not induce cell migration, a function thought to require canonical G protein signaling. However, not only did TRV120023 promote cellular migration, this migration was pertussis toxin sensitive, as pretreatment of cells with pertussis toxin reduced TRV120023-mediated migration by ~50%. Furthermore, inhibition of both Gαi and β-arrestin through pertussis toxin pretreatment and siRNA knockdown of β-arrestin1/2 eliminated migration in HEK 293 cells stably expressing AT1R (FIGS. 8D and 8E). Migration of primary human pulmonary arterial smooth muscle cells (PASMCs) towards TRV120023 was also pertussis toxin sensitive, indicating that this observation was not unique to immortalized model cell lines and this mechanism likely occurs with physiological levels of receptor and effector expression. Similar to all other receptors tested in the current study, both the endogenous agonist AngII and the β-arrestin-biased agonist TRV120023 induced Gαi:β-arrestin complex formation (FIG. 8F). These findings are consistent with Gαi:β-arrestin complexes promoting functional responses downstream of GPCRs.

Discussion

Figure 8G:
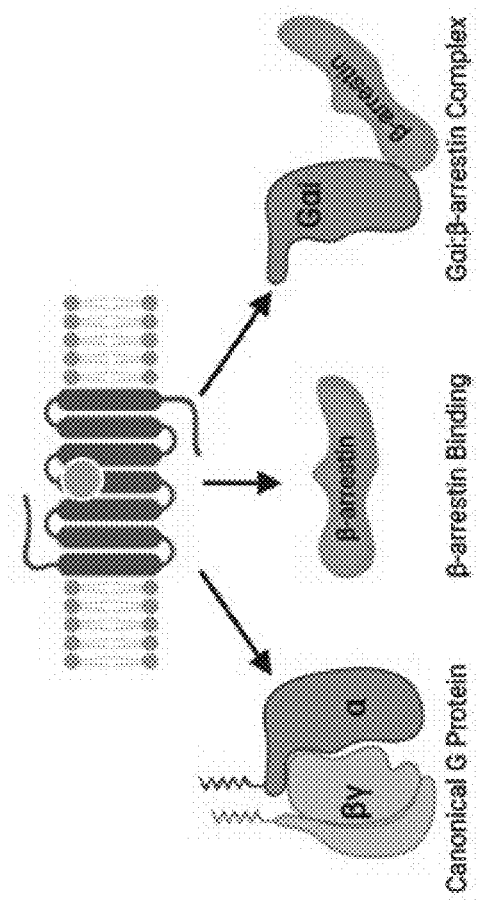

The above results reveal a new GPCR signaling paradigm in which GPCRs can promote formation of Gαi:β-arrestin complexes. These Gαi:β-arrestin complexes were observed downstream of all receptors tested, even with receptors that do not canonically signal through Gαi. A variety of GPCR ligands were able to drive formation of Gαi:β-arrestin complexes, even the β-arrestin-biased ligand TRV120023, which has little or no ability to promote classical G protein-mediated signaling. The data suggests that a major determinant of β-arrestin association with Gαi is GPCR-mediated recruitment of β-arrestin to the plasma membrane. Observed Gαi:β-arrestin scaffolds can include a GPCR, or a signaling effector (ERK), or possibly both, and indicate that Gαi:β-arrestin scaffolds form functional signaling complexes. Remarkably, these signaling complexes were associated with V2R-mediated ERK activation, even though the stimulatory GPCR ligand (AVP) is incapable of activating canonical Gαi signaling. Using HEK 293 cells depleted of the Gαs/q/12 proteins and overexpressing the V2R, it was demonstrated that AVP-induced ERK phosphorylation is nearly eliminated following Gαi inhibition with pertussis toxin and β-arrestin knockdown with siRNA. Furthermore, rescue of Gαi in cells lacking all functional G proteins combined with overexpression of β-arrestin, but not either β-arrestin overexpression or Gαi rescue alone, significantly increased AVP-induced ERK phosphorylation. In addition, it was shown that pertussis toxin impairs migration of both primary human PASMCs and immortalized cells treated with a β-arrestin-biased AT$_1$R ligand, TRV120023. The data indicates possible functional roles for Gαi:β-arrestin scaffolds in the process of ERK activation and cell migration (FIG. 8G). This study bridges these seemingly contradictory results concerning the interplay of G protein and β-arrestin signaling by delineating a previously unappreciated direct Gαi:β-arrestin scaffolding complex. Furthermore, this study further suggests that the activated state of β-arrestin persists even when it is not bound to a receptor. This work also offers plausible mechanistic insight into initially paradoxical observations that Gαi can drive ERK phosphorylation downstream of the canonically Gαs-coupled V2R and that pertussis toxin inhibits cell migration to a β-arrestin-biased agonist.

The findings demonstrate that GPCRs can form Gαi:β-arrestin complexes, and that these Gαi:β-arrestin complexes appear necessary for certain aspects of β-arrestin signaling, which have the way for new avenues for therapeutic targeting of GPCRs.

What is claimed is:

1. A method for detecting protein interactions in a sample, the method comprising:
   (a) detecting a first polypeptide and a second polypeptide that when associated emit a first detectable signal in a first light emission spectrum, wherein the first polypeptide is conjugated to a first non-luminescent element and the second polypeptide is conjugated to a second non-luminescent element, wherein the first and second non-luminescent elements form a complex that emits the first detectable signal;
   (b) contacting the first polypeptide and the second polypeptide with a third polypeptide conjugated to a dipole acceptor moiety that has a second light emission spectrum when excited within a light excitation spectrum, wherein the light excitation spectrum overlaps with the first light emission spectrum, wherein the contacting places the first polypeptide and the second polypeptide in a proximity sufficient to allow resonance energy transfer from the first and the second polypeptides to the dipole acceptor moiety, thereby exciting the dipole acceptor moiety to emit a second detectable signal;
   (c) detecting the second detectable signal emitted in the second light emission spectrum by the dipole acceptor moiety and
   (d) determining (i) an increase in a ratio of the second detectable signal:the first detectable signal after the contact between the first polypeptide, the second polypeptide, and the third polypeptide, as compared to a ratio of the second detectable signal: the first detectable signal before the contact between the first polypeptide, the second polypeptide, and the third polypeptide, or (ii) an increase in the second detectable signal following association between the first polypeptide, the second polypeptide and the third polypeptide,
   wherein the increase in (i) or (ii) indicates that the first polypeptide, the second polypeptide and the third polypeptide interact to form a complex.

2. The method of claim 1, wherein the dipole acceptor moiety comprises a fluorescent moiety, a dye, an arsenical protein label, a dye-protein conjugate pair, or a quantum dot.

3. The method of claim 1, wherein the dipole acceptor moiety comprises a fluorescent moiety.

4. The method of claim 3, wherein the second light emission spectrum is within a range of from about 445 nm to about 700 nm.

5. The method of claim 1, wherein the first non-luminescent element and the second non-luminescent element each independently comprise a portion of a luciferase enzyme.

6. The method of claim 1, wherein the sample comprises a cell, and the contacting is performed by molecular interactions in the cell.

* * * * *

SEQUENCE LISTING

```
<160> NUMBER OF SEQ ID NOS: 1

<210> SEQ ID NO 1
<211> LENGTH: 171
<212> TYPE: PRT
<213> ORGANISM: Artificial Sequence
<220> FEATURE:
<223> OTHER INFORMATION: Synthetic Sequence

<400> SEQUENCE: 1

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
```

-continued

```
               100                 105                 110
Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```